US008105593B2

(12) United States Patent
Kinney et al.

(10) Patent No.: US 8,105,593 B2
(45) Date of Patent: Jan. 31, 2012

(54) ANTI-ADDL MONOCLONAL ANTIBODY AND USE THEREOF

(75) Inventors: Gene Kinney, Collegeville, PA (US); William R. Strohl, Bridgewater, NJ (US); Zhiqiang An, Ambler, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 85 days.

(21) Appl. No.: 12/793,775

(22) Filed: Jun. 4, 2010

(65) Prior Publication Data

US 2010/0239597 A1 Sep. 23, 2010

Related U.S. Application Data

(63) Continuation of application No. 11/581,843, filed on Oct. 17, 2006, now Pat. No. 7,731,962, which is a continuation-in-part of application No. 11/256,332, filed on Oct. 21, 2005, now Pat. No. 7,780,963.

(60) Provisional application No. 60/652,538, filed on Feb. 14, 2005.

(51) Int. Cl.
*A61K 39/395* (2006.01)
*C07K 16/18* (2006.01)
*G01N 33/53* (2006.01)

(52) U.S. Cl. ............... 424/133.1; 530/387.3; 530/388.1; 435/7.2; 424/141.1

(58) Field of Classification Search .................. None
See application file for complete search history.

(56) References Cited

U.S. PATENT DOCUMENTS

| | | | |
|---|---|---|---|
| 6,218,506 B1 | 4/2001 | Krafft et al. | 530/324 |
| 6,492,123 B1 | 12/2002 | Holliger et al. | 435/7.1 |
| 6,743,427 B1 | 6/2004 | Schenk | 424/130.1 |
| 6,750,324 B1 | 6/2004 | Schenk et al. | 530/387.1 |
| 6,761,888 B1 | 7/2004 | Schenk | 424/130.1 |
| 6,787,637 B1 | 9/2004 | Schenk | 530/387.1 |
| 6,797,492 B2 | 9/2004 | Daugherty et al. | 435/69.6 |
| 6,913,745 B1 | 7/2005 | Schenk | 424/130.1 |
| 2003/0068316 A1 | 4/2003 | Klein et al. | 424/130.1 |
| 2006/0057701 A1 | 3/2006 | Rosenthal et al. | 435/252.3 |

FOREIGN PATENT DOCUMENTS

| | | |
|---|---|---|
| WO | WO 97/11971 | 4/1997 |
| WO | WO 03/104437 | 12/2003 |
| WO | WO 2005/025516 | 3/2005 |

OTHER PUBLICATIONS

Paul W. E. Fundamental Immunology, 3rd edition, 1993, pp. 292-295.*
Rudikoff et al. Single amino acid substitution altering antigen-binding specificity. Proc Natl Acad Sci U S A. Mar. 1982; 79(6):1979-83.*
U.S. Appl. No. 60/621,776, filed Oct. 25, 2004.
U.S. Appl. No. 60/652,538, filed Feb. 14, 2005.
U.S. Appl. No. 60/695,526, filed Jun. 30, 2005.
U.S. Appl. No. 60/695,528, filed Jun. 30, 2005.
Armour et al. , "Recombinant human IgG molecules lacking Fcγ receptor I binding and monocyte triggering activities", Eur. J. Immuno. 1999 29:2613.
Birmingham, K. and Frantz, S. , "Set back to Alzheimer vaccine studies", Nat. Med. 2002 8:199-200.
Bitan et al., "Neurotoxic protein oligomers—what you see is not always what you get", Amyloid 2005 12 (2) :88-95.
Canfield and Morrison, "The Binding Affinity of Human IgG for its High Affinity Fc Receptor Is Determined by Multiple Amino Acids in the $C_H2$ Domain and Is Modulated by the Hinge Region", J. Exp. Med. 1991 173:1483-1491.
Chang et al., "Femtomole Immunodetection of Synthetic and Endogenous Amyloid-β Oligomers and Its Application to Alzheimer's Disease Drug Candidate Screening", J. Molecular Neuroscience 2003 20:305-313.
Dodart et al. , "Immunization reverses memory deficits without reducing brain Aβ burden in Alzheimer's disease model", Nat . Neurosci. 2002 5:452-457.
Gong et al., "Alzheimer's disease-affected brain: Presence of oligomeric Aβ ligands (ADDLs) suggests a molecular basis for reversible memory loss", Proc. Natl. Acad. Sci. USA 2003 100:10417-10422.
Hardy et al., "The Amyloid Hypothesis of Alzheimer's Disease:Progress and Problems on the Road to Therapeutics", Science 2002 297:353-356.
Hock et al., "Antibodies against β-Amyloid Slow Cognitive Decline in Alzheimer's Disease", Neuron 2003 38:547-554.
Hougs et al., "The first constant-domain (CH1) exon of human *IGHG2* is polymorphic and in strong linkage disequilibrium with the CHW exon polymorphism encoding the G2m(n+) allotype in Caucasians", Immunogenetics 2001 52:242-248.
Ida et al. , "Analysis of Heterogeneous βA4 Peptides in Human Cerebrospinal Fluid and blood by a Newly Developed Sensitive Western Blot Assay", J. Biol. Chem. 1996 271(37):22903-22914.
Kayed et al., "Common Structure of Soluble Amyloid Oligomers Implies Common Mechanism of Pathogenesis", Science 2003 300:486-489.
Klein, William L., "Aβ toxicity in Alzheimer's disease:globular oligomers (ADDLs) as new vaccine and drug targets", Neurochemistry International 2002 41:345-352.
Kotilnek et al. , "Reversible Memory Loss in a Mouse Transgenic Model of Alzheimer's Disease", J. Neurosci 2002 22:6331-6335.
Lambert et al., "Vaccination with soluble Aβ oligomers generates toxicity-neutralizing antibodies", J. Neurochemistry 2001 79:595-605.
Lambert et al., "Diffusible, nonfibrillar ligands derived from $Aβ_{1-42}$ are potent central nervous system neurotoxins", Proc. Natl. Acad. Sci. USA 1998 95:6448-6453.
Lathe, R., "Synthetic Oligonucleotide Probes Deduced from Amino Acid Sequence Data-Theoretical and Practical Considerations", J. Mol. Biol. 1985 183:1-12.

(Continued)

*Primary Examiner* — Daniel E Kolker
*Assistant Examiner* — Gregory S Emch
(74) *Attorney, Agent, or Firm* — Licata & Tyrrell, P.C.

(57) ABSTRACT

The present invention relates to antibodies that differentially recognize multi-dimensional conformations of Aβ-derived diffusible ligands, also known as ADDLs. The antibodies of the invention can distinguish between Alzheimer's Disease and control human brain extracts and are useful in methods of detecting ADDLs and diagnosing Alzheimer's Disease. The present antibodies also block binding of ADDLs to neurons, assembly of ADDLs, and tau phosphorylation and are there useful in methods for the preventing and treating diseases associated with soluble oligomers of amyloid β 1-42.

12 Claims, 16 Drawing Sheets

OTHER PUBLICATIONS

Lu et al., "A second cytotoxic proteolytic peptide derived from amyloid β-protein precursor", Nat. Med. 2000 6:397-404.

Medgyesi et al., "Functional mapping of the FcγRll binding site on human IgG1 by synthetic peptides", Eur. J. Immunol. 2004 34:1127-1135.

Padlan, Eduardo A., "Anatomy of the Antibody Molecule", Molecular Immunology 1994 31(3):169-217.

Tao et al., "The Differential Ability of Human IgG1 and IgG4 to Activate Complement Is Determined by the COOH-terminal Sequence of the $C_H2$ Domain", J. Exp. Med. 1991 173:1025-1028.

Xu et al., "Residue at Position 331 in the IgG1 and IgG4 $C_H2$ Domains Contributes to Their Differential Ability to Bind and Activate Complement", J. Biol. Chem 1994 269:3469-3474.

Zuckier et al., "The Use of Severe Combined Immunodeficiency Mice to Study the Metabolism of Human Immunoglobulin G", Cancer Suppl. 1994 73:794-799.

Terry et al., "Physical Basis of Cognitive Alterations in Alzheimer's Disease:Synapse Loss Is the Major Correlate of Cognitive Impairment", Ann Neurol 1991 30:572-580.

Selkoe, Dennis J., "Alzheimer's Disease Is a Synaptic Failure", Science 2002 298:789-791.

Coyle, Joseph T., "Alzheimer's Disease", 1987 In:Encylopedia of Neuroscience, Adelman (ed) Birthauser, Boston-Basel-Stuttgart, pp. 29-31.

Hawkins et al., "Selection of Phage Antibodies by Binding Affinity Mimicking Affinity Maturation", J. Mol. Biol. 1992 226:889-896.

Jespers et al., "Guiding the Selection of Human Antibodies from Phage display repertoires to a Single Epitope of an Antigen", 1994 Bio/Technology 12:899-903.

Katzman et al., "Clinical, Pathological and Neurochemical Changes in Dementia:A Subgroup with Preserved Mental Status and Numerous Neocortical Plaques", Annals of Neurology 1988 23(2):138-144.

Low et al., "Mimicking Somatic Hypermutation:Affinity Maturation of Antibodies Displayed on Bacteriophage Using a Bacterial Mutator Strain", J. Mol. Biol. 1996 260:359-369.

Poljak, Roberto J., "Production and structure of diabodies", Structure 1994 2:1121-1123.

Wilock at al., "Deglycosylated Anti-Amyloid-β Antibodies Eliminate Cognitive Deficits and Reduce Parenchymal Amyloid with Minimal Vascular Consequences in Aged Amyloid Precursor Protein Transgenic Mice", J. Neuroscience 2006 26(20):5340-5346.

Zhu et al., "High Level Secretion of a Humanized Bispecific Diabody from *Escherichia coli*", Biotechnology 1996 14:192-196.

Breitling and Dübel 1999 In:Recombinant Antibodies, John Wiley & Sons, Inc., NY p. 115.

Figini et al., "In Vitro Assembly of Repertoires of Antibody Chains on the Surface of of Phage by Renaturation", J. Mol. Biol. 1994 239:68-78.

Holliger et al., "Diabodies":Small bivalent and bispecific antibody fragments, Proc. Natl. Acad. Sci. USA 1993 90:64444-6448.

* cited by examiner

20C2 - HEAVY CHAIN VARIABLE REGION SEQUENCE
tgggcagacttaccattctcattcctgctgctgattgtccctgcatatg
tcttgtccCAAGTTACTCTAAAAGAGTCTGGCCCTGGGATATTGAAGCC
CTCACAGACCCTCAGTCTGACTTGTTCTCTCTCTGGGTTTTCACTGAGC
ACTTCTGGTATGGGTGTAGGCTGGTTTCGTCAGCCTTCAGGGAAGGGTC
TGGAGTGGCTGGCACACATTTGGTGGGATGATGATAAGTCCTATAATCC
ATCCCTGAAGAGCCGGCTCACAATCTCCAAGTATACCTCTAGAAACCAG
GTTTTCCTCACGATCACCAGTGTGGACACTGCAGATACTGCCACTTACT
ATTGTGCTCGAAGACAACTCGGACTAAGATCAATTGATGCTATGGACTA
CTGGGGTCAAGGAACCTCAGTCACCGTCTCCTCAGCCAAAACGACACCC
CCATCTGTCTATCCACTG (SEQ ID NO:103)

*FIG. 1A*

20C2 - LIGHT CHAIN VARIABLE REGION SEQUENCE
agattgcctgttaggctgttggtgctgatgttctggattcctgcttcca
ccagtGATGTTTTGATGACCCAAACTCCTCTCTCCCTGCCTGTCAGTCT
TGGAGATCAAGCCTCCATCTCTTGCAGATCTAGTCAGAGCATTCTACAT
AGTAATGGAAACACCTATTTAGAGTGGTACCTGCAGAAACCAGGCCAGT
CTCCAAAGCTCCTGATCTACAAAGTTTCCAACCGATTTTCTGGGGTCCC
AGACAGGTTCAGTGGCAGTGGATCAGGGACAGATTTCACACTCAAGATC
AGCAGAGTGGAGGCTGAGGATCTGGGAGTTTATTACTGTTTTCAAGGTT
CACTTGTTCCGCTCACGTTCGGTGCTGGGACCAAGCTGGAGCTGAAACG
GGCTGATGCTGCACCAACTGTATCCATCTTCCCACCATCCAGT
(SEQ ID NO:104)

*FIG. 1B*

```
         20C2 QVTLKESGPG ILKPSQTLSL TCSLSGFSLS TSGMGVGWFR QPSGKGLEWL
 VH2 3-1 2-70 QVTLKESGPA LVKPTQTLTL TCTFSGFSLS TSGMRVSWIR QPPGKALEWL
        Hu20C QVTLKESGPA LVKPTQTLTL TCTLSGFSLS TSGMGVGWIR QPPGKALEWL
      Hu20C2A3 QVTLKESGPG LLKPTQTLTL TCTLSGFSLS TSGMGVGWFR QPPGKGLEWL
                                                    HCDR1

20C2 AHIWWDDDKS YNPSLKSRLT ISKYTSRNQV FLTITSVDTA DTATYYCARR
 VH2 3-1 2-70 ARIDWDDDKF YSTSLKTRLT ISKDTSKNQV VLTMTNMDPV DTATYYCARI
        Hu20C AHIWWDDDKS YNPSLKSRLT ISKDTSKNQV VLTMTNMDPV DTATYYCARR
      Hu20C2A3 AHIWWDDDKS YNPSLKSRLT ISKDTSKNQV VLTITNVDPV DTATYYCARR
                                HCDR2

* * *

20C2 QLGLRSIDAMDYW GQGTSVTVSS    (SEQ ID NO:105)
        (JH6)    YYYYYGMDVW GQGTTVTVSS    (SEQ ID NO:106)
       Hu20C2  QLGLRSIDAMDYW GQGTTVTVSS   (SEQ ID NO:107)
      Hu20C2A3 QLGTRGTDAMDYW GQGTTVTVSS   (SEQ ID NO:108)
                HCDR3
```

*FIG. 2A*

```
            20C2 DVLMTQTPLS LPVSLGDQAS ISCRSSQSIL HSNGNTYLEW YLQKPGQSPK
VKII_4-1-(1)A18 DIVMTQTPLS LSVTPGQPAS ISCKSSQSLL HSDGKTYLYW YLQKPGQSPQ
         Hu20C2 DVVMTQSPLS LPVTPGEPAS ISCRSSQSIL HSNGNTYLEW YLQKPGQSPQ
       Hu20C2A3 DVVMTQTPLS LPVTPGQPAS ISCRSSQSIL HSNGNTYLEW YLQKPGQSPQ
                                       LCDR1

*  ***
            20C2 LLIYKVSNRF SGVPDRFSGS GSGTDFTLKI SRVEAEDLGV YYCFQGSLVP
VKII_4-1-(1)A18 LLIYEVSSRF SGVPDRFSGS GSGTDFTLKI SRVEAEDVGV YYCMQGIHLP
         Hu20C2 LLIYKVSNRF SGVPDRFSGS GSGTDFTLKI SRVEAEDVGV YYCLQTTRVP
       Hu20C2A3 LLIYKVSNRF SGVPDRFSGS GSGTDFTLKI SRVEAEDVGV YYCLQTTRVP
                    LCDR2                                       LCDR3

101
            20C2 LTFGAGTKLE LK (SEQ ID NO:109)
          (JK2) YTFGQGTKLE IK (SEQ ID NO:110)
         Hu20C2 LTFGQGTKLE IK (SEQ ID NO:111)
       Hu20C2A3 LTFGQGTKLE IK (SEQ ID NO:112)
```

FIG. 2B

HUMANIZED Hu20C2 (CDR GRAFTED) - HCVRA
caggtgaccctgaaggagtctggccctgccctggtgaagcccacccaga
ccctgaccctgacctgcaccttctctggcttcagcctgagcacctctgg
catgggcgtgggctggatccggcagcccctggcaaggccctggagtgg
ctggcccacatctggtgggacgacgacaagtcctacaacccagcctga
agagccggctgaccatcagcaaggacaccagcaagaaccaggtggtgct
gaccatgaccaacatggaccctgtggacacagccacctactactgtgcc
cggcggcagctgggcctgcggagcattgatgccatggactactggggcc
agggcaccacagtgacagtgtccagc (SEQ ID NO:113)

FIG. 3A

HUMANIZED Hu20C2 (CDR GRAFTED) - HCVRB
caggtgaccctgaaggagtctggccctgccctggtgaagcccacccaga
ccctgaccctgacctgcaccctgtctggcttcagcctgagcacctctgg
catgggcgtgggctggatccggcagcccctggcaaggccctggagtgg
ctggcccacatctggtgggacgacgacaagtcctacaacccagcctga
agagccggctgaccatcagcaaggacaccagcaagaaccaggtggtgct
gaccatgaccaacatggaccctgtggacacagccacctactactgtgcc
cggcggcagctgggcctgcggagcattgatgccatggactactggggcc
agggcaccacagtgacagtgtccagc (SEQ ID NO:114)

FIG. 3B

HUMANIZED Hu20C2 (CDR GRAFTED) - LCVR
gatgtggtgatgacccagagccccctgtccctgcctgtgaccctggcg
agcctgccagcatctcctgccggagctcccagagcatcctgcactccaa
tggcaacacctacctggagtggtacctgcagaagcctggccagagcccc
cagctgctgatctacaaggtgtccaaccggttctccggcgtgcctgacc
ggttcagcggctccggcagcggcacagacttcaccctgaagatcagccg
ggtggaggctgaggatgtgggcgtctactactgcttccagggcagcctg
gtgcccctgacctttggccagggcaccaagctggagatcaag (SEQ
ID NO:115)

FIG. 3C pFab4 Hu20C2 HEAVY CHAIN VERSION A
<u>MKKTAIAIAVALAGFATVAQAALE</u><u>QVTLKESGPALVKPTQTLTLTCTFS</u>
<u>ompA secretion signal</u>          <u>Hu20C2</u>

<u>GFS</u><u>LSTSGMGV</u><u>GWIRQPPGKALEWLA</u><u>HIWWDDDKSYNPSLKS</u><u>RLTISKD</u>
      CDR1                        CDR2

<u>TSKNQVVLTMTNMDPVDTATYYCAR</u><u>RQLGLRSIDAMDY</u><u>WGQGTTVTVSS</u>
                                CDR3

<u>ASTKGPSVFPLAPSSKSTSGGTAALGCLVKDYFPEPVTVSWNSGALTSG</u>
<u>VHTFPAVLQSSGLYSLSSVVTVPSSSLGTQTYICNVNHKPSNTKVDKRV</u>
<u>EPKSCT</u><u>SGHHHHHH</u><u>GGEQKLISEEDLGG</u>*<u>PFVCEYQGQSSDLPQPPVNA</u>
<u>hCH1</u>  <u>HIS-TAG</u>    <u>MYC-TAG</u>  ◆Amb

<u>GGGSGGGSGGGSEGGGSEGGGSEGGGSEGGGSGGGSGSGDFDYEKMANA</u>
   pIII stump

NKGAMTENADENALQSDAKGKLDSVATDYGAAIDGFIGDVSGLANGNGA
TGDFAGSNSQMAQVGDGDNSPLMNNFRQYLPSLPQSVECRPYVFGAGKP
YEFSIDCDKINLFRGVFAFLLYVATFMYVFSTFANILRNKES* (SEQ
ID NO:116)

*FIG. 4A* pFab4 Hu20C2 HEAVY CHAIN VERSION B

MKKTAIAIAVALAGFATVAQAALE<u>QVTLKESGPALVKPTQTLTLTCTLS</u>
<u>ompA secretion signal</u>    <u>Hu20C2</u>

<u>GFSLSTSGMGVGWIRQPPGKALEWLAHIWWDDDKSYNPSLKSRLTISKD</u>
    CDR1                     CDR2

<u>TSKNQVVLTMTNMDPVDTATYYCARRQLGLRSIDAMDYWGQGTTVTVSA</u>
                                CDR3
STKGPSVFPLAPSSKSTSGGTAALGCLVKDYFPEPVTVSWNSGALTSGV
HTFPAVLQSSGLYSLSSVVTVPSSSLGTQTYICNVNHKPSNTKVDKRVE
PKSCTSGHHHHHHGGEQKLISEEDLGG*PFVCEYQGQSSDLPQPPVNAG
<u>hCH1</u>  <u>HIS-TAG</u>  <u>MYC-TAG</u> ♦Amb

<u>GGSGGGSGGGSEGGGSEGGGSEGGGSEGGGSGGGSGSG</u>DFDYEKMANAN
pIII stump

KGAMTENADENALQSDAKGKLDSVATDYGAAIDGFIGDVSGLANGNGAT
GDFAGSNSQMAQVGDGDNSPLMNNFRQYLPSLPQSVECRPYVFGAGKPY
EFSIDCDKINLFRGVFAFLLYVATFMYVFSTFANILRNKES* (SEQ
ID NO:117)

*FIG. 4B* pFab4 Hu20C2 LIGHT CHAIN

MKYLLPTAAAGLLLLAAQPAMASR*DVVMTQSPLSLPVTPGEPASISCRS*
<u>Pel secretion signal</u>    <u>Hu20C2</u>

*SQSILHSNGNTYLEWYLQKPGQSPQLLIYKVSNRFSGVPDRFSGSGSGT*
    CDR1                     CDR2

*DFTLKISRVEAEDVGVYYCFQGSLVPLTFGQGTKLEIKR*TVAAPSVFIF
                         CDR3

PPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC
              hCK              (SEQ ID NO:118)

*FIG. 4C* pFab4 Hu20C2 HEAVY CHAIN VERSION A/LIGHT CHAIN
GCCCAATACGCAAACCGCCTCTCCCCGCGCGTTGGCCGATTCATTAATGCAGCTGGC
ACGACAGGTTTCCCGACTGGAAAGCGGGCAGTGAGCGCAACGCAATTAATGTGAGTT
AGCTCACTCATTAGGCACCCCAGGCTTTACACTTTATGCTTCCGGCTCGTATGTTGT
GTGGAATTGTGAGCGGATAACAATTTCACACAAGATCTAGCTATTCCAGAGATTACG
CAAATTCTATTTCAAGGAGACAGTCATAATGAAATACCTGCTGCCGACTGCAGCTGC
TGGTCTGCTGCTGCTGGCGGCCCAGCCGGCTATGGCTTCTAGAgatgtggtgatgac
ccagagccccctgtcctgcctgtgaccctggcgagcctgccagcatctcctgccg
gagctcccagagcatcctgcactccaatggcaacacctacctggagtggtacctgca
gaagcctggccagagcccccagctgctgatctacaaggtgtccaaccggttctccgg
cgtgcctgaccggttcagcggctccggcagcggcacagacttcaccctgaagatcag
ccgggtggaggctgaggatgtgggcgtctactactgcttccagggcagcctggtgcc
cctgacctttggccagggcaccaagctggagatcaagCGTACGGTGGCTGCACCATC
TGTCTTCATCTTCCCGCCATCTGATGAGCAGTTGAAATCTGGAACTGCCTCTGTTGT
GTGCCTGCTGAATAACTTCTATCCCAGAGAGGCCAAAGTACAGTGGAAGGTGGATAA
CGCCCTCCAATCGGGTAACTCCCAGGAGAGTGTCACAGAGCAGGACAGCAAGGACAG
CACCTACAGCCTCAGCAGCACCCTGACGCTGAGCAAAGCAGACTACGAGAAACACAA
AGTCTACGCCTGCGAAGTCACCCATCAGGGCCTGAGCTCGCCCGTCACAAAGAGCTT
CAACAGGGGAGAGTGTTAACAATTGCTAGAATTGTGAGCGGATAACAATTTCAGCAG
GTCGAGTTCTTGATAACGAGGCGTAAAAAATGAAAAAGACAGCTATCGCGATTGCAG
TGGCACTGGCTGGTTTCGCTACCGTGGCCCAGGCGGCCCTCGAGcaggtgaccctga
aggagtctggccctgccctggtgaagcccacccagaccctgaccctgacctgcacct
tctctggcttcagcctgagcacctctggcatgggcgtgggctggatccggcagcccc
ctggcaaggccctggagtggctggcccacatctggtgggacgacgacaagtcctaca
acccagcctgaagagccggctgaccatcagcaaggacaccagcaagaaccaggtgg
tgctgaccatgaccaacatggaccctgtggacacagccacctactactgtgcccggc
ggcagctgggcctgcggagcattgatgccatggactactggggccagggcaccacag
tgacagtgtccagcGCCTCCACCAAGGGCCCATCGGTCTTCCCCCTGGCACCCTCCT
CCAAGAGCACCTCTGGGGGCACAGCGGCCCTGGGCTGCCTGGTCAAGGACTACTTCC
CCGAACCGGTGACGGTGTCGTGGAACTCAGGCGCCCTGACCAGCGGCGTGCACACCT
TCCCGGCTGTCCTACAGTCCTCAGGACTCTACTCCCTCAGCAGCGTGGTGACCGTGC
CCTCCAGCAGCTTGGGCACCCAGACCTACATCTGCAACGTGAATCACAAGCCCAGCA
ACACCAAGGTGGACAAGAGAGTTGAGCCCAAATCTTGTACTAGTGGCCACCACCACC
ATCACCATGGCGGTGAACAAAAACTCATCTCAGAAGAGGATCTGGGTGGTTAGCCAT
TCGTTTGTGAATATCAAGGCCAATCGTCTGACCTGCCTCAACCTCCTGTCAATGCTG
GCGGCGGCTCTGGTGGTGGTTCTGGTGGCGGCTCTGAGGGTGGCGGCTCTGAGGGTG
GCGGTTCTGAGGGTGGCGGCTCTGAGGGTGGCGGTTCCGGTGGCGGCTCCGGTTCCG
GTGATTTTGATTATGAAAAAATGGCAAACGCTAATAAGGGGGCTATGACCGAAAATG
CCGATGAAAACGCGCTACAGTCTGACGCTAAAGGCAAACTTGATTCTGTCGCTACTG
ATTACGGTGCTGCTATCGATGGTTTCATTGGTGACGTTTCCGGCCTTGCTAATGGTA
ATGGTGCTACTGGTGATTTTGCTGGCTCTAATTCCCAAATGGCTCAAGTCGGTGACG
GTGATAATTCACCTTTAATGAATAATTTCCGTCAATATTTACCTTCTTTGCCTCAGT
CGGTTGAATGTCGCCCTTATGTCTTTGGCGCTGGTAAACCATATGAATTTTCTATTG
ATTGTGACAAAATAAACTTATTCCGTGGTGTCTTTGCGTTTCTTTTATATGTTGCCA
CCTTTATGTATGTATTTTCGACGTTTGCTAACATACTGCGTAATAAGGAGTCTTAAG
CTAGCTGGCCGTCGTTTTACAACGTCGTGACTGGGAAAACCCTGGCGTTACCCAACT
TAATCGCCTTGCAGCACATCCCCCTTTCGCCAGCTGGCGTAATAGCGAAGAGGCCCG
CACCGATCGCCCTTCCCAACAGTTGCGCAGCCTGAATGGCGAATGGCGATTCCGTTG

*FIG. 4D*

```
CAATGGCTGGCGGTAATATTGTTCTGGATATTACCAGCAAGGCCGATAGTTTGAGTT
CTTCTACTCAGGCAAGTGATGTTATTACTAATCAAAGAAGTATTGCGACAACGGTTA
ATTTGCGTGATGGACAGACTCTTTTACTCGGTGGCCTCACTGATTATAAAACACTT
CTCAGGATTCTGGCGTACCGTTCCTGTCTAAAATCCCTTTAATCGGCCTCCTGTTTA
GCTCCCGCTCTGATTCTAACGAGGAAAGCACGTTATACGTGCTCGTCAAAGCAACCA
TAGTACGCGCCCTGTAGCGGCGCATTAAGCGCGGCGGGTGTGGTGGTTACGCGCAGC
GTGACCGCTACACTTGCCAGCGCCCTAGCGCCCGCTCCTTTCGCTTTCTTCCCTTCC
TTTCTCGCCACGTTCGCCGGCTTTCCCCGTCAAGCTCTAAATCGGGGGCTCCCTTTA
GGGTTCCGATTTAGTGCTTTACGGCACCTCGACCCCAAAAACTTGATTAGGGTGAT
GGTTCACGTAGTGGGCCATCGCCCTGATAGACGGTTTTTCGCCCTTTGACGTTGGAG
TCCACGTTCTTTAATAGTGGACTCTTGTTCCAAACTGGAACAACACTCAACCCTATC
TCGGTCTATTCTTTTGATTTATAAGGGATTTTGCCGATTTCGGCCTATTGGTTAAAA
AATGAGCTGATTTAACAAAAATTTAACGCGAATTTTAACAAAATATTAACGTTTACA
ATTTAAATATTTGCTTATACAATCTTCCTGTTTTTGGGGCTTTTCTGATTATCAACC
GGGGTACATATGATTGACATGCTAGTTTTACGATTACCGTTCATCGCAGGTGGCACT
TTTCGGGGAAATGTGCGCGGAACCCCTATTTGTTTATTTTTCTAAATACATTCAAAT
ATGTATCCGCTCATGAGACAATAACCCTGATAAATGCTTCAATAATATTGAAAAAGG
AAGAGTATGAGTATTCAACATTTCCGTGTCGCCCTTATTCCCTTTTTGCGGCATTT
TGCCTTCCTGTTTTTGCTCACCCAGAAACGCTGGTGAAAGTAAAAGATGCTGAAGAT
CAGTTGGGTGCACGAGTGGGTTACATCGAACTGGATCTCAACAGCGGTAAGATCCTT
GAGAGTTTTCGCCCCGAAGAACGTTTTCCAATGATGAGCACTTTTAAAGTTCTGCTA
TGTGGCGCGGTATTATCCCGTATTGACGCCGGGCAAGAGCAACTCGGTCGCCGCATA
CACTATTCTCAGAATGACTTGGTTGAGTACTCACCAGTCACAGAAAAGCATCTTACG
GATGGCATGACAGTAAGAGAATTATGCAGTGCTGCCATAACCATGAGTGATAACACT
GCGGCCAACTTACTTCTGACAACGATCGGAGGACCGAAGGAGCTAACCGCTTTTTTG
CACAACATGGGGGATCATGTAACTCGCCTTGATCGTTGGGAACCGGAGCTGAATGAA
GCCATACCAAACGACGAGCGTGACACCACGATGCCTGTAGCAATGGCAACAACGTTG
CGCAAACTATTAACTGGCGAACTACTTACTCTAGCTTCCCGGCAACAATTAATAGAC
TGGATGGAGGCGGATAAAGTTGCAGGACCACTTCTGCGCTCGGCCCTTCCGGCTGGC
TGGTTTATTGCTGATAAATCTGGAGCCGGTGAGCGTGGGTCTCGCGGTATCATTGCA
GCACTGGGGCCAGATGGTAAGCCCTCCCGTATCGTAGTTATCTACACGACGGGGAGT
CAGGCAACTATGGATGAACGAAATAGACAGATCGCTGAGATAGGTGCCTCACTGATT
AAGCATTGGTAACTGTCAGACCAAGTTTACTCATATATACTTTAGATTGATTTAAAA
CTTCATTTTTAATTTAAAAGGATCTAGGTGAAGATCCTTTTTGATAATCTCATGACC
AAAATCCCTTAACGTGAGTTTTCGTTCCACTGAGCGTCAGACCCCGTAGAAAAGATC
AAAGGATCTTCTTGAGATCCTTTTTTTCTGCGCGTAATCTGCTGCTTGCAAACAAAA
AAACCACCGCTACCAGCGGTGGTTTGTTTGCCGGATCAAGAGCTACCAACTCTTTTT
CCGAAGGTAACTGGCTTCAGCAGAGCGCAGATACCAAATACTGTCCTTCTAGTGTAG
CCGTAGTTAGGCCACCACTTCAAGAACTCTGTAGCACCGCCTACATACCTCGCTCTG
CTAATCCTGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGGGGGTTCG
TGCACACAGCCCAGCTTGGAGCGAACGACCTACACCGAACTGAGATACCTACAGCGT
GAGCTATGAGAAAGCGCCACGCTTCCCGAAGGGAGAAAGGCGGACAGGTATCCGGTA
AGCGGCAGGGTCGGAACAGGAGAGCGCACGAGGGAGCTTCCAGGGGGAAACGCCTGG
TATCTTTATAGTCCTGTCGGGTTTCGCCACCTCTGACTTGAGCGTCGATTTTTGTGA
TGCTCGTCAGGGGGCGGAGCCTATGGAAAAACGCCAGCAACGCGGCCTTTTTACGG
TTCCTGGCCTTTTGCTGGCCTTTTGCTCACATGTTCTTTCCTGCGTTATCCCCTGAT
TCTGTGGATAACCGTATTACCGCCTTTGAGTGAGCTGATACCGCTCGCCGCAGCCGA
ACGACCGAGCGCAGCGAGTCAGTGAGCGAGGAAGCGGAAGAGC (SEQ ID
NO:119)
```

*FIG. 4E*

```
Biotin-5'-ctatggcttctagaGATGTGGTGATG  (Primer 20C2LC3F; SEQ ID NO:120)
agctgctggtctgctgctggcgggccagccggctatggcttctagaGATGTGGTGATGACCCAGAGCCCCCTGTCCCTGCCTGTGACCCTGGCGAGC
CTGCCAGCATCTCCTGCCGGAGCTCCCAGAGCATCTGCACTCCAAATGCAACACCTACCTGATGTGGTACCTGCAGAAGCCTGACCAGAGCCCCAGCTG
CTGATCTACAAGGTGTCCAACCGGTTCTCCGGCGTCCCTGACCCTGACCCTGACCCTCCGGCACAGACTTCACCCTGAAGATCAGCCGGGTGGAGGC
TGAGGATGTGGGC
                                        F  Q  G  S  L  V  P  L  T  (SEQ ID NO:39)
                      GTCTACTACTGCTTCCAGGGCAGCCTGGTGCCCCTGACCCTTTGGCCAGGCACCAAGCTGGAGATCAAGcgtacggtggctg   (SEQ ID NO:121)
                      GTCTACTACTGCNNKNNKNNKNNKGTGCCCCTGACCCTTTGGCCAGGCACCAAGCTGGAGATCAAGcgtacggtggctg   (SEQ ID NO:122)
                               F  Q  G  S  L  V  P  L  T  (SEQ ID NO:40)
                               X  X  X  X  V  P  L  T  (Primer 20C2LC3-1; SEQ ID NO:123)

Biotin-5'-cagccacccgtacgCTTGATCTCCAGCTTGGTGCCTGGCCAAAGGTCAGGGGCACMNNMNNMNNMNNGCAGTAGTAGAC 82
                                        F  Q  G  S  L  V  P  L  T  (SEQ ID NO:39)
                      GTCTACTACTGCTTCCAGGGCAGCCTGGTGCCCCTGACCCTTTGGCCAGGCACCAAGCTGGAGATCAAGcgtacggtggctg   (SEQ ID NO:121)
                      GTCTACTACTGCTTCCAGGGCAGCNNKNNKNNKNNKTTTGGCCAGGCACCAAGCTGGAGATCAAGcgtacggtggctg   (SEQ ID NO:124)
                               F  Q  G  S  X  X  X  X  X  (Primer 20C2LC3-2; SEQ ID NO:125)

Biotin-5'-cagccacccgtacgCTTGATCTCCAGCTTGGTGCCTGGCCAAAMNNMNNMNNMNNGCTGCCCTGGAAGCAGTAGTAGAC 82
```

FIG. 5A

```
Biotin-5'-gtttatctcgagCAGGTGACCCTGAAG (Primer 20C2HC3F; SEQ ID NO:126)
ccgtgccaggcggccctcgagCAGGTGACCCTGAAGGAGTCTGGCCCTGTGAAGCCCACCCAGACCCTGACCCTGACCTGCACCTTCT
CTGGCTTCAGCCTGAGCACCTCTGGCATGGGCGTGGGCTGGATCCGGCAGCCCCCTGGCAAGGCCCTGGAGTGGCTGGCCCACATCTGGTGGGACG
ACGACAAGTCCTACAACCCCAGCCTGAAGAGCCGGCTGACCATCAGCAAGGACACCAGCAAGAACCAGGTGGTGCTGACCATGACCAACATGGACC
CTGTGGACA
     R   Q   L   G   L   R   S   I   D   A   M   D   Y  (SEQ ID NO:99)
GTGCCCGGCGGCGGCAGCTGGGCCTGCGGAGCATTGATGCCATGGACTACTGGGGCCAGGGCACCACAGTGACAGTGTCCAGCGCCTCCACCAAGGGCCCATCGG
GTGCCCGGCGGCGGCAGCTGGGCCTGCGGAGCATTGATGCCATGGACTACTGGGGCCAGGGCACCACAGTGACAGTGTCCAGCGCCTCCACCAAGGGCCCATCGG
     X   X   X   X   X   X   S   I   D   A   M   D   Y  (SEQ ID NO:100)
Biotin-5'-CCGATGGGCCCTTGGTGGTGCCCTGGACCGCTGGAGGCGCTGACACTGTCACTGTGGTGCCCTGGCCCCAGTAGTCCATGGCATCAATGCTCCGMNNMNNMNNMNNCC
GGGCAC (Primer 20C2HC3-1; SEQ ID NO:129)
     R   Q   L   G   L   R   S   I   D   A   M   D   Y  (SEQ ID NO:99)
GTGCCCGGCGGCGGCAGCTGGGCCTGCGGAGCATTGATGCCATGGACTACTGGGGCCAGGGCACCACAGTGACAGTGTCCAGCGCCTCCACCAAGGGCCCATCGG
GTGCCCGGCGGCGGCAGCTGGGCCTGCGGAGCATTGATTNNKNNKNNKNNKTGGGGCCAGGGCACCACAGTGACAGTGTCCAGCGCCTCCACCAAGGGCCCATCGG
     R   Q   L   G   L   R   S   I   X   X   X   X   X  (SEQ ID NO:101)
Biotin-5'-CCGATGGGCCCTTGGTGGTGCCCTGGCCCCAMNNMNNMNNMNNAATGCTCCGCAGGCCCAGCTG
                                          (Primer 20C2HC3-2; SEQ ID NO:131)
     R   Q   L   G   L   R   S   I   D   A   M   D   Y  (SEQ ID NO:99)
GTGCCCGGCGGCGGCAGCTGGGCCTGCGGAGCATTGATGCCATGGACTACTGGGGCCAGGGCACCACAGTGACAGTGTCCAGCGCCTCCACCAAGGGCCCATCGG
GTGCCCGGCGGCGGCAGCTGGGCCNNKNNKNNKNNKGCCATGGACTACTGGGGCCAGGGCACCACAGTGACAGTGTCCAGCGCCTCCACCAAGGGCCCATCGG
     R   Q   L   G   X   X   X   X   A   M   D   Y  (SEQ ID NO:102)
Biotin-5'-CCGATGGGCCCTTGGTGGTGCCCTGGCCCCAGTAGTCCATGGCCMNNMNNMNNMNNMNNGCCCAGCTG
                                               (Primer 20C2HC3-3; SEQ ID NO:133)
```

FIG. 5B

```
            |--- CH1 STARTS HERE        C144
IgG1    /// ASTK GPSVFPLAPS SKSTSGGTAA LGCLVKDYFP EPVTVSWNSG
IgG2    /// ASTK GPSVFPLAPC SRSTSESTAA LGCLVKDYFP EPVTVSWNSG
IgG4    /// ASTK GPSVFPLAPC SRSTSESTAA LGCLVKDYFP EPVTVSWNSG
IgG2M4  /// ASTK GPSVFPLAPC SRSTSESTAA LGCLVKDYFP EPVTVSWNSG
        (VH-C1 LINKER)
                                                C200
IgG1    ALTSGVHTFP AVLQSSGLYS LSSVVTVPSS SLGTQTYICN VNHKPSNTKV
IgG2    ALTSGVHTFP AVLQSSGLYS LSSVVTVTSS NFGTQTYTCN VDHKPSNTKV
IgG4    ALTSGVHTFP AVLQSSGLYS LSSVVTVPSS SLGTKTYTCN VDHKPSNTKV
IgG2M4  ALTSGVHTFP AVLQSSGLYS LSSVVTVTSS NFGTQTYTCN VDHKPSNTKV

-HINGE REGION--||----CH2-> P238         M252    C261
IgG1    DKKAEPKSCD KTHTCPPCPA PELLGGPSVF LFPPKPKDTL MISRTPEVTC
IgG2    DKTVERKCC- --VECPPCPA PP-VAGPSVF LFPPKPKDTL MISRTPEVTC
IgG4    DKRVESKYGP ---PCPSCPA PEFLGGPSVF LFPPKPKDTL MISRTPEVTC
IgG2M4  DKTVERKCC- --VECPPCPA PP-VAGPSVF LFPPKPKDTL MISRTPEVTC
                           (LOWER HINGE)        FcRn-BIND

Q268                        N297*       L309
IgG1    VVVDVSHEDP EVKFNWYVDG VEVHNAKTKP REEQYNSTYR VVSVLTVLHQ
IgG2    VVVDVSHEDP EVQFNWYVDG VEVHNAKTKP REEQFNSTFR VVSVLTVVHQ
IgG4    VVVDVSQEDP EVQFNWYVDG VEVHNAKTKP REEQFNSTYR VVSVLTVLHQ
IgG2M4  VVVDVSQEDP EVQFNWYVDG VEVHNAKTKP REEQFNSTFR VVSVLTVLHQ
        B/C LOOP                       C'E LOOP   FcRn-BIND
                         P331
            C321     A330       |----CH3->
IgG1    DWLNGKEYKC KVSNKALPAPI EKTISKAKG QPREPQVYTL PPSRDELTKN
IgG2    DWLNGKEYKC KVSNKGLPAPI EKTISKTKG QPREPQVYTL PPSREEMTKN
IgG4    DWLNGKEYKC KVSNKGLPSSI EKTISKAKG QPREPQVYTL PPSQEEMTKN
IgG2M4  DWLNGKEYKC KVSNKGLPSSI EKTISKTKG QPREPQVYTL PPSREEMTKN
                         F/G LOOP

IgG1    QVSLTCLVKG FYPSDIAVEW ESNGQPENNY KTTPPVLDSD GSFFLYSKLT
IgG2    QVSLTCLVKG FYPSDIAVEW ESNGQPENNY KTTPPMLDSD GSFFLYSKLT
IgG4    QVSLTCLVKG FYPSDIAVEW ESNGQPENNY KTTPPVLDSD GSFFLYSRLT
IgG2M4  QVSLTCLVKG FYPSDIAVEW ESNGQPENNY KTTPPMLDSD GSFFLYSKLT

M428L H433
IgG1    VDKSRWQQGN VFSCSVMHEA LHNHYTQKSL SLSPGK* (SEQ ID NO:134)
IgG2    VDKSRWQQGN VFSCSVMHEA LHNHYTQKSL SLSPGK* (SEQ ID NO:135)
IgG4    VDKSRWQEGN VFSCSVMHEA LHNHYTQKSL SLSLGK* (SEQ ID NO:136)
IgG2M4  VDKSRWQQGN VFSCSVMHEA LHNHYTQKSL SLSPGK* (SEQ ID NO:137)
                              FcRn-BIND
```

FIG. 6

HUMANIZED Hu20C2A3 IgG2M4 - HEAVY CHAIN
```
  1 QVTLKESGPG LLKPTQTLTL TCTLSGFSLS TSGMGVGWFR QPPGKGLEWL
 51 AHIWWDDDKS YNPSLKSRLT ISKDTSKNQV VLTITNVDPV DTATYYCARR
101 QLGTRGTDAM DYWGQGTTVT VSSASTKGPS VFPLAPCSRS TSESTAALGC
151 LVKDYFPEPV TVSWNSGALT SGVHTFPAVL QSSGLYSLSS VVTVTSSNFG
201 TQTYTCNVDH KPSNTKVDKT VERKCCVECP PCPAPPVAGP SVFLFPPKPK
251 DTLMISRTPE VTCVVVDVSQ EDPEVQFNWY VDGVEVHNAK TKPREEQFNS
301 TFRVVSVLTV LHQDWLNGKE YKCKVSNKGL PSSIEKTISK TKGQPREPQV
351 YTLPPSREEM TKNQVSLTCL VKGFYPSDIA VEWESNGQPE NNYKTTPPML
401 DSDGSFFLYS KLTVDKSRWQ QGNVFSCSVM HEALHNHYTQ KSLSLSPGK
```
(SEQ ID NO:138)

FIG. 7A

HUMANIZED Hu20C2A3 IgG2M4 - HEAVY CHAIN
```
ATGGAATGGAGCTGGGTCTTTCTCTTCTTCCTGTCAGTAACTACAGGTGT
CCACTCGCAGGTGACCCTGAAGGAGTCTGGCCCTGGCCTGCTGAAGCCCA
CCCAGACCCTGACCCTGACCTGCACCCTGTCTGGCTTCAGCCTGAGCACC
TCTGGCATGGGCGTGGGCTGGTTCCGGCAGCCCCCTGGCAAGGGCCTGGA
GTGGCTGGCCCACATCTGGTGGGACGACGACAAGTCCTACAACCCCAGCC
TGAAGAGCCGGCTGACCATCAGCAAGGACACCAGCAAGAACCAGGTGGTG
CTGACCATCACCAACGTGGACCCTGTGGACACAGCCACCTACTACTGTGC
CCGGCGGCAGCTGGGCACTAGGGGACGGATGCCATGGACTACTGGGGCC
AGGGCACCACAGTGACAGTGTCCAGCGCATCCACCAAGGGCCCATCCGTC
TTCCCCCTGGCGCCCTGCTCCAGGAGCACCTCCGAGAGCACAGCCGCCCT
GGGCTGCCTGGTCAAGGACTACTTCCCCGAACCGGTGACGGTGTCGTGGA
ACTCAGGCGCCCTGACCAGCGGCGTGCACACCTTCCCGGCTGTCCTACAG
TCCTCAGGACTCTACTCCCTCAGCAGCGTGGTGACCGTGACCTCCAGCAA
CTTTGGCACGCAGACCTACACCTGCAACGTAGATCACAAGCCCAGCAACA
CCAAGGTGGACAAGACAGTTGAGCGGAAATGCTGCGTGGAGTGCCCACCA
TGCCCAGCACCTCCAGTGGCCGGACCATCAGTCTTCCTGTTCCCCCCAAA
ACCCAAGGACACTCTCATGATCTCCCGGACCCCTGAGGTCACGTGCGTGG
TGGTGGACGTGAGCCAGGAAGACCCCGAGGTCCAGTTCAACTGGTACGTG
GATGGCGTGGAGGTGCATAATGCCAAGACAAAGCCGCGGGAGGAGCAGTT
CAACAGCACGTTCCGTGTGGTCAGCGTCCTCACCGTCCTGCACCAGGACT
GGCTGAACGGCAAGGAGTACAAGTGCAAGGTCTCCAACAAAGGCCTCCCG
TCCTCCATCGAGAAAACCATCTCCAAAACCAAAGGGCAGCCCCGAGAGCC
ACAGGTGTACACCCTGCCCCCATCCCGGGAGGAGATGACCAAGAACCAGG
TCAGCCTGACCTGCCTGGTCAAAGGCTTCTACCCCAGCGACATCGCCGTG
GAGTGGGAGAGCAATGGGCAGCCGGAGAACAACTACAAGACCACGCCTCC
CATGCTGGACTCCGACGGCTCCTTCTTCCTCTACAGCAAGCTAACCGTGG
ACAAGAGCAGGTGGCAGCAGGGGAATGTCTTCTCATGCTCCGTGATGCAT
GAGGCTCTGCACAACCACTACACACAGAAGAGCCTCTCCCTGTCTCCTGG
TAAATGA (SEQ ID NO:139)
```

FIG. 7B

HUMANIZED Hu20C2A3  - LIGHT CHAIN

1 DVVMTQTPLS LPVTPGQPAS ISCRSSQSIL HSNGNTYLEW YLQKPGQSPQ
 51 LLIYKVSNRF SGVPDRFSGS GSGTDFTLKI SRVEAEDVGV YYCLQTTRVP
101 LTFGQGTKLE IKRTVAAPSV FIFPPSDEQL KSGTASVVCL LNNFYPREAK
151 VQWKVDNALQ SGNSQESVTE QDSKDSTYSL SSTLTLSKAD YEKHKVYACE
201 VTHQGLSSPV TKSFNRGEC    (SEQ ID NO:140)

FIG. 7C

HUMANIZED Hu20C2A3  - LIGHT CHAIN
ATGAGTGTGCCCACTCAGGTCCTGGGGTTGCTGCTGCTGTGGCTTACAGA
TGCCAGATGCGATGTGGTGATGACCCAGACCCCCCTGTCCCTGCCTGTGA
CCCCTGGCCAGCCTGCCAGCATCTCCTGCCGGAGCTCCCAGAGCATCCTG
CACTCCAATGGCAACACCTACCTGGAGTGGTACCTGCAGAAGCCTGGCCA
GAGCCCCCAGCTGCTGATCTACAAGGTGTCCAACCGGTTCTCCGGCGTGC
CTGACCGGTTCAGCGGCTCCGGCAGCGGCACAGACTTCACCCTGAAGATC
AGCCGGGTGGAGGCTGAGGATGTGGGCGTCTACTACTGCCTTCAGACTAC
TCGTGTGCCCCTGACCTTTGGCCAGGGCACCAAGCTGGAGATCAAGCGTA
CGGTGGCTGCACCATCTGTCTTCATCTTCCCGCCATCTGATGAGCAGTTG
AAATCTGGAACTGCCTCTGTTGTGTGCCTGCTGAATAACTTCTATCCCAG
AGAGGCCAAAGTACAGTGGAAGGTGGATAACGCCCTCCAATCGGGTAACT
CCCAGGAGAGTGTCACAGAGCAGGACAGCAAGGACAGCACCTACAGCCTC
AGCAGCACCCTGACGCTGAGCAAAGCAGACTACGAGAAACACAAAGTCTA
CGCCTGCGAAGTCACCCATCAGGGCCTGAGCTCGCCCGTCACAAAGAGCT
TCAACAGGGGAGAGTGTTAG (SEQ ID NO:141)

FIG. 7D

ANTI-ADDL MONOCLONAL ANTIBODY AND USE THEREOF

INTRODUCTION

This application is a continuation of U.S. patent application Ser. No. 11/581,843 filed Oct. 17, 2006 now U.S. Pat. No. 7,731,962, which is a continuation-in-part of U.S. patent application Ser. No. 11/256,332, filed Oct. 21, 2005 now U.S. Pat No. 7,780,963, which claims the benefit of priority from U.S. provisional patent application Ser. No. 60/652,538, filed Feb. 14, 2005, whose contents are incorporated herein by reference in their entireties.

BACKGROUND OF THE INVENTION

Alzheimer's Disease is a progressive and degenerative dementia (Terry, et al. (1991) *Ann. Neurol.* 30:572-580; Coyle (1987) In: *Encyclopedia of Neuroscience*, Adelman (ed.), Birkhäuser, Boston-Basel-Stuttgart, pp 29-31). In its early stages, Alzheimer's Disease manifests primarily as a profound inability to form new memories (Selkoe (2002) *Science* 298:789-791), reportedly due to neurotoxins derived from amyloid beta (Aβ). Aβ is an amphipathic peptide whose abundance is increased by mutations and risk factors linked to Alzheimer's Disease. Fibrils formed from Aβ constitute the core of amyloid plaques, which are hallmarks of an Alzheimer's Disease brain. Analogous fibrils generated in vitro are lethal to cultured brain neurons. These findings indicate that memory loss is a consequence of neuron death caused by fibrillar Aβ.

Despite strong experimental support for fibrillar Aβ and memory loss, a poor correlation exists between dementia and amyloid plaque burden (Katzman (1988) *Ann. Neurol.* 23:138-144). Moreover, transgenic hAPP mice (Dodart, et al. (2002) *Nat. Neurosci.* 5:452-457; Kotilinek, et al. (2002) *J. Neurosci.* 22:6331-6335), which develop age-dependent amyloid plaques and, most importantly, age-dependent memory dysfunction, show that within 24 hours of vaccination with monoclonal antibodies against Aβ memory loss can be reversed with no change in plaque levels. Such findings are not consistent with a mechanism for memory loss dependent on neuron death caused by amyloid fibrils.

Additional neurologically active molecules formed by Aβ self-assembly have been suggested. These molecules include soluble Aβ oligomers, also referred to as Aβ-derived diffusible ligands or ADDLs. Oligomers are metastable and form at low concentrations of Aβ1-42 (Lambert, et al. (1998) *Proc. Natl. Acad. Sci. USA* 95:6448-6453). Aβ oligomers rapidly inhibit long-term potentiation (LTP), a classic experimental paradigm for memory and synaptic plasticity. As such, memory loss stems from synapse failure, prior to neuron death and synapse failure by Aβ oligomers, not fibrils (Hardy & Selkoe (2002) *Science* 297:353-356). Soluble oligomers have been found in brain tissue and are strikingly elevated in Alzheimer's Disease (Kayed, et al. (2003) *Science* 300:486-489; Gong, et al. (2003) *Proc. Natl. Acad. Sci. USA* 100:10417-10422) and in hAPP transgenic mice Alzheimer's Disease models (Kotilinek, et al. (2002) *J. Neurosci.* 22:6331-6335; Chang, et al. (2003) *J. Mol. Neurosci.* 20:305-313).

A variety of Alzheimer's Disease treatment options have been suggested. Vaccine clinical trials have revealed that persons mounting a vigorous immune response to the vaccine exhibit cognitive benefit (Hock, et al. (2003) *Neuron* 38:547-554); however, frequency of CNS inflammation caused early termination of part of the trial (Birmingham & Frantz (2002) *Nat. Med.* 8:199-200). As an alternative to a vaccine, therapeutic antibodies that target ADDLs without binding monomers or fibrils have been suggested (Klein (2002) *Neurochem. Int.* 41:345-352). ADDLs are highly antigenic, generating oligomer-selective polyclonal antibodies in rabbits at concentration of ~50 µg/mL (Lambert, et al. (2001) *J. Neurochem.* 79:595-605). Results from transgenic mice models also suggest that antibodies can be successful in reversing memory decline (Dodart, et al. (2002) *Nat. Neurosci.* 5:452-457; U.S. patent application Ser. No. 11/194,989). Accordingly, there is a need in the art for ADDL-selective therapeutic antibodies for the prevention and treatment of Alzheimer's Disease. The present invention meets this need.

SUMMARY OF THE INVENTION

The present invention is an isolated antibody, or fragment thereof, capable of differentially recognizing a multi-dimensional conformation of one or more Aβ-derived diffusible ligands. In particular, the antibody of the instant invention has a complementary determining region (CDR) of Arg-$Xaa_1$-Leu-$Xaa_2$-$Xaa_3$-$Xaa_4$-$Xaa_5$-$Xaa_6$-Asp-Ala-Met-Asp-Tyr (SEQ ID NO:9), wherein $Xaa_1$ is Gln or Ala; $Xaa_2$ is Ser or Gly; $Xaa_3$ is Pro, Ala, Lys, Arg, or Thr; $Xaa_4$ is Lys or Arg; $Xaa_5$ is Gly, Ser, or Lys; $Xaa_6$ is Val, Thr, Ile or Arg. In particular embodiments, the antibody of the present invention is in admixture with a pharmaceutically acceptable carrier. In other embodiments, the antibody of the present invention is in a kit. Still other embodiments embrace an antibody having heavy and light chain variable region sequences as set forth in SEQ ID NO:108 and SEQ ID NO:112. An antibody having heavy and light chain sequences as set forth in SEQ ID NO:138 and SEQ ID NO:140 is also provided.

Methods for preventing binding of Aβ-derived diffusible ligands to a neuron and inhibiting assembly of Aβ-derived diffusible ligands employing an antibody or antibody fragment which binds a multi-dimensional conformation of one or more Aβ-derived diffusible ligands are also provided.

The present invention further embraces a method for prophylactically or therapeutically treating a disease associated with Aβ-derived diffusible ligands using an antibody of the instant invention. Administration of an antibody of the invention can prevent binding of Aβ-derived diffusible ligands to a neuron thereby preventing or treating the disease associated with Aβ-derived diffusible ligands.

The present invention is also a method for identifying a therapeutic agent that prevents the binding of Aβ-derived diffusible ligands to a neuron. This method of the invention involves contacting a neuron with Aβ-derived diffusible ligands in the presence of an agent and using an antibody of the present invention to determine binding of the Aβ-derived diffusible ligands to the neuron in the presence of the agent.

The present invention also embraces a method for detecting Aβ-derived diffusible ligands in a sample and a method for diagnosing a disease associated with Aβ-derived diffusible ligands. Such methods involve contacting a sample with an antibody of the instant invention so that the Aβ-derived diffusible ligands can be detected and a disease associated with Aβ-derived diffusible ligands can be diagnosed.

BRIEF DESCRIPTION OF THE DRAWINGS

FIG. 1 shows the nucleic acid sequences for the heavy (FIG. 1A) and light (FIG. 1B) chain variable regions for murine anti-ADDL antibody 20C2. Lower case letters indicate the antibody leader sequences and uppercase letters indicate antibody variable region sequences. The nucleotides coding for the complementary determining regions (CDRs) are underlined.

FIG. 2 shows comparisons of heavy (FIG. 2A) and light (FIG. 2B) chain variable region amino acid sequences of murine antibody 20C2 and humanized antibodies, Hu20C2 (CDR grafted) and Hu20C2A3 (veneered). Sequences are presented as comparisons between the 20C2 mouse sequence, the most homologous human genomic sequence and the humanized sequences. Sequence differences in the frame regions between murine 20C2 and humanized Hu20C2A3 are in bold. Sequence differences in the underlined CDR regions between humanized Hu20C2A3 and murine 20C2 are in bold and indicated with an *. CDRs are underlined.

FIG. 3 shows nucleic acid sequences for the heavy (FIGS. 3A and 3B) and light (FIG. 3C) chain variable regions (HCVRs and LCVRs, respectively) for humanized anti-ADDL antibody Hu20C2 (CDR grafted). Two humanized versions of the Hu20C2 heavy chain were generated (HCVRA and HCVRB) that differ by one amino acid at position 24. In Hu20C2 HCVRA the human amino acid was used and in Hu20C2 HCVRB the mouse amino acid was used. Variable region sequences were cloned into full heavy and light chain antibody expression vectors.

FIG. 4 shows the annotated amino acid sequences and nucleotide sequences of Hu20C2 humanized antibody in Fab phage-display vector pFab4. Amino acid sequence for heavy chain version A (FIG. 4A), heavy chain version B (FIG. 4B), and the light chain (FIG. 4C) of Hu20C2 humanized antibody in Fab phage-display vector pFab4 are in italic and underlined regions are as indicated. Nucleotide sequence of heavy chain version A fused with the light chain of Hu20C2 in pFab4 vector is shown in FIG. 4D-4E with sequences encoding the Hu20C2 antibody sequences shown in lowercase.

FIG. 5 depicts the design and primers employed in preparing two light chain CDR3 libraries, namely LC3-1 and LC3-2 (FIG. 5A), and three heavy chain CDR3 libraries, namely 20C2B-39HC$_3$-1, 20C2B-39HC$_3$-2, and 20C2B-39HC$_3$-3 (FIG. 5B), for respectively generating affinity matured Hu20C2 light and heavy chain CDR3s. Restriction endonuclease recognition sites used for cloning are indicated in italic. Uppercase indicates nucleic acids encoding antibody variable region sequences. Nucleic acids encoding CDRs are underlined. Biotin-labeled primers are indicated.

FIG. 6 shows a comparison of the amino acid sequence of human antibody constant regions and the sequence of IgG2m4. The asterisk indicates a glycosylation site at Asn297. Regions of FcRn binding are indicated. Sequences in which IgG2m4 is different from IgG2 are underlined.

FIG. 7 shows the amino acid (FIGS. 7A and 7C) and nucleotide (FIGS. 7B and 7D) sequences for the full IgG2m4 humanized heavy chain (FIGS. 7A and 7B) and humanized Kappa light chain (FIGS. 7C and 7D) for anti-ADDL antibody Hu20C2A3. Underlining indicates variable region sequences. The remaining sequences are constant region sequences.

DETAILED DESCRIPTION OF THE INVENTION

Figure 8A:
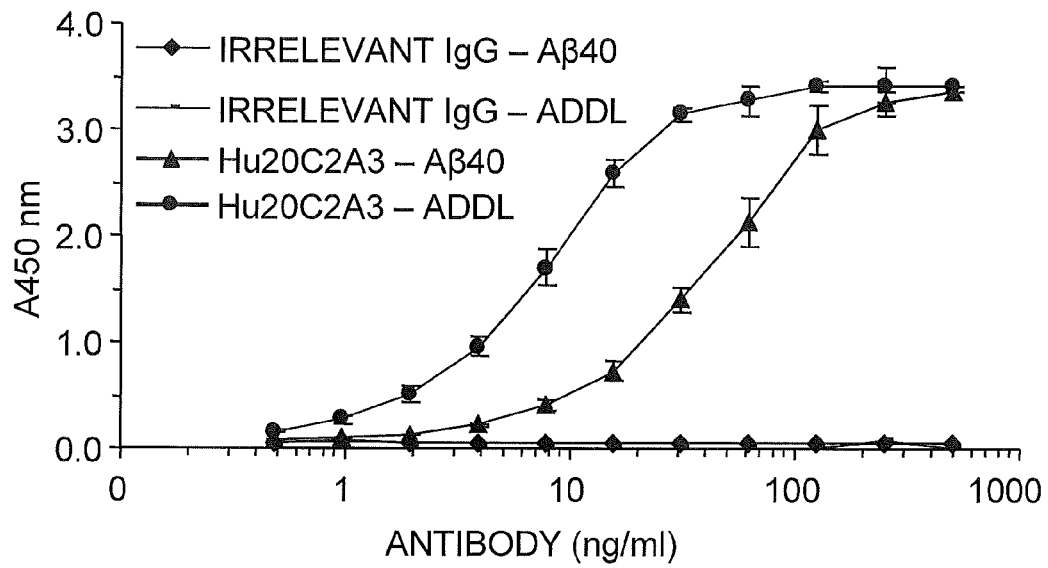
FIG. 8 shows interactions between Aβ40 monomer or ADDLs with Hu20C2A3 produced by two different systems, CHO (FIG. 8A) or *Pichia* (FIG. 8B), as determined by ELISA.

Monoclonal antibodies, which differentially recognize multi-dimensional conformations of Aβ-derived diffusible ligands (i.e., ADDLs), have now been generated. Antibodies of this invention are derived from the murine monoclonal antibody 20C2. Murine 20C2 is known in the art for exhibiting the following characteristics. Murine 20C2 is an IgG1 antibody which binds to both synthetic and endogenous ADDLs bound to cultured hippocampal cells. Furthermore, this antibody can block both endogenous and synthetic ADDL binding to cultured cells, abate the binding of biotinylated ADDLs (bADDLs) to neurons, and prevent tau phosphorylation. The core linear epitope for 20C2 is Glu-Phe-Arg-His-Asp-Ser (SEQ ID NO:1), corresponding to amino acid residues 3-8 of Aβ1-42, with a conformational epitope that is dependent upon elements from within residues 17-42 of Aβ, but only when assembled.

The instant antibodies are humanized and, in some embodiments affinity-matured derivatives of murine 20C2. Like the murine 20C2 antibody, the antibodies disclosed herein exhibit a high degree of selectivity for multi-dimensional conformations of ADDLs, with minimal detection of monomer Aβ peptides. Advantageously, the instant antibodies identify endogenous oligomers in Alzheimer's Disease brain slices and inhibit binding of bADDLs to neurons. Moreover, the instant antibodies provide a significant and robust increase in plasma Aβx-40 levels, an increase in which is known to be associated with an ultimate lowering of brain Aβ. Accordingly, the antibodies of this invention find use in the prevention of ADDL binding to neurons and assembly of ADDLs and the treatment of ADDL-related diseases including Alzheimer's Disease.

Accordingly, the present invention is an isolated antibody that differentially recognizes one or more multi-dimensional conformations of ADDLs. An antibody of the instant invention is said to be isolated when it is present in the substantial absence of other biological macromolecules of the same type. Thus, an "isolated antibody" refers to an antibody which is substantially free of other antibodies; however, the molecule may include some additional agents or moieties which do not deleteriously affect the basic characteristics of the antibody (e.g., binding specificity, neutralizing activity, etc.).

An antibody which is capable of specifically binding one or more multi-dimensional conformations of ADDLs, binds particular ADDLs derived from the oligomerization of Aβ1-42, but like murine 20C2 does not cross-react with other Aβ peptides, namely Aβ1-12, Aβ1-28, Aβ1-40, and Aβ12-28 as determined by western blot analyses; and preferentially bind ADDLs in solution. Specific binding between two entities generally refers to an affinity of at least $10^6$, $10^7$, $10^8$, $10^9$, or $10^{10}$ M$^{-1}$. Affinities greater than $10^8$ M$^{-1}$ are desired to achieve specific binding.

In particular embodiments, an antibody that is capable of specifically binding a multi-dimensional conformation of one or more ADDLs is also raised against (i.e., an animal is immunized with) multi-dimensional conformations of ADDLs. In other embodiments, an antibody that is capable of specifically binding a multi-dimensional conformation of one or more ADDLs is raised against a low n-mer-forming peptide such as Aβ-42[Nle35-Dpro37].

The term "epitope" refers to a site on an antigen to which B and/or T cells respond or a site on a molecule against which an antibody will be produced and/or to which an antibody will bind. For example, an epitope can be recognized by an antibody defining the epitope.

A linear epitope is an epitope wherein an amino acid primary sequence comprises the epitope recognized. A linear epitope typically includes at least 3, and more usually, at least 5, for example, about 6 to about 10 amino acids in a unique sequence.

A conformational epitope, in contrast to a linear epitope, is an epitope wherein the primary sequence of the amino acids comprising the epitope is not the sole defining component of the epitope recognized (e.g., an epitope wherein the primary sequence of amino acids is not necessarily recognized by the antibody defining the epitope). Typically a conformational epitope encompasses an increased number of amino acids relative to a linear epitope. With regard to recognition of conformational epitopes, the antibody recognizes a three-dimensional structure of the peptide or protein. For example, when a protein molecule folds to form a three-dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology (1996) Vol. 66, Morris (Ed.).

Aβ-derived diffusible ligands or ADDLs refer to soluble oligomers of amyloid β1-42 which are desirably composed of aggregates of less than eight or nine amyloid β1-42 peptides and are found associated with Alzheimer's Disease. This is in contrast to high molecular weight aggregation intermediates, which form stings of micelles leading to fibril formation.

As exemplified herein, the instant antibody binds or recognizes at least one multi-dimensional conformation of an ADDL. In particular embodiments, the instant antibody binds at least two, at least three, or at least four multi-dimensional conformations of an ADDL. Multi-dimensional conformations of ADDLs are intended to encompass dimers, trimers, tetramers pentamers, hexamers, heptamers, octamers, nonamers, decamers, etc. as defined by analysis via SDS-PAGE. Because trimer, tetramer, etc. designations can vary with the assay method employed (see, e.g., Bitan, et al. (2005) *Amyloid* 12:88-95) the definition of trimer, tetramer, and the like, as used herein, is according to SDS-PAGE analysis. As such, the antibody of the instant invention has oligomer-specific characteristics. In particular embodiments, a multi-dimensional conformation of an ADDL is associated with a specific polypeptide structure which results in a conformational epitope that is recognized by an antibody of the present invention. In other embodiments, an antibody of the invention specifically binds a multi-dimensional conformation ADDL having a size range of approximately a trimer or tetramer, which have molecular weights in excess of >50 kDa.

In certain embodiments, in addition to binding to a multi-dimensional conformation, the instant antibody binds to a selected linear epitope of amyloid β1-42. A linear epitope of an ADDLs is intended as a four, five, six or more amino acid residue peptide located in the N-terminal 10, 11, 12, 15 or 20 amino acid residues of amyloid β1-42. In particular embodiments, an antibody of the invention specifically binds to a linear epitope within residues 1-10, 1-8, 3-10, or 3-8 of amyloid β1-42. An exemplary linear epitope of amyloid β1-42 which is bound by a humanized antibody of the invention is amino acid residues Glu-Phe-Arg-His-Asp-Ser (SEQ ID NO:1).

While antibodies of the instant invention may have similar linear epitopes, such linear epitopes are not wholly indicative of the binding characteristics of the instant antibodies (i.e., ability to block ADDL binding to neurons, prevent tau phosphorylation and inhibit ADDL assembly) because, as is well-known to the skilled artisan, the linear epitope may only correspond to a portion of the antigen's epitope (see, e.g., Breitling and Dübel (1999) In: Recombinant Antibodies, John Wiley & Sons, Inc., NY, pg. 115). For example, murine 20C2 is known to bind assemblies of charge-inverted, truncated Aβ7-42 peptide, which lack the linear epitope for 20C2 (i.e., amino acid residues 3-8) and contain a very different sequence corresponding to residues 7-16 of Aβ. Therefore, 20C2, as well as humanized derivatives thereof, bind to conformational epitopes that depend upon elements from within residues 17-42 of Aβ, but only when in a multidimensional conformation. The antibody of the instant invention can be distinguished from those of the art as being capable of differentially recognizing multi-dimensional ADDLs and accordingly differentially blocking ADDL binding to neurons, differentially preventing tau phosphorylation and differentially inhibiting ADDL assembly.

An antibody, as used in accordance with the instant invention includes, but is not be limited to, monoclonal antibodies, and chimeric, human (e.g. isolated from B cells), humanized, neutralizing, bispecific or single chain antibodies thereof. In one embodiment, an antibody of the instant invention is monoclonal. For the production of antibodies, various hosts including goats, rabbits, chickens, rats, mice, humans, and others, can be immunized by injection with synthetic or natural ADDLs. Methods for producing antibodies are well-known in the art. See, e.g., Kohler and Milstein ((1975) *Nature* 256:495-497) and Harlow and Lane (Antibodies: A Laboratory Manual (Cold Spring Harbor Laboratory, New York (1988)).

Depending on the host species, various adjuvants can be used to increase the immunological response. Adjuvants used in accordance with the instant invention desirably augment the intrinsic response to ADDLs without causing conformational changes in the immunogen that affect the qualitative form of the response. Particularly suitable adjuvants include 3 De-O-acylated monophosphoryl lipid A (MPL™; RIBI ImmunoChem Research Inc., Hamilton, Mont.; see GB 2220211) and oil-in-water emulsions, such as squalene or peanut oil, optionally in combination with immune stimulants, such as monophosphoryl lipid A (see Stoute, et al. (1997) *N. Engl. J. Med.* 336:86-91), muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl -L-alanyl-D-isoglutaminyl-L-alanine-2-(1'-2'dipalmitoyl-sn-glycero-3-hydroxyphosphoryloxy)-ethylamine (E-PE), N-acetylglucsaminyl-N-acetylmuramyl-L-Al-D-isoglu-L-Ala-dipalmitoxy propylamide (DTP-DPP)), or other bacterial cell wall components. Specific examples of oil-in-water emulsions include MF59 (WO 90/14837), containing 5% Squalene, 0.5% TWEEN™ 80, and 0.5% SPAN 85 (optionally containing various amounts of MTP-PE) formulated into submicron particles using a microfluidizer such as Model 110Y microfluidizer (Microfluidics, Newton, Mass.); SAF containing 10% Squalene, 0.4% TWEEN™ 80, 5% PLURONIC®-blocked polymer L121, and thr-MDP, either microfluidized into a submicron emulsion or vortexed to generate a larger particle size emulsion; and RIBI™ adjuvant system (RAS) (Ribi ImmunoChem, Hamilton, Mont.) containing 2% squalene, 0.2% TWEEN™ 80, and one or more bacterial cell wall components such as monophosphoryllipid A, trehalose dimycolate (TDM), and cell wall skeleton (CWS).

Another class of adjuvants is saponin adjuvants, including ISCOMs (immunostimulating complexes) and ISCOMATRIX® (CSL Ltd., Parkville, Australia). Other suitable adjuvants include Complete Freund's Adjuvant (CFA), Incomplete Freund's Adjuvant (IFA), mineral gels such as aluminum hydroxide, and surface-active substances such as lysolecithin, PLURONIC® polyols, polyanions, peptides, CpG (WO 98/40100), keyhole limpet hemocyanin, dinitrophenol, and cytokines such as interleukins (IL-1, IL-2, and IL-12), macrophage colony stimulating factor (M-CSF), and tumor necrosis factor (TNF). Among adjuvants used in humans, BCG (bacilli Calmette-Guerin) and *Corynebacterium parvum* are particularly suitable.

An antibody to a multi-dimensional conformation ADDL is generated by immunizing an animal with ADDLs. Generally, ADDLs can be generated synthetically or by recombinant fragment expression and purification. Synthetic ADDLs can be prepared as disclosed herein or in accordance with the methods disclosed in U.S. Pat. No. 6,218,506 or in co-pending applications U.S. Ser. Nos. 60/621,776, 60/652,538, 60/695,528 and 60/695,526. Further, ADDLs can be fused with another protein such as keyhole limpet hemocyanin to generate an antibody against the chimeric molecule. The ADDLs can be conformationally constrained to form an epitope useful as described herein and furthermore can be associated with a surface for example, physically attached or chemically bonded to a surface in such a manner so as to allow for the production of a conformation which is recognized by the antibodies of the present invention.

Monoclonal antibodies to multi-dimensional conformations of ADDLs can be prepared using any technique which provides for the production of antibody molecules by continuous cell lines in culture. These include, but are not limited to, the hybridoma technique, the human B-cell hybridoma technique, and the EBV-hybridoma technique (Kohler, et al. (1975) *Nature* 256:495-497; Kozbor, et al. (1985) *J. Immunol. Methods* 81:31-42; Cote, et al. (1983) *Proc. Natl. Acad. Sci.* 80:2026-2030; Cole, et al. (1984) *Mol. Cell. Biol.* 62:109-120).

In particular embodiments, the instant antibodies are humanized. Humanized or chimeric antibodies can be produced by splicing of mouse antibody genes to human antibody genes to obtain a molecule with appropriate antigen specificity and biological activity (see Morrison, et al. (1984) *Proc. Natl. Acad. Sci.* 81, 6851-6855; Neuberger, et al. (1984) *Nature* 312:604-608; Takeda, et al. (1985) *Nature* 314:452-454; Queen, et al. (1989) *Proc. Natl. Acad. Sci. USA* 86:10029-10033; WO 90/07861). For example, a mouse antibody is expressed as the Fv or Fab fragment in a phage selection vector. The gene for the light chain (and in a parallel experiment, the gene for the heavy chain) is exchanged for a library of human antibody genes. Phage antibodies, which still bind the antigen, are then identified. This method, commonly known as chain shuffling, provided humanized antibodies that should bind the same epitope as the mouse antibody from which it descends (Jespers, et al. (1994) *Biotechnology NY* 12:899-903). As an alternative, chain shuffling can be performed at the protein level (see, Figini, et al. (1994) *J. Mol. Biol.* 239:68-78).

Human antibodies can also be obtained using phage-display methods. See, e.g., WO 91/17271 and WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment to ADDLs. Human antibodies against ADDLs can also be produced from non-human transgenic mammals having transgenes encoding at least a segment of the human immunoglobulin locus and an inactivated endogenous immunoglobulin locus. See, e.g., WO 93/12227 and WO 91/10741. Human antibodies can be selected by competitive binding experiments, or otherwise, to have the same epitope specificity as a particular mouse antibody. Such antibodies generally retain the useful functional properties of the mouse antibodies. Human polyclonal antibodies can also be provided in the form of serum from humans immunized with an immunogenic agent. Optionally, such polyclonal antibodies can be concentrated by affinity purification using ADDLs as an affinity reagent.

As exemplified herein, humanized antibodies can also be produced by veneering or resurfacing of murine antibodies. Veneering involves replacing only the surface fixed region amino acids in the mouse heavy and light variable regions with those of a homologous human antibody sequence. Replacing mouse surface amino acids with human residues in the same position from a homologous human sequence has been shown to reduce the immunogenicity of the mouse antibody while preserving its ligand binding. The replacement of exterior residues generally has little, or no, effect on the interior domains, or on the interdomain contacts. (See, e.g., U.S. Pat. No. 6,797,492).

Human or humanized antibodies can be designed to have IgG, IgD, IgA, IgM or IgE constant regions, and any isotype, including IgG1, IgG2, IgG3 and IgG4. In particular embodiments, an antibody of the invention is IgG or IgM, or a combination thereof. Other embodiments of the present invention embrace a constant region formed by selective incorporation of human IgG4 sequences into a standard human IgG2 constant region. An exemplary mutant IgG2 Fc is IgG2m4, set forth herein as SEQ ID NO:140. Antibodies can be expressed as tetramers containing two light and two heavy chains, as separate heavy chains and light chains or as single chain antibodies in which heavy and light chain variable domains are linked through a spacer. Techniques for the production of single chain antibodies are well-known in the art.

Exemplary humanized antibodies derivatives of murine 20C2 monoclonal antibody are provided herein by CDR grafting and veneering. Amino acid sequences for IgG2M4 heavy chain variable regions, as well as kappa light chain variable regions for humanized 20C2 (i.e., Hu20C2A3) generated by veneering are presented in FIGS. 7A and 7C and set forth herein as SEQ ID NO:141 and SEQ ID NO:143.

Diabodies are also contemplated. A diabody refers to an engineered antibody construct prepared by isolating the binding domains (both heavy and light chain) of a binding antibody, and supplying a linking moiety which joins or operably links the heavy and light chains on the same polypeptide chain thereby preserving the binding function (see, Holliger et al. (1993) *Proc. Natl. Acad. Sci. USA* 90:6444; Poljak (1994) *Structure* 2:1121-1123). This forms, in essence, a radically abbreviated antibody, having only the variable domain necessary for binding the antigen. By using a linker that is too short to allow pairing between the two domains on the same chain, the domains are forced to pair with the complementary domains of another chain and create two antigen-binding sites. These dimeric antibody fragments, or diabodies, are bivalent and bispecific. The skilled artisan will appreciate that any method to generate diabodies can be used. Suitable methods are described by Holliger, et al. (1993)

supra, Poljak (1994) supra, Zhu, et al. (1996) *Biotechnology* 14:192-196, and U.S. Pat. No. 6,492,123, incorporated herein by reference.

Fragments of an isolated antibody of the invention are also expressly encompassed by the instant invention. Fragments are intended to include Fab fragments, F(ab')$_2$ fragments, F(ab') fragments, bispecific scFv fragments, Fd fragments and fragments produced by a Fab expression library, as well as peptide aptamers. For example, F(ab')$_2$ fragments are produced by pepsin digestion of the antibody molecule of the invention, whereas Fab fragments are generated by reducing the disulfide bridges of the F(ab')$_2$ fragments. Alternatively, Fab expression libraries can be constructed to allow rapid and easy identification of monoclonal Fab fragments with the desired specificity (see Huse, et al. (1989) *Science* 254:1275-1281). In particular embodiments, antibody fragments of the present invention are fragments of neutralizing antibodies which retain the variable region binding site thereof. Exemplary are F(ab')$_2$ fragments, F(ab') fragments, and Fab fragments. See generally Immunology: Basic Processes (1985) 2$^{nd}$ edition, J. Bellanti (Ed.) pp. 95-97.

Peptide aptamers which differentially recognize multi-dimensional conformations of ADDLs can be rationally designed or screened for in a library of aptamers (e.g., provided by Aptanomics SA, Lyon, France). In general, peptide aptamers are synthetic recognition molecules whose design is based on the structure of antibodies. Peptide aptamers consist of a variable peptide loop attached at both ends to a protein scaffold. This double structural constraint greatly increases the binding affinity of the peptide aptamer to levels comparable to that of an antibody (nanomolar range).

Exemplary nucleic acid sequences encoding heavy and light chain variable regions for use in producing antibody and antibody fragments of the instant invention are respectively disclosed herein in FIGS. 7B and 7D (i.e., SEQ ID NOs:142 and 144). As will be appreciated by the skilled artisan, the heavy chain variable regions disclosed herein can be used in combination with any one of the light chain variable regions disclosed herein to generate antibodies with modified affinities, dissociate constants, epitopes and the like.

Antibodies or antibody fragments of the present invention can have additional moieties attached thereto. For example, a microsphere or microparticle can be attached to the antibody or antibody fragment, as described in U.S. Pat. No. 4,493,825, the disclosure of which is incorporated herein by reference.

Moreover, particular embodiment embrace antibody or antibody fragments which are mutated and selected for increased antigen affinity, neutralizing activity (i.e., the ability to block binding of ADDLs to neuronal cells or the ability to block ADDL assembly), or a modified dissociation constant. Mutator strains of *E. coli* (Low, et al. (1996) *J. Mol. Biol.* 260:359-368), chain shuffling (Figini, et al. (1994) supra), and PCR mutagenesis are established methods for mutating nucleic acid molecules encoding antibodies. By way of illustration, increased affinity can be selected for by contacting a large number of phage antibodies with a low amount of biotinylated antigen so that the antibodies compete for binding. In this case, the number of antigen molecules should exceed the number of phage antibodies, but the concentration of antigen should be somewhat below the dissociation constant. Thus, predominantly mutated phage antibodies with increased affinity bind to the biotinylated antigen, while the larger part of the weaker affinity phage antibodies remains unbound. Streptavidin can then assist in the enrichment of the higher affinity, mutated phage antibodies from the mixture (Schier, et al. (1996) *J. Mol. Biol.* 255:28-43). Exemplary affinity-maturated light chain CDR3 amino acid sequences are disclosed herein (see Tables 6 and 7), with particular embodiments embracing a light chain CDR3 amino acid sequence of Xaa$_1$-Gln-Xaa$_2$-Thr-Arg-Val-Pro-Leu-Thr (SEQ ID NO:2), wherein Xaa$_1$ is Phe or Leu, and Xaa$_2$ is Ala or Thr. Affinity-maturated heavy chain CDR3 amino acid sequences are also provided herein. An exemplary heavy chain CDR3 amino acid sequence is set forth herein as Arg-Gln-Leu-Gly-Thr-Arg-Gly-Thr-Asp-Ala-Met-Asp-Tyr (SEQ ID NO:3). The present invention also embraces derivatives of this CDR3, e.g., Arg-Ala-Leu-Ser-Pro-Arg-Ser-Ile-Asp-Ala -Met-Asp-Tyr (SEQ ID NO:4), Arg-Gln-Leu-Gly-Ala-Arg-Lys-Thr -Asp-Ala-Met-Asp-Tyr (SEQ ID NO:5), Arg-Gln-Leu-Gly-Pro-Arg -Lys-Arg-Asp-Ala-Met-Asp-Tyr (SEQ ID NO:6), Arg-Gln-Leu-Gly -Lys-Leu-Lys-Thr-Asp-Ala-Met-Asp-Tyr (SEQ ID NO:7), or Arg -Gln-Leu-Gly-Arg-Arg-Ser-Val-Asp-Ala-Met-Asp-Tyr (SEQ ID NO:8), wherein differences with the Hu20C2A3 heavy chain CDR3 are underlined. In this regard, the present invention specifically embraces an anti-ADDL antibody having a CDR3 amino acid sequence of Arg-Xaa$_1$-Leu-Xaa$_2$-Xaa$_3$-Xaa$_4$-Xaa$_5$-Xaa$_6$-Asp-Ala-Met-Asp-Tyr (SEQ ID NO:9), wherein Xaa$_1$ is Gln or Ala; Xaa$_2$ is Ser or Gly; Xaa$_3$ is Pro, Ala, Lys, Arg, or Thr; Xaa$_4$ is Lys or Arg; Xaa$_5$ is Gly, Ser, or Lys; Xaa$_6$ is Val, Thr, Ile or Arg Other antibody derivatives encompassed within the scope of the present invention include any humanized antibody identical to Hu20C2A3's variable regions except with a one amino acid residue difference in the frame region of the light chain (e.g., Leu-Pro-Val-Thr-Pro-Gly -Glu-Pro-Ala-Ser, SEQ ID NO:10).

For some therapeutic applications it may be desirable to reduce the dissociation of the antibody from the antigen. To achieve this, phage antibodies are bound to biotinylated antigen and an excess of unbiotinylated antigen is added. After a period of time, predominantly the phage antibodies with the lower dissociation constant can be harvested with streptavidin (Hawkins, et al. (1992) *J. Mol. Biol.* 226:889-96).

Various immunoassays including those disclosed herein can be used for screening to identify antibodies, or fragments thereof, having the desired specificity for multi-dimensional conformations of ADDLs. Numerous protocols for competitive binding (e.g, ELISA), latex agglutination assays, immunoradiometric assays, kinetics (e.g., BIACORE™ analysis) using either polyclonal or monoclonal antibodies, or fragments thereof, are well-known in the art. Such immunoassays typically involve the measurement of complex formation between a specific antibody and its cognate antigen. A two-site, monoclonal-based immunoassay utilizing monoclonal antibodies reactive to two non-interfering epitopes is suitable, but a competitive binding assay can also be employed. Such assays can also be used in the detection of multi-dimensional conformations of ADDLs in a sample.

An antibody or antibody fragment can also be subjected to other biological activity assays, e.g., displacement of ADDL binding to neurons or cultured hippocampal cells or blockade of ADDL assembly, in order to evaluate neutralizing or pharmacological activity and potential efficacy as a prophylactic or therapeutic agent. Such assays are described herein and are well-known in the art.

Antibodies and fragments of antibodies can be produced and maintained as hydridomas or alternatively recombinantly produced in any well-established expression system including, but not limited to, *E. coli*, yeast (e.g., *Saccharomyces* spp. and *Pichia* spp.), baculovirus, mammalian cells (e.g., myeloma, CHO, COS), plants, or transgenic animals (Breitling and Dübel (1999) In: Recombinant Antibodies, John Wiley & Sons, Inc., NY, pp. 119-132). Antibodies and fragments of antibodies can be isolated using any appropriate methods including, but not limited to, affinity chromatography, immunoglobulins-binding molecules (e.g., proteins A, L, G or H), tags operatively linked to the antibody or antibody fragment (e.g., His-tag, FLAG®-tag, Strep tag, c-myc tag) and the like. See, Breitling and Dübel (1999) supra.

Antibodies and antibody fragments of the instant invention have a variety of uses including, diagnosis of diseases associated with accumulation of ADDLs, blocking or inhibiting binding of ADDLs to neuronal cells, blocking ADDL assembly, prophylactically or therapeutically treating a disease associated with ADDLs, identifying therapeutic agents that prevent binding of ADDLs to neurons, and preventing the phosphorylation of tau protein at Ser202/Thr205.

Antibody and antibody fragments of the instant invention are also useful in a method for blocking or inhibiting binding of ADDLs to neuronal cells. This method of the invention is carried out by contacting a neuron, in vitro or in vivo, with an antibody or antibody fragment of the present invention so that binding of ADDLs to the neuron is blocked. In particular embodiments, an antibody or antibody fragment of the instant invention achieves at least a 15%, 20%, 30%, 40%, 50%, 60%, 70%, 80%, 90%, 95%, or 97% decrease in the binding of ADDLs as compared to binding of ADDLs in the absence of the antibody or antibody fragment. The degree to which an antibody can block the binding of ADDLs to a neuron can be determined in accordance with the methods disclosed herein, i.e., immunocytochemistry or cell-based alkaline phosphatase assay or any other suitable assay. Antibodies particularly useful for decreasing binding of ADDLs to neuronal cells include anti-ADDL antibodies having a CDR3 amino acid sequence set forth in SEQ ID NO:9, as well as derivatives and fragments thereof.

Antibody and antibody fragments of the instant invention are further useful in a method for blocking or inhibiting assembly of ADDLs. This method involves contacting a sample containing amyloid β 1-42 peptides with an antibody or antibody fragment of the instant invention so that ADDL assembly is inhibited. The degree to which an antibody can block the assembly of ADDLs can be determined in accordance with the methods disclosed herein, i.e., FRET or fluorescence polarization or any other suitable assay. Antibodies particularly useful for blocking the assembly of ADDLs include anti-ADDL antibodies having a CDR3 amino acid sequence set forth in SEQ ID NO:9, as well as derivatives and fragments thereof.

Antibodies disclosed herein are also useful in methods for preventing the phosphorylation of tau protein at Ser202/Thr205. This method involves contacting a sample containing tau protein with an antibody or antibody fragment of the instant invention so that binding of ADDLs to neurons is blocked thereby preventing phosphorylation of tau protein. The degree to which an antibody can prevent the phosphorylation of tau protein at Ser202/Thr205 can be determined in accordance with the methods disclosed herein or any other suitable assay.

Blocking or decreasing binding of ADDLs to neurons, inhibiting assembly of ADDLs, and preventing the phosphorylation of tau protein at Ser202/Thr205 all find application in methods of prophylactically or therapeutically treating a disease associated with the accumulation of ADDLs. Accordingly, the present invention also embraces the use of an antibody or antibody fragment of the instant invention to prevent or treat a disease associated with the accumulation of ADDLs (e.g. Alzheimer's or similar memory-related disorders). Evidence in the art indicates that elevated levels of Aβ, but not necessarily aggregated plaque, are causative for Alzheimer's Disease-associated dementia and subsequent tau abnormalities. Aβ-derived diffusible ligands are directly implicated in neurotoxicity associated with Alzheimer's Disease. The art indicates that ADDLs are elevated in transgenic mice and Alzheimer's Disease patients and modulate functional activity associated with mnemonic processes in animal models. Thus, removing this form of Aβ could provide relief from the neurotoxicity associated with Alzheimer's Disease. As such, treatment with the instant antibody, which reduces central nervous system ADDL load, could prove efficacious for the treatment of Alzheimer's Disease. Patients amenable to treatment include individuals at risk of disease but not exhibiting symptoms, as well as patients presently exhibiting symptoms. In the case of Alzheimer's Disease, virtually anyone is at risk of suffering from Alzheimer's Disease if he or she lives long enough. Therefore, the antibody or antibody fragments of the present invention can be administered prophylactically to the general population without the need for any assessment of the risk of the subject patient. The present methods are especially useful for individuals who have a known genetic risk of Alzheimer's Disease. Such individuals include those having relatives who have been diagnosed with the disease, and those whose risk is determined by analysis of genetic or biochemical markers. Genetic markers of risk for Alzheimer's Disease include mutations in the APP gene, particularly mutations at position 717 and positions 670 and 671 referred to as the Hardy and Swedish mutations respectively. Other markers of risk are mutations in the presenilin genes, PS1 and PS2, and ApoE4, family history of Alzheimer's Disease, hypercholesterolemia or atherosclerosis. Individuals presently suffering from Alzheimer's Disease can be recognized from characteristic dementia, as well as the presence of risk factors described above. In addition, a number of diagnostic tests are available for identifying individuals who have Alzheimer's Disease. These include measurement of CSF tau and Aβ1-42 levels. Individuals suffering from Alzheimer's Disease can also be diagnosed by ADRDA criteria or the method disclosed herein.

In asymptomatic patients, treatment can begin at any age (e.g., 10, 20, 30 years of age). Usually, however, it is not necessary to begin treatment until a patient reaches 40, 50, 60 or 70 years of age. Treatment typically entails multiple dosages over a period of time. Treatment can be monitored by assaying for the presence of ADDLs over time.

In therapeutic applications, a pharmaceutical composition or medicament containing an antibody or antibody fragment of the invention is administered to a patient suspected of, or already suffering from such a disease associated with the accumulation of ADDLs in an amount sufficient to cure, or at least partially arrest, the symptoms of the disease (biochemical, histologic and/or behavioral), including its complications and intermediate pathological phenotypes in development of the disease. In prophylactic applications, a pharmaceutical composition or medicament containing an antibody or antibody fragment of the invention is administered to a patient susceptible to, or otherwise at risk of, a disease associated with the accumulation of ADDLs in an amount sufficient to achieve passive immunity in the patient thereby eliminating or reducing the risk, lessening the severity, or delaying the outset of the disease, including biochemical, histologic and/or behavioral symptoms of the disease, its complications and intermediate pathological phenotypes presenting during development of the disease. In some methods, administration of agent reduces or eliminates myocognitive impairment in patients that have not yet developed characteristic Alzheimer's pathology. In particular embodiments, an effective amount of an antibody or antibody fragment of the invention is an amount which achieves at least a 15%, 20%, 30%, 40%, 50%, 60%, 70%, 80%, 90%, 95%, or 97% decrease in the binding of ADDLs to neurons in the patient as compared to binding of ADDLs in the absence of treatment. As such, impairment of long-term potentiation/memory formation is decreased.

Effective doses of the compositions of the present invention, for the treatment of the above described conditions vary depending upon many different factors, including means of administration, physiological state of the patient, whether the patient is human or an animal, other medications administered, and whether treatment is prophylactic or therapeutic. Usually, the patient is a human but nonhuman mammals such as dogs or transgenic mammals can also be treated.

Treatment dosages are generally titrated to optimize safety and efficacy. For passive immunization with an antibody or antibody fragment, dosage ranges from about 0.0001 to 100 mg/kg, and more usually 0.01 to 5 mg/kg, of the host body weight are suitable. For example, dosages can be 1 mg/kg body weight or 10 mg/kg body weight or within the range of 1-10 mg/kg. In some methods, two or more antibodies of the invention with different binding specificities are administered simultaneously, in which case the dosage of each antibody administered falls within the ranges indicated. Antibodies are usually administered on multiple occasions, wherein intervals between single dosages can be weekly, monthly or yearly. An exemplary treatment regime entails subcutaneous dosing, once biweekly or monthly. Advantageously, subcutaneous administration has been found to reduce the flu-like symptoms associated with intravenous infusions (Lundin, et al. (2002) Blood 100:768-773). Intervals can also be irregular as indicated by measuring blood levels of antibody to ADDLs in the patient. In some methods, dosage is adjusted to achieve a plasma antibody concentration of 1-1000 µg/mL and in some methods 25-300 µg/mL. Alternatively, the antibody or antibody fragment can be administered as a sustained-release formulation, in which case less frequent administration is required. Dosage and frequency vary depending on the half-life of the antibody in the patient. In general, human and humanized antibodies have longer half-lives than chimeric antibodies and nonhuman antibodies. As indicated above, dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Antibody and antibody fragments of the instant invention can be administered as a component of a pharmaceutical composition or medicament. Pharmaceutical compositions or medicaments generally contain the active therapeutic agent and a variety of other pharmaceutically acceptable components. See Remington: The Science and Practice of Pharmacy, Alfonso R. Gennaro, editor, 20th ed. Lippincott Williams & Wilkins: Philadelphia, Pa., 2000. The preferred form depends on the intended mode of administration and therapeutic application. Pharmaceutical compositions can contain, depending on the formulation desired, pharmaceutically-acceptable, non-toxic carriers or diluents, which are defined as vehicles commonly used to formulate pharmaceutical compositions for animal or human administration. Diluents are selected so as not to affect the biological activity of the combination. Examples of such diluents are distilled water, physiological phosphate-buffered saline, Ringer's solutions, dextrose solution, and Hank's solution.

Pharmaceutical compositions can also contain large, slowly metabolized macromolecules such as proteins, polysaccharides such as chitosan, polylactic acids, polyglycolic acids and copolymers (such as latex-functionalized SEPHAROSE™, agarose, cellulose, and the like), polymeric amino acids, amino acid copolymers, and lipid aggregates (such as oil droplets or liposomes).

Administration of a pharmaceutical composition or medicament of the invention can be carried out via a variety of routes including, but not limited to, oral, topical, pulmonary, rectal, subcutaneous, intradermal, intranasal, intracranial, intramuscular, intraocular, or intra-articular injection, and the like. The most typical route of administration is intravenous followed by subcutaneous, although other routes can be equally effective. Intramuscular injection can also be performed in the arm or leg muscles. In some methods, agents are injected directly into a particular tissue where deposits have accumulated, for example, intracranial injection. In some embodiments, an antibody or antibody fragment is injected directly into the cranium. In other embodiments, antibody or antibody fragment is administered as a sustained-release composition or device, such as a MEDIPAD™ device.

For parenteral administration, antibody or antibody fragments of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are suitable liquid carriers, particularly for injectable solutions. Antibodies can be administered in the form of a depot injection or implant preparation which can be formulated in such a manner as to permit a sustained-release of the active ingredient.

An exemplary composition contains the instant antibody or antibody fragment formulated as a sterile, clear liquid at a concentration of at least 10 mg/ml in isotonic buffered saline (10 mM histidine, 150 mM sodium chloride, 0.01% (w/v) POLYSORBATE 80, pH 6.0). An exemplary antibody formulation is filled as a single dose, 0.6 ml glass vials filled with 3.3 ml of solution per vial. Each vial is stopped with a TEFLON-coated stopper and sealed with an aluminum cap.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced delivery.

For suppositories, binders and carriers include, for example, polyalkylene glycols or triglycerides; such suppositories can be formed from mixtures containing the active ingredient in the range of 0.5% to 10%, or more desirably 1%-2%.

Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained-release formulations or powders and contain 10%-95% of active ingredient, or more suitably 25%-70%.

Topical application can result in transdermal or intradermal delivery. Topical administration can be facilitated by co-administration of the agent with cholera toxin or detoxified derivatives or subunits thereof or other similar bacterial toxins (see Glenn, et al. (1998) *Nature* 391:851). Co-administration can be achieved by using the components as a mixture or as linked molecules obtained by chemical crosslinking or expression as a fusion protein.

Alternatively, transdermal delivery can be achieved using a skin path or using transferosomes (Paul, et al. (1995) *Eur. J. Immunol.* 25:3521-24; Cevc, et al. (1998) *Biochem. Biophys. Acta* 1368:201-15).

An antibody or antibody fragment of the invention can optionally be administered in combination with other agents that are at least partly effective in treatment of amyloidogenic disease. For example, the instant antibody can be administered with existing palliative treatments for Alzheimer's Disease, such as acetylcholinesterase inhibitors such as ARICEPT™, EXELON™, and REMINYL™ and, the NMDA antagonist, NAMENDA™. In addition to these approved treatments, the instant antibody can be used to provide synergistic/additive benefit for any of several approaches currently in development for the treatment of Alzheimer's Disease, which include without limitation, inhibitors of Aβ production and aggregation.

Antibody and antibody fragments of the instant invention also find application in the identification of therapeutic agents that prevent the binding of ADDLs to neurons (e.g., a hippocampal cell) thereby preventing downstream events attributed to ADDLs. Such an assay is carried out by contacting a neuron with ADDLs in the presence of an agent and using an antibody of antibody fragment of the invention to determine binding of the ADDLs to the neuron in the presence of the agent. As will be appreciated by the skilled artisan, an agent that blocks binding of ADDLs to a neuron will decrease the amount of ADDLs bound to the neuron as compared to a neuron which has not been contacted with the agent; an amount which is detectable in an immunoassay employing an antibody or antibody fragment of the instant invention. Suitable immunoassays for detecting neuronal-bound ADDLs are disclosed herein.

Agents which can be screened using the method provided herein encompass numerous chemical classes, although typically they are organic molecules, preferably small organic compounds having a molecular weight of more than 100 and less than about 2,500 daltons. Agents encompass functional groups necessary for structural interaction with proteins, particularly hydrogen bonding, and typically include at least an amine, carbonyl, hydroxyl or carboxyl group, preferably at least two of the functional chemical groups. The agents often contain cyclical carbon or heterocyclic structures and/or aromatic or polyaromatic structures substituted with one or more of the above functional groups. Agents can also be found among biomolecules including peptides, antibodies, saccharides, fatty acids, steroids, purines, pyrimidines, derivatives, structural analogs or combinations thereof. Agents are obtained from a wide variety of sources including libraries of natural or synthetic compounds.

A variety of other reagents such as salts and neutral proteins can be included in the screening assays. Also, reagents that otherwise improve the efficiency of the assay, such as protease inhibitors, nuclease inhibitors, anti-microbial agents, and the like can be used. The mixture of components can be added in any order that provides for the requisite binding.

Agents identified by the screening assay of the present invention will be beneficial for the treatment of amyloidogenic diseases and/or tauopathies. In addition, it is contemplated that the experimental systems used to exemplify these concepts represent research tools for the evaluation, identification and screening of novel drug targets associated with amyloid beta induction of tau phosphorylation.

The present invention also provides methods for detecting ADDLs and diagnosing a disease associated with accumulation of ADDLs using an antibody or antibody fragment of the instant invention. A disease associated with accumulation of ADDLs is intended to include any disease wherein the accumulation of ADDLs results in physiological impairment of long-term potentiation/memory formation. Diseases of this type include, but are not limited to, Alzheimer's Disease and similar memory-related disorders.

In accordance with these methods, a sample from a patient is contacted with an antibody or antibody fragment of the invention and binding of the antibody or antibody fragment to the sample is indicative of the presence of ADDLs in the sample. As used in the context of the present invention, a sample is intended to mean any bodily fluid or tissue which is amenable to analysis using immunoassays. Suitable samples which can be analyzed in accordance with the methods of the invention include, but are not limited to, biopsy samples and fluid samples of the brain from a patient (e.g., a mammal such as a human). For in vitro purposes (e.g., in assays monitoring oligomer formation), a sample can be a neuronal cell line or tissue sample. For diagnostic purposes, it is contemplated that the sample can be from an individual suspected of having a disease associated with accumulation of ADDLs or from an individual at risk of having a disease associated with accumulation of ADDLs, e.g., an individual with a family history which predisposes the individual to a disease associated with accumulation of ADDLs.

Detection of binding of the antibody or antibody fragment to ADDLs in the sample can be carried out using any standard immunoassay (e.g., as disclosed herein), or alternatively when the antibody fragment is, e.g., a peptide aptamer, binding can be directly detected by, for example, a detectable marker protein (e.g., β-galactosidase, GFP or luciferase) fused to the aptamer. Subsequently, the presence or absence of the ADDL-antibody complex is correlated with the presence or absence, respectively, of ADDLs in the sample and therefore the presence or absence, respectively, of a disease associated with accumulation of ADDLs. It is contemplated that one or more antibodies or antibody fragments of the present invention can be used in conjunction with current non-invasive immuno-based imaging techniques to greatly enhance detection and early diagnosis of a disease associated with accumulation of ADDLs.

To facilitate diagnosis the present invention also pertains to a kit for containing an antibody or antibody fragment of the instant invention. The kit includes a container holding one or more antibody or antibody fragments which recognizes multi-dimensional conformation of ADDLs and instructions for using the antibody for the purpose of binding to ADDLs to form an antibody-antigen complex and detecting the formation of the antibody-antigen complex such that the presence or absence of the antibody-antigen complex correlates with presence or absence of ADDLs in the sample. Examples of containers include multiwell plates which allow simultaneous detection of ADDLs in multiple samples.

The invention is described in greater detail by the following non-limiting examples.

EXAMPLE 1

General Materials and Methods

ADDL Preparation. ADDLs in F12 medium (Biosource, Camarillo, Calif.) were prepared from Aβ1-42 in accordance with established methods (Lambert, et al. (2001) supra). Briefly, Aβ1-42 peptide (American Peptide Co., Sunnyvale, Calif. or California Peptide Research, Inc., Napa, Calif.) was weighed and placed in a glass vial capable of holding a sufficient quantity of HFIP (1,1,1,3,3,3-hexafluoro-2-propanol) to achieve a peptide concentration of 10 mg/mL. HFIP was added to the dry peptide, the vial was capped and gently swirl to mix, and the peptide/HFIP solution was stored at room temperature for at least one hour. Aliquots (50 or 100 μL, 0.5 or 1.0 mg, respectively) of peptide solution was dispensed into a series of 1.5 mL conical centrifuge tubes. The tubes were placed in a SPEEDVAC® overnight to remove the HFIP. Tubes containing the dried peptide film were capped and stored at −70° C. in a sealed container with dessicant.

Prior to use, the Aβ1-42 peptide film was removed from −70° C. storage and allowed to warm to room temperature. Fresh DMSO (44 μL/mg of peptide film; 5 mM) was added and the peptide/DMSO mixture was incubated on a vortex mixer at the lowest possible speed for ten minutes. F12 media (2 mL/mg peptide) was dispensed into each tube of DMSO/peptide and the tube was capped and mixed by inversion. The 100 μM preparation was stored at 2-8° C. for eighteen to twenty four hours. The samples were centrifuged at 14,000×g for ten minutes at 2-8° C. The supernatant was transferred to a fresh tube and stored at 2-8° C. until used.

Biotinylated ADDL preparations (bADDLs) were prepared in the same manner as described above for ADDL preparations using 100% N-terminal biotinylated amyloid beta peptide (American Peptide Company, Sunnyvale, Calif.).

Monomer Preparation. HFIP dry down preparations of amyloid beta (1-40) peptide (Aβ-40) were prepared as outlined for Aβ(1-42) peptide. The peptide film was dissolved in 2 mL of 25 mM borate buffer (pH 8.5) per mg of peptide, divided into aliquots, and frozen at −70° C. until used.

Primary Neurons. Primary hippocampal cultures were prepared from frozen, dissociated neonatal rat hippocampal cells (Cambrex, Corp., East Rutherford, N.J.) that were thawed and plated in 96-well COSTAR® plates at a concentration of 20,000 cells per well. The cells were maintained in NEUROBASAL™ media without L-glutamine (GIBCO-BRL™, Gaithersburg, Md.) and supplemented with B27 (GIBCO-BRL™, Gaithersburg, Md.) for a period of two weeks and then used for binding studies.

Immunocytochemistry. Immunocytochemistry was performed according to established methods (Lambert, et al. (2001) supra), except the secondary antibodies were conjugated to ALEXAFLUOR® 588 (Molecular Probes, Eugene, Oreg.). Antibodies and ADDLs were preincubated for 1 hour at room temperature, at a molar ratio of 1:4 antibody:ADDL before application to the 21-day hippocampal cell culture. For endogenous ADDLs, human brain protein (prepared as in Lambert, et al. (2001) supra) was incubated with cells for 1 hour before the cells were washed, fixed, and visualized as above.

Lightly fixed frozen sections (4% paraformaldehyde at 4° C. for 30 hours and cryoprotected in 40 μm sucrose) from Alzheimer's Disease and control hippocampus were incubated with antibody (1:1000 in phosphate-buffered saline (PBS)) overnight at 4° C. After removal of antibody, sections were washed 3 times with PBS and incubated with secondary antibody at room temperature. Binding was then visualized with DAB (SIGMA™, St. Louis, Mo.). Sections were then counterstained with hematoxylin, mounted, and imaged on a NIKON® ECLIPSE® E600 light microscope with a SPOT™ INSIGHT™ digital video camera (v. 3.2).

ELISA. Polyclonal anti-ADDLs IgG (M90/1; Bethyl Laboratories, Inc., Montgomery, Tex.) was plated at 0.25 mg/well on IMMULON™ 3 REMOVAWELL™ strips (Dynatech Labs, Chantilly, Va.) for 2 hours at room temperature and the wells blocked with 2% BSA in TBS. Samples diluted with 1% BSA in F12 were added to the wells, allowed to bind for 2 hours at 4° C., and washed 3× with BSA/TBS at room temperature. Monoclonal antibodies diluted in BSA/TBS were incubated for 90 minutes at room temperature and detected with a VECTASTAIN® ABC kit to mouse IgG. The HRP label was visualized with BIO-RAD® peroxidase substrate and read at 405 nm on a Dynex MRX-TC microplate reader.

EXAMPLE 2

Isolation of Mouse Antibody Variable Region Sequences

The cDNAs coding for the variable domains of the 20C2 mouse antibody were cloned and sequenced following a polymerase chain reaction (PCR) using specially designed primers that hybridize to the 5'-ends of the mouse constant regions and to the murine leader sequences upstream of the V regions. This ensured that the mouse variable region sequences obtained were complete and accurate. In short, mRNA was extracted from mouse hybridoma cell lines using the QIAGEN® OLIGOTEX® Direct mRNA Mini Kit and subsequently converted to cDNA using a first-strand cDNA synthesis kit. The cDNA was then used as template in PCR reactions to obtain the antibody variable region sequences.

To obtain the light chain variable region sequence, eleven independent PCR reactions were set up using each of the eleven light chain 5' PCR primers (MKV-1 to MKV-11) and the 3' PCR primer MKC-1 (Table 1).

TABLE 1

| 5' Primer | Sequence | SEQ ID NO: |
|---|---|---|
| MKV-1 | GAT CTC TAG ATG AAG ATT GCC TGT TAG GCT GTT GGT GCT G | 11 |
| MKV-2 | GAT CTC TAG ATG GAG WCA GAC ACA CTC CTG YTA TGG GTG | 12 |
| MKV-3 | AT CTC TAG ATG AGT GTG CTC ACT CAG GTC CTG GSG TTG | 13 |
| MKV-4 | GAT CTC TAG ATG AGG RCC CCT GCT CAG WTT YTT GGM WTC TTG | 14 |
| MKV-5 | GAT CTC TAG ATG GAT TTW CAG GTG CAG ATT WTC AGC TTC | 15 |
| MKV-6 | GAT CTC TAG ATG AGG TKC YYT GYT SAY CTY CTC TGR GG | 16 |
| MKV-7 | GAT CTC TAG ATG GGC WTC AAA GAT GGA GTC ACA KWY YCW GG | 17 |

TABLE 1-continued

| | | | SEQ ID NO: |
|---|---|---|---|
| MKV-8 | GAT | CTC TAG ATG TGG GGA YCT KTT TYC MMT TTT TCA ATG | 18 |
| MKV-9 | GAT | CTC TAG ATG GTR TCC WCA SCT CAG TTC CTT G | 19 |
| MKV-10 | GAT | CTC TAG ATG TAT ATA TGT TTG TTG TCT ATT TCT | 20 |
| MKV-11 | GAT | CTC TAG ATG GAA GCC CCA GCT CAG CTT CTC TTC C | 21 |

| 3' Primer Sequence | | SEQ ID NO: |
|---|---|---|
| MKC-1 | GAT CGA GCT CAC TGG ATG GTG GGA AGA TGG | 22 |

Underlined and italic sequences denote XbaI and SacI restriction sites, respectively. W = A or T, M = A or C, K = G or T, Y = C or T, and R = A or G.

To obtain the heavy chain variable region sequences twelve independent PCR reactions were set up using each of the twelve heavy chain 5' PCR primers (MHV-1 to MHV-12) and the appropriate isotype specific 3' primer (MHCG-1, MHCG-2A, MHCG-2B, MHCG-3) (Table 2).

TABLE 2

| 5' Primer Sequence | | SEQ ID NO: |
|---|---|---|
| MHV-1 | GAT CTC TAG ATG AAA TGC AGC TGG GGC ATS TTC TTC | 23 |
| MHV-2 | GAT CTC TAG ATG GGA TGG AGC TRT ATC ATS YTC TT | 24 |
| MHV-3 | GAT CTC TAG ATG AAG WTG TGG TTA AAC TGG GTT TTT | 25 |
| MHV-4 | GAT CTC TAG ATG RAC TTT GGG YTC AGC TTG RTT T | 26 |
| MHV-5 | GAT CTC TAG ATG GGA CTC CAG GCT TCA ATT TAG TTT TCC TT | 27 |
| MHV-6 | GAT CTC TAG ATG GCT TGT CYT TRG SGC TRC TCT TCT GC | 28 |
| MHV-7 | GAT CTC TAG ATG GRA TGG AGC KGG RGT CTT TMT CTT | 29 |
| MHV-8 | GAT CTC TAG ATG AGA GTG CTG ATT CTT TTG TG | 30 |
| MHV-9 | GAT CTC TAG ATG GMT TGG GTG TGG AMC TTG CTT ATT CCT G | 31 |
| MHV-10 | GAT CTC TAG ATG GGC AGA CTT ACC ATT CTC ATT CCT G | 32 |
| MHV-11 | GAT CTC TAG ATG GAT TTT GGG CTG ATT TTT TTT ATT G | 33 |
| MHV-12 | GAT CTC TAG ATG ATG GTG TTA AGT CTT CTG TAC CTG | 34 |

| 3' Primer Sequence | | SEQ ID NO: |
|---|---|---|
| MHCG-1 | GCATC GAG CTC CAG TGG ATA GAC AGA TGG GGG | 35 |
| MHCG-2A | GCATC GAG CTC CAG TGG ATA GAC CGA TGG GGG | 36 |
| MHCG-2B | GCATC GAG CTC CAG TGG ATG AGC TGA TGG GGG | 37 |
| MHCG-3 | GCATC GAG CTC CAA GGG ATA GAC AGA TGG GGC | 38 |

Underlined and italic sequences denote XbaI and SacI restriction sites, respectively. W = A or T, M = A or C, K = G or T, Y = C or T, and R = A or G.

Each of the light chain PCR reactions contained 46 µL INVITROGEN™ PLATINUM® PCR Super Mix, 1.0 µL of one of the 100 µM 5' primers (MKV-1 to MKV-11), 1.0 µL of the 100 µM 3' primer (MKC-1), and 2.0 µl of hybridoma cDNA. Similar PCR reactions were employed to clone the mouse heavy chain variable region sequences. Reactions were placed in a DNA thermal cycler and, after an initial denaturation step at 97° C. for 2.0 minutes, subjected to 30 cycles of: 95° C. for 30 seconds, 55° C. for 45 seconds, and 72° C. for 90 seconds. Following the last cycle, a final extension step at 72° C. for 10 minutes was employed. To determine which PCR reactions yielded product, 5 µL aliquots from each reaction were separated on 1.5% (w/v) agarose/1× TAE buffer gels, containing 0.5 µg/mL ethidium bromide. PCR products from reactions that produced fragments of the expected size (420 to 500 bp) were then gel purified, digested with XbaI and SacI and ligated into the XbaI and SacI sites in the multicloning region of plasmid pNEB193 (New England Biolabs, Beverly, Mass.). Alternatively, PCR products were ligated directly into plasmid pCR®2.1 using the INVITROGEN™ TA CLONING® kit. Ligation products were then transformed into XL-1 cells and aliquots of the transformed *E. coli* were plated onto LB agar plates containing 50 µg/mL ampicillin and overlaid with 40 µL of X-Gal stock (50 mg/mL) and 40 µl IPTG (100 mM) solution for blue/white selection. Plates were incubated overnight at 37° C. and potential clones were identified as white colonies. DNA from at least 24 independent clones for each PCR product were sequenced on both strands using universal forward and reverse primers for pNEB193 and pCR®2.1. The resulting sequences were then assembled into a contig to generate a consensus sequence for each antibody light and heavy chain variable region. Using this approach the sequences were determined for the light and heavy antibody variable regions of hybridoma 20C2 (FIGS. 1A-1B). The six complementarity-determining regions (CDRs), which form the structure complementary to the antigen, are underlined in FIGS. 1A-1B.

EXAMPLE 3

Humanization of Mouse Anti-ADDL Antibody Variable Region Sequences

Mouse antibody heavy and light variable domain nucleic acids obtained from mouse hybridoma cell line 20C2 were humanized using a CDR grafting approach. It will be appreciated by those skilled in the art that humanization of mouse antibody sequences can maximize the therapeutic potential of an antibody by improving its serum half-life and Fc effector functions thereby reducing the anti-globulin response.

Humanization by CDR grafting was carried out by selecting the human light and heavy chain variable regions from the NCBI protein database with the highest homology to the mouse variable domains. The mouse variable region sequences were compared to all human variable region sequences in the database using the protein-protein Basic Local Alignment Search Tool (BLAST). Subsequently, mouse CDRs were joined to the human framework regions and the preliminary amino acid sequence was analyzed. All differences between the mouse and human sequences in the framework regions were evaluated particularly if they were part of the canonical sequences for loop structure or were residues located at the VL/VH interface (O'Brien and Jones (2001) In: Antibody Engineering, Kontermann and Dubel (Eds.), Springer Laboratory Manuals). Framework regions were also scanned for unusual or rare amino acids in comparison to the consensus sequences for the human subgroup and for potential glycosylation sites. Wherein amino acid sequence differences existed between the mouse and human framework region sequences that were not found to be involved in canonical sequences, or located at the VL/VH interface, the human residue was selected at that position. Wherein a difference in a key residue existed, two versions of the variable region sequence were generated for evaluation. The CDR grafting strategy made the minimum number of changes to the human framework region so that good antigen binding was achieved while maintaining human framework regions that closely matched the sequence from a natural human antibody. The heavy chain and light chain variable region amino acid sequences of the resulting humanized antibody generated by CDR grafting of murine 20C2 are shown in FIGS. 2A and 2B, respectively. This antibody is designated herein as Hu20C2.

Humanized sequences for 20C2 were also designed using a veneering strategy (See, e.g., U.S. Pat. No. 6,797,492). Humanization was carried out by selecting the human light and heavy chain variable regions from the NCBI protein database with the highest homology to the mouse variable domains, as well as to the closest human antibody germline family or families (see, Kabat, et al. (1991) 5$^{th}$ ed., Sequences of proteins of immunological interest, U.S. Dept. Health and Human Services, NIH, Washington D.C.). The mouse variable region sequences were compared to all human variable region sequences in the database using protein-protein BLAST. The murine variable sequences and their closest human homologues were modeled to the closest crystallized human antibody as determined by computer modeling as practiced in the art. From the model of the murine VH and VL sequences, a surface area map was constructed, which dictated the solvent accessibility of the amino acids in the mouse heavy and light variable regions. To confirm the modeling, these exposed residues were compared position-by-position with known surface accessible residues (see, e.g., Padlan (1994) Mol. Immunol. 31(3):169-217). A score was assigned for each residue in the sequence designating it as exposed, mostly exposed, partly buried, mostly buried and buried according to established methods (see, U.S. Pat. No. 6,797,492, incorporated herein by reference in its entirety). Mouse framework residues that scored as exposed or mostly exposed and differed from the homologous human sequence were changed to the human residue at that position. The designed veneered sequences retained the mouse CDRs, residues neighboring the CDRs, residues known be involved in canonical sequences, residues located at the VL/VH interface, and residues at the N-terminal sequences of the mouse heavy and light chain. The N-terminal sequences are known to be contiguous with the CDR surface and are potentially involved in ligand binding. Once the veneered sequences were finalized they were remodeled to look for are any potential obvious structural issues. A total of 12 and 9 amino acid residues were changed in the heavy chain and light chain frames, respectively. The heavy chain and light chain variable region amino acid sequences of the resulting humanized antibody generated by veneering of murine 20C2 are shown in FIGS. 2A and 2B, respectively. This antibody is designated herein as Hu20C2A3.

In comparison to 20C2, it is noted that the light chain substitutions resulting in Hu20C2A3, but not the heavy chain substitutions, are in common with Hu20C2 (FIG. 2). In particular, heavy chain variable region CDR3 is unique to Hu20C2A3.

Once the humanized amino acid sequences were selected the sequences were reverse-translated to obtain the corresponding DNA sequence. The DNA sequences were codon-optimized using art-established methods (Lathe (1985) J. Mol. Biol. 183(1):1-12) and designed with flanking restriction enzyme sites for cloning into human antibody expression vectors. The nucleotide sequences encoding the light chain variable region and two versions of the heavy chain variable region for Hu20C2 are presented in FIGS. 3A-3C. The two heavy chain variable region versions differ by a single amino acid substitution at position 24; heavy chain variable region for version A of Hu20C2 is Phe at position 24 and heavy chain variable region of version B of Hu20C2 is Leu at position 24.

EXAMPLE 4

Affinity Maturation

Affinity maturation was carried out on the Hu20C2 antibody. Nucleic acid molecules encoding humanized Hu20C2 versions A and B variable heavy chain only, light chain only or heavy chain version A and light chain together were cloned in the Fab phage-display vector pFab4. Nucleic acid sequence analysis confirmed sequence and orientation in pFab4. The annotated Hu20C2 Fab sequences in pFab4 are presented in FIGS. 4A-4C and set forth herein as SEQ ID NO:116 for heavy chain version A, SEQ ID NO:117 for heavy chain version B, and SEQ ID NO:118 for the light chain. The nucleotide sequence for heavy chain version A and light chain together in the pFab4 vector is presented in FIGS. 4D-4E. These constructs were used in the Hu20C2 maturation program using art-established phage-displayed Fab library methods.

Light Chain Maturation. Two libraries were designed to mutate the nine wild-type amino acids of CDR3 of the light (kappa) chain of Hu20C2 (i.e., Phe-Gln-Gly-Ser-Leu-Val-Pro-Leu-Thr; SEQ ID NO:39). These libraries were designated LC3-1 and LC3-2 representing light chain CDR3 sequences of Xaa-Xaa-Xaa-Xaa-Xaa-Val-Pro-Leu-Thr (SEQ ID NO:40) and Phe-Gln-Gly-Ser-Xaa-Xaa-Xaa-Xaa-Xaa (SEQ ID NO:41), respectively. Biotinylated reverse primers, 20C2LC3-1 (SEQ ID NO:123) and 20C2LC3-2 (SEQ ID NO:126), were used in combination with forward primer 20C2LC3F (SEQ ID NO:120) to generate the LC3-1 and LC3-2 libraries (see FIG. 5A). Primers were purified by polyacrylamide gel electrophoresis, whereas the vector DNA was purified by gel electrophoresis and electroelution. The two light chain libraries were designed to be randomly mutated.

The final diversities of the three 10G5H6 LC$_3$ libraries were 4.76×10$^8$ and 7.45×10$^8$, respectively (Table 3). Sequence analysis of approximately 100 clones from the libraries showed 100% diversity of mutant clones at the designed amino acid positions.

TABLE 3

| Characteristic | Light Chain Library | |
| --- | --- | --- |
| | LC3-1 | LC3-2 |
| Vector | pFab3d20C2HS | pFab3d20C2HS |
| Number of Transformants | 4.76 × 10$^8$ | 7.45 × 10$^8$ |
| Library Diversity | 4.76 × 10$^8$ × 0.89 = 4.24 10$^8$ | 7.45 × 10$^8$ × 0.90 = 6.71 10$^8$ |
| Primary Library Volume | 2 mL | 2 mL |
| Primary Library Titer | 2.13 × 10$^{11}$ | *9.3 × 10$^{10}$ |

*Higher titers are achieved by concentration or phage rescue.

Soluble panning of the two light chain libraries against high molecular weight bADDL was completed. Briefly, four rounds of panning were carried out using biotinylated high molecular weight ADDL (bADDL). The first three rounds were carried out using approximately 1.5 µM antigen concentration (input=1×10$^{10}$ to 1×10$^{11}$). Upon completion of the third round, the outputs of the two libraries were combined and divided into three groups for analysis with 10 nM, 100 nM and approximately 1.5 µM antigen to increase panning stringency. As such, a total of 58 output plates were tested in phage ELISA assays, i.e., two plates per library in the first round (a total of four plates), six plates per library in the second round (a total of 12 plates), eight plates for LC$_3$-1 and 10 plates for LC3-2 libraries in the third round (a total of 18 plates) and eight plates for each antigen concentration in the fourth round (a total of 24 plates).

Panning resulted in 1000 hits, 436 of which were sequenced (Table 4).

TABLE 4

| Round | Antigen | Input | Output | % Recovery | ELISA Screen* | Sequenced |
| --- | --- | --- | --- | --- | --- | --- |
| 1$^a$ | 1.6 µM | 2.13 × 10$^{10}$ | 2.13 × 10$^4$ | 3.42 × 10$^{-6}$ | 0% (0/176) | 0 |
| 2$^a$ | 2.0 µM | 1.55 × 10$^{11}$ | 1.88 × 10$^5$ | 1.21 × 10$^{-6}$ | 1.5% (8/528) | 8 |
| 3$^a$ | 1.1 µM | 1.80 × 10$^{10}$ | 7.8 × 10$^4$ | 4.3 × 10$^{-6}$ | 5.8% (41/704) | 41 |
| 1$^b$ | 1.6 µM | 9.30 × 10$^9$ | 5.7 × 10$^4$ | 6.13 × 10$^{-6}$ | 2.3% (7/176) | 4 |
| 2$^b$ | 2.0 µM | 1.23 × 10$^{11}$ | 1.07 × 10$^5$ | 8.7 × 10$^{-7}$ | 4.5% (24/528) | 24 |
| 3$^b$ | 1.1 µM | 1.37 × 10$^{10}$ | 3.32 × 10$^5$ | 2.42 × 10$^{-5}$ | 15% (134/880) | 134 |
| 4$^c$ | 1.1 µM | 3.0 × 10$^{11}$ | 1.37 × 10$^5$ | 4.6 × 10$^{-7}$ | 39% (274/704) | — |
| 4$^c$ | 100 nM | 3.0 × 10$^{11}$ | 3.88 × 10$^5$ | 1.29 × 10$^{-6}$ | 41% (290/704) | — |
| 4$^c$ | 10 nM | 3.0 × 10$^{11}$ | 1.6 × 10$^5$ | 5.3 × 10$^{-7}$ | 32% (225/704) | 225 |
| | | | Total | | 1000/5104 | 436 |

$^a$20C2 LC3-1 versus high molecular weight 10% bADDL.
$^b$20C2 LC3-2 versus high molecular weight 10% bADDL.
$^c$20C2 LC3-1 + 20C2 LC3-2 versus high molecular weight 10% bADDL.
*Hits per total number of colonies.

Sequence and frequency of highly enriched clones are presented in Table 5.

TABLE 5

| Clone Designation | LC CDR 3 | SEQ ID NO: | Round 2 | Round 3 | Round 4 | Total |
| --- | --- | --- | --- | --- | --- | --- |
| Hu20C2LC | FQGSLVPLT | 39 | 6 | 15 | 14 | 35 |
| SJ-p1-31 | ADTTHVPLT | 42 | | 1 | 2 | 3 |
| SJ-p1-14 | AHSTFVPLT | 43 | 1 | 1 | 2 | 4 |
| 4P2-12-E3 | AQASFVPLT | 44 | | | 2 | 2 |
| SJ-p1-38 | AQATKVPLT | 45 | | 1 | 1 | 2 |
| 4P3-59 | AQSSKVPLT | 46 | | | 2 | 2 |
| SJ-p2-14 | AQSTLVPLT | 47 | | 1 | 2 | 3 |
| 4P3-11 | FAASSVPLT | 48 | | | 2 | 2 |
| 4P3-1 | FESTYVPLT | 49 | | | 2 | 2 |
| SJ-p2-10 | FESSRVPLT | 50 | | 1 | 1 | 2 |
| SJ-p2-11 | FNATWVPLT | 51 | | 2 | | 2 |
| SJ-p2-60 | FQASRVPLT | 52 | | 1 | 5 | 6 |
| SJ-p1-18 | FQATRVPLT | 53 | | 1 | 5 | 6 |
| SJ-p3-51 | FQGSFIGLS | 54 | 1 | | 1 | 2 |
| SJ-p3-16 | FQGSFIPGT | 55 | | 2 | 3 | 5 |
| SJ-p8-8F | FQGSFLPPS | 56 | | 1 | 1 | 2 |
| SJ-p3-26 | FQGSFLPQL | 57 | 1 | 2 | | 3 |
| SJ-p3-15 | FQGSLFPPV | 58 | 1 | 2 | | 3 |
| SJ-p2-70 | FQGSLFSPS | 59 | 1 | 5 | | 6 |

TABLE 5-continued

| Clone Designation | LC CDR 3 | SEQ ID NO: | Round 2 | Round 3 | Round 4 | Total |
|---|---|---|---|---|---|---|
| SJ-p3-24 | FQGSRIPIS | 60 | | 1 | 1 | 2 |
| SJ-p3-33 | FQGSRLPVS | 61 | | 2 | 3 | 5 |
| SJ-p3-14 | FQGSRVPLV | 62 | | 2 | 1 | 3 |
| SJ-p2-1F | FQSSFVPLT | 63 | | 6 | 8 | 14 |
| 4P1-22 | FQSSRVPLT | 64 | | | 15 | 15 |
| SJ-p2-44 | GQTTLVPLT | 65 | | 1 | 3 | 4 |
| SJ-p1-56 | HESTLVPLT | 66 | | 2 | 1 | 3 |
| 4P1-40 | HQSSKVPLT | 67 | | | 4 | 4 |
| SJ-p2-20 | IQTSLVPLT | 68 | | 2 | | 2 |
| SJ-p1-41 | IQAALVPLT | 69 | | 1 | 1 | 2 |
| SJ-p2-13 | LQSSFVPLT | 70 | 1 | 4 | | 5 |
| 4P1-26 | LETSRVPLT | 71 | | | 3 | 3 |
| SJ-p1-33 | LASSHVPLT | 72 | | 2 | 1 | 3 |
| SJ-p2-27 | LNSTTVPLT | 73 | | 2 | 4 | 6 |
| SJ-p2-62 | LQSKSVPLT | 74 | | 2 | | 2 |
| 4P2-26-E5 | LQSVRVPLT | 75 | | | 3 | 3 |
| 4P1-32 | LQSSLVPLT | 76 | | | 5 | 5 |
| SJ-p2-37 | LQTGRVPLT | 77 | | 2 | 2 | 4 |
| SJ-p2-64 | LQTSFVPLT | 78 | | 3 | | 3 |
| 4P1-20 | LQTSNVPLT | 79 | | | 5 | 5 |
| SJ-p2-39 | LQTTRVPLT | 80 | | 2 | 6 | 8 |
| SJ-p2-52 | LSSTFVPLT | 81 | | 3 | 1 | 4 |
| SJ-p2-6L | LSSTHVPLT | 82 | | 2 | 1 | 3 |
| 4P1-77 | LTSSAVPLT | 83 | | | 2 | 2 |
| SJ-p1-59 | LVSSLVPLT | 84 | | 2 | | 2 |
| SJ-p2-23 | METANVPLT | 85 | | 2 | | 2 |
| SJ-p1-9M | MQSSFVPLT | 86 | | 1 | 3 | 4 |
| SJ-p2-28 | MQSSLVPLT | 87 | | 1 | 2 | 3 |
| SJ-p1-21 | MQTSKVPLT | 88 | | 1 | 1 | 2 |
| 4P1-17 | SQARMVPLT | 89 | | | 3 | 3 |
| SJ-p2-66 | SQASRVPLT | 90 | | 1 | 2 | 3 |
| SJ-p1-49 | TQSTQVPLT | 91 | | 2 | 1 | 3 |
| SJ-p2-24 | VCATFVPLT | 92 | | 1 | 1 | 2 |
| 4P1-41 | VQSSAVPLT | 93 | | | 2 | 2 |
| SJ-p2-51 | VQTSLVPLT | 94 | | 12 | 31 | 43 |
| 4P1-64 | VQTSVVPLT | 95 | | | 3 | 3 |
| SJ-p2-55 | VQTTAVPLT | 96 | | 2 | | 2 |
| SJ-p1-25 | LQTARVPLT | 97 | | 1 | 3 | 4 |

Fab fragments from the 10 top clones based on enrichment frequency were prepared and a total of 15 clones were converted into IgG1 humanized A version and two clones, 20C2-6 and 20C2-8, were converted to IgG1 humanized B version. $K_D$ values for these clones were measured by BIACORE™ using biotin-Aβ1-20 (Table 6) and bADDL (Table 7) as antigens. Dramatic improvements in affinity were observed as compared to parental humanized 20C2A and 20C2B, as well as mouse 20C2 antibodies. In particular, low nanomolar to sub-picomolar $K_D$s were achieved with a light chain CDR3 of the sequence $Xaa_1$-Gln-$Xaa_2$-Thr-Arg-Val-Pro-Leu-Thr (SEQ ID NO:2), wherein $Xaa_1$ is Phe or Leu, and $Xaa_1$ is Ala or Thr. Moreover, a comparison between $K_D$ values obtained with BIACORE™ using biotin-Aβ1-20 and bADDL further demonstrates that anti-ADDL antibodies such as Hu20C2 preferentially bind multi-dimensional conformations of ADDLs over monomeric Aβ peptides.

TABLE 6

| Name | Clone | LC-CDR3 | SEQ ID NO: | $K_D$ (Biotin-Aβ1-20) Fab | IgG1#1 | IgG1#2 |
|---|---|---|---|---|---|---|
| 20C2-1A | SJ-p2-60 | FQASRVPLT | 52 | 91 nM | 1.2 nM | — |
| 20C2-2A | SJ-p1-18 | FQATRVPLT | 53 | 28 nM | 686 pM | 2 nM |
| 20C2-3A | SJ-p3-16 | FQGSFIPGT | 55 | — | 1.7 nM | — |
| 20C2-5A | SJ-p2-1F | FQSSFVPLT | 63 | 41 nM | 912 pM | 1.5 nM |
| 20C2-6A | 4P1-22 | FQSSRVPLT | 64 | 18 nM | 544 pM | 714 pM |
| 20C2-6B | 4P1-22 | FQSSRVPLT | 64 | — | 53 pM | — |
| 20C2-7A | SJ-p2-27 | LNSTTVPLT | 73 | 128 nM | — | — |
| 20C2-8A | SJ-p2-39 | LQTTRVPLT | 80 | 14 nM | 140 pM | 376 pM |
| 20C2-8B | SJ-p2-39 | LQTTRVPLT | 80 | — | 46 pM | 64 pM |
| 20C2-9A | SJ-p2-51 | VQTSLVPLT | 94 | 36 nM | 241 pM | 420 pM |
| 20C2-10A | SJ-p3-33 | FQGSRLPVS | 61 | — | 84 nM | — |
| 20C2-11A | SJ-p3-6 | FQGSLLPLS | 98 | — | — | — |
| 20C2-12A | 4P1-32 | LQSSLVPLT | 76 | 617 nM | 1.5 nM | — |
| 20C2-13A | 4p1-20 | LQTSNVPLT | 79 | 94 nM | 3 nM | — |
| 20C2-18A | SJ-p1-9M | MQSSFVPLT | 86 | 126 nM | 1.8 nM | — |

TABLE 6-continued

| Name | Clone | LC-CDR3 | SEQ ID NO: | $K_D$ (Biotin-Aβ1-20) Fab | IgG1#1 | IgG1#2 |
|---|---|---|---|---|---|---|
| 20C2-20A | SJ-p3-15 | FQGSLFPPV | 58 | | 21 nM | |
| 20C2-22A | SJ-p2-66 | SQASRVPLT | 90 | | 2.3 nM | |
| 20C2-23A | 4P1-40 | HQSSKVPLT | 67 | | 649 pM | 1.5 nM |
| 20C2-24A | SJ-p2-44 | GQTTLVPLT | 65 | | 1.9 nM | |
| 20C2A | | FQGSLVPLT | 39 | | 27 nM | |
| 20C2B | | FQGSLVPLT | 39 | | 5.4 nM | |
| Mouse-20C2 | | FQGSLVPLT | 39 | 83 nM | 3.4 nM | |

TABLE 7

| Name | Clone | LC-CDR3 | SEQ ID NO: | $K_D$ (bADDL) Fab | IgG1#1 | IgG1#2 |
|---|---|---|---|---|---|---|
| 20C2-1A | SJ-p2-60 | FQASRVPLT | 52 | 85 nM | 75 pM | — |
| 20C2-2A | SJ-p1-18 | FQATRVPLT | 53 | 28 nM | 15 pM | 0.3 pM |
| 20C2-3A | SJ-p3-16 | FQGSFIPGT | 55 | — | 3.7 nM | — |
| 20C2-5A | SJ-p2-1F | FQSSFVPLT | 63 | 41 nM | 317 pM | 68 pM |
| 20C2-6A | 4P1-22 | FQSSRVPLT | 64 | 42 nM | 4.3 pM | 24 pM |
| 20C2-6B | 4P1-22 | FQSSRVPLT | 64 | — | 53 pM | — |
| 20C2-7A | SJ-p2-27 | LNSTTVPLT | 73 | 435 nM | — | — |
| 20C2-8A | SJ-p2-39 | LQTTRVPLT | 80 | 13 nM | 3 pM | 0.7 pM |
| 20C2-8B | SJ-p2-39 | LQTTRVPLT | 80 | — | 13 pM | 0.8 pM |
| 20C2-9A | SJ-p2-51 | VQTSLVPLT | 94 | 40 nM | — | 2 pM |
| 20C2-10A | SJ-p3-33 | FQGSRLPVS | 61 | — | 7.7 nM | |
| 20C2-11A | SJ-p3-6 | FQGSLLPLS | 98 | — | — | — |
| 20C2-12A | 4P1-32 | LQSSLVPLT | 76 | 238 nM | 15 pM | — |
| 20C2-13A | 4p1-20 | LQTSNVPLT | 79 | 567 nM | 764 pM | |
| 20C2-18A | SJ-p1-9M | MQSSFVPLT | 86 | 85 nM | 149 pM | |

TABLE 7-continued

| Name | Clone | LC-CDR3 | SEQ ID NO: | $K_D$ (bADDL) Fab | IgG1#1 | IgG1#2 |
|---|---|---|---|---|---|---|
| 20C2-20A | SJ-p3-15 | FQGSLFPPV | 58 | | 6.9 nM | |
| 20C2-22A | SJ-p2-66 | SQASRVPLT | 90 | | 198 pM | |
| 20C2-23A | 4P1-40 | HQSSKVPLT | 67 | | 85 pM | 66 pM |
| 20C2-24A | SJ-p2-44 | GQTTLVPLT | 65 | | 114 pM | |
| 20C2A | | FQGSLVPLT | 39 | | | |
| 20C2B | | FQGSLVPLT | 39 | | | |
| Mouse-20C2 | | FQGSLVPLT | 39 | 62 nM | 4.1 nM | |

Heavy Chain Maturation. The heavy chain of Hu20C2 was also subjected to optimization by generation of 3 libraries covering the heavy chain-CDR3 (RQLGLRSIDAMDY; SEQ ID NO:99). These libraries were designated 20C2B-39HC$_3$-1, 20C2B-39HC$_3$-2, and 20C2B-39HC$_3$-3 representing heavy chain CDR3 sequences of XXXXXRSIDAMDY (SEQ ID NO:100) and RQLGLRSIXXXXX (SEQ ID NO:101) and RQLGXXXXXAMDY (SEQ ID NO:102), respectively. Biotinylated reverse primers, 20C2HC$_3$-1 (SEQ ID NO:130), 20C2HC$_3$-2 (SEQ ID NO:133), and 20C2HC3-3 (SEQ ID NO:136) were used in combination with forward primer 20C2HC3F (SEQ ID NO:127) to generate the 3 libraries (see FIG. 5B). The libraries contained >$10^8$ functional diversity and covered all combinations of amino acids at every position randomized in each set (see Table 8).

TABLE 8

| Monoclonal Antibody | Diversity | Sequence | SEQ ID NO: |
|---|---|---|---|
| Hu20C2 | | RQLGLRSIDAMDY | 99 |
| 20C2B-39HC3-1 | $5.78 \times 10^8$ | XXXXXRSIDAMDY | 100 |
| 20C2B-39HC3-2 | $6.16 \times 10^8$ | RQLGLRSIXXXXX | 101 |
| 20C2B-39HC3-3 | $3.99 \times 10^8$ | RQLGXXXXXAMDY | 102 |

A total of 18 output plates from 4 rounds of panning were tested in a phage ELISA assay. A total of 1235 hits were found, of which 704 were sequenced. Based on BIACORE™ $K_D$ values of Fab fragments against biotinylated-Aβ1-20 and biotinylated ADDL (bADDL) antigens, as well as single-point BIACORE™ 3000 analysis (Table 9), a total of 6 Fab clones were converted into IgG1 and IgG2m4 using either CDR grafting or veneering humanization techniques. One of these 6 Fabs, designated 4a-A3, was isolated from library 20C2B -39HC$_3$-3 and carried 3 amino acid substitutions (RQLGTRGTDAMDY; SEQ ID NO:3) in the middle section of the heavy chain. As is evident from FIG. 2B, this heavy chain CDR3 sequence is that of Hu20C2A3.

TABLE 9

| Clone | bADDL Binding $K_D$ (M) | Aβ 1-20 Binding $K_D$ (M) | BIACORE™ 3000 Off-rate | Sequence | SEQ ID NO: |
|---|---|---|---|---|---|
| 4a-A3 | 8.23E-11 | 8.49E-10 | 6.65E-05 | RQLGTRGTDAMDY | 3 |
| 4b-A7 | 3.76E-10 | 1.72E-09 | 1.23E-04 | RQLGKLALDAMDY | 142 |
| 4b-H11 | 1.05E-09 | 1.33E-09 | 1.32E-04 | RQLGRRSVDAMDY | 8 |
| 20C28B | 1.10E-09 | 1.10E-09 | 8.76E-05 | RQLGLRSIDAMDY | 143 |
| 4a-F5 | 1.39E-09 | 1.33E-09 | 1.17E-04 | RQLGKLKTDAMDY | 7 |
| 4a-B2 | 1.92E-09 | 1.29E-09 | 1.13E-04 | RQLGARKTDAMDY | 5 |
| 4b-D8 | 2.23E-09 | 1.69E-09 | 1.45E-04 | RALSPRSIDAMDY | 4 |
| 4a-A4 | 2.67E-09 | 1.58E-09 | 1.20E-04 | RALSPRSIDAMDY | 4 |
| 4b-A1 | 2.87E-09 | 2.85E-09 | 1.23E-04 | RQLGPRKRDAMDY | 6 |
| 4a-A7 | 3.24E-09 | 2.21E-09 | 1.55E-04 | RQLGQRQTDAMDY | 144 |
| 4a-B9 | 3.44E-09 | 3.54E-09 | 1.94E-04 | RAIQPRSIDAMDY | 145 |
| 4a-B3 | 4.17E-09 | 3.64E-09 | 1.59E-04 | RQLGLRSIDAHTR | 146 |
| 4a-G10 | 4.52E-09 | 2.72E-09 | 1.78E-04 | RQLGQPSVDAMDY | 147 |
| 4a-E11 | 4.93E-09 | 3.48E-09 | 1.65E-04 | RQLGFQSTDAMDY | 148 |
| 4a-C9 | 8.43E-09 | 2.46E-09 | 1.75E-04 | RQLGQAGHDAMDY | 149 |
| 4a-D5 | 1.17E-09 | 3.91E-09 | 1.74E-04 | RQLGDNVADAMDY | 150 |
| 4a-E10 | 1.85E-08 | 3.60E-09 | 1.39E-04 | RQLGFQSTDAMDY | 148 |
| 4b-D4 | 1.86E-08 | 4.87E-09 | 1.89E-04 | RQLGMATPDAMDY | 151 |
| 4b-B10 | 6.28E-08 | 7.43E-09 | 1.81E-04 | RQLGAHWLDAMDY | 152 |
| 4b-A12 | 1.54E-07 | 1.01E-08 | 1.69E-04 | RQLGPEPQDAMDY | 153 |

EXAMPLE 5

Generation of IgG2m4 Antibodies

IgG2m4 antibody derivatives were prepared to decrease Fc receptor engagement, C1q binding, unwanted cytotoxicity or immunocomplex formation while maintaining both the long half-life and pharmacokinetic properties of a typical human antibody. The basic antibody format of IgG2m4 is that of IgG2, which has been shown to possess a superior half-life in experimental models (Zuckier, et al. (1994) *Cancer Suppl.* 73:794-799). The structure of IgG2 was modified to eliminate C1q binding, through selective incorporation of IgG4 sequences, while maintaining the typical low level of FcγR binding (Canfield and Morrison (1991) *J. Exp. Med.* 173: 1483-1491). This was achieved by using cross-over points wherein sequences of IgG2 and IgG4 were identical, thereby producing an antibody containing natural Fc sequences rather than any artificial mutational sequences. The advantages of using the instant IgG2m4 antibody which exhibits minimal effector-related activity is comparable to the deglycosylated antibody disclosed by Wilcock et al. ((2006) *J. Neurosci.* 26:5340-6).

The IgG2m4 form of the human antibody constant region was formed by selective incorporation of human IgG4 sequences into a standard human IgG2 constant region, as shown in FIG. 6. Conceptually, IgG2m4 resulted from a pair of chain-swaps within the CH2 domain as shown in FIG. 6. Four single mutations were made corresponding to sequences from IgG4. The Fc residues mutated in IgG2 included His268Gln, Val309Leu, Ala330Ser, and Pro331Ser, which minimized the potential for neoepitopes. The specific IgG4 amino acid residues placed into the IgG2 constant region are shown in Table 10, along with other alternatives from the basic structure.

TABLE 10

| Residue (Kabat numbering) | Residue in IgG2 | Residue in IgG4 | Residue in IgG2m4 | Alternative residue in IgG2m4 | Comment |
|---|---|---|---|---|---|
| 189 | Pro or Thr* | Pro | Thr | Pro | Key polymorphism of IgG2; Pro residue present in IGHG*01 allotype and Thr residue present in IGHG2*02 allotype[a,b]. |
| 268 | His | Gln | Gln | — | Change in the B/C loop known to be involved in FcγRII binding[c]. |
| 309 | Val | Leu or Val | Leu | Val | FcRn binding domain |
| 330 | Ala | Ser | Ser | — | Key residue for C1q binding[d]; also potentially involved in binding FcγRII and FcγRIII[e]. |
| 331 | Pro | Ser | Ser | — | Key residue for C1q binding[d,f] and FcγRI binding[g]; also potentially involved in binding FcγRII and FcγRIII[e]. |
| 397 | Met or Val* | Val | Met | Val | Val residue present in IGHG*01 allotype and Met |

TABLE 10-continued

| Residue (Kabat numbering) | Residue in IgG2 | Residue in IgG4 | Residue in IgG2m4 | Alternative residue in IgG2m4 | Comment |
|---|---|---|---|---|---|
| | | | | | residue present in IGHG2*02 allotype[a]. |

*Positions marked with an asterisk are subject to allelic variations.
[a]Hougs, et al. (2001) *Immunogenetics* 52(3-4): 242-8.
[b]WO 97/11971.
[c]Medgyesi, et al. (2004) *Eur. J. Immunol.* 34: 1127-1135.
[d]Tao, et al. (1991) *J. Exp. Med.* 173: 1025-1028.
[e]Armour, et al. (1999) *Eur. J. Immunol.* 29: 2613.
[f]Xu, et al. (1994) *J. Biol. Chem.* 269: 3469-3474.
[g]Canfield and Morrison (1991) *J. Exp. Med.* 173: 1483.

Human IgG1/kappa and IgG2m4/kappa versions of humanized Hu20C2 and Hu20C2A3 antibodies were constructed. The complete amino acid sequence of the light and heavy chain Hu20C2A3 IgG2m4 antibody is shown in FIGS. 7A and 7C.

EXAMPLE 6

Binding Affinity and Specificity of Humanized Anti-ADDL Antibodies

Affinity maturation was carried out to improve affinity and improve preferential binding to ADDL. To evaluate ADDL binding affinity of the humanized antibodies, BIACORE™ and titration ELISAs were conducted as disclosed herein. Briefly, Streptavidin-coated, 96-well microtiter plates (Sigma, St. Louis, Mo.) were coated with 10% biotinylated ADDL antigen (1 µM). A series of 2-fold dilutions of purified antibody, starting at 500 ng/mL was added to the ADDL captured plates and the plates were incubated for 2 hours at 25° C. After washing five times with PBS solution using a plate washer (Bio-Tek, Winooski, Va.), polyclonal goat anti-human kappa light chain antibody (Biomeda, Foster City, Calif.) was added at a 1/2000 dilution in 3% non-fat milk blocker and incubated at room temperature for 1 hour. A rabbit anti-goat IgG (H+L) HRP-conjugated (Bethyl Laboratories, Inc., Montgomery, Tex.) detection antibody was then added at a 1/2000 dilution in blocking solution and incubated for 1 hour at room temperature. After washing with PBS, HRP substrate, 3,3',5'5-tetramethylbenzidine (ready-to-use TMB; Sigma, St. Louis, Mo.) was added and the reaction was stopped after 10 minutes with 0.5 N $H_2SO_4$. Absorbance at wavelength of 450 nm was read in a plate reader (model VICTOR V; Perkin Elmer, Boston, Mass.) and data were processed using EXCEL® work sheet. Assay variations between plates were estimated within 20%.

The $K_D$ of Fab clone A3, as measured by BIACORE™, was 849 pM against biotinylated-Aβ1-20. The $K_D$ of the same Fab clone was 82 pM against bADDLs, indicating that the A3 Fab demonstrated preferential binding to ADDLs. When the clone was humanized by veneering and converted to a full IgG1 molecule or full IgG2m4 molecule (i.e., Hu20C2A3), the $K_D$ values against Aβ1-20 and ADDL were below the reliable detection limit of the BIACORE™ instrument, indicating a significant improvement of Hu20C2A3's binding equilibrium constant against Aβ1-20 and ADDL as compared to Hu20C2.

Figure 8B:
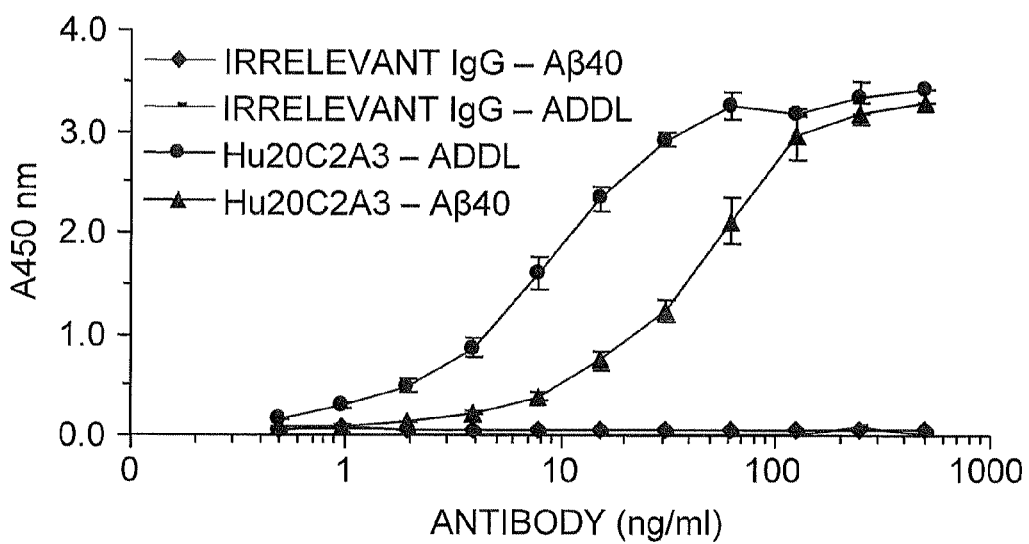

Hu20C2A3, which is the veneered version of clone A3 with an IgG2m4 isotype, was expressed in both CHO and Pichia. The two sources of Hu20C2A3 were evaluated for their ability to interact with Aβ monomer and ADDLs by ELISA. As shown in FIG. 8, Hu20C2A3 produced in either CHO (FIG. 8A) or Pichia (FIG. 8B) showed preferential ADDL binding versus Aβ40 monomer binding (6-fold). Binding constants (IgGk$_{50}$ values) as determined from these curves yielded values of 64 pM and 376 pM for ADDLs and Aβmonomer, respectively for Hu20C2A3 produced in Pichia and 58 pM and 361 pM for ADDLs and Aβ monomer, respectively for Hu20C2A3 produced in CHO cells.

EXAMPLE 7

Inhibition of ADDL Binding to Neurons Using Humanized Anti-ADDL Antibodies

Figure 9:
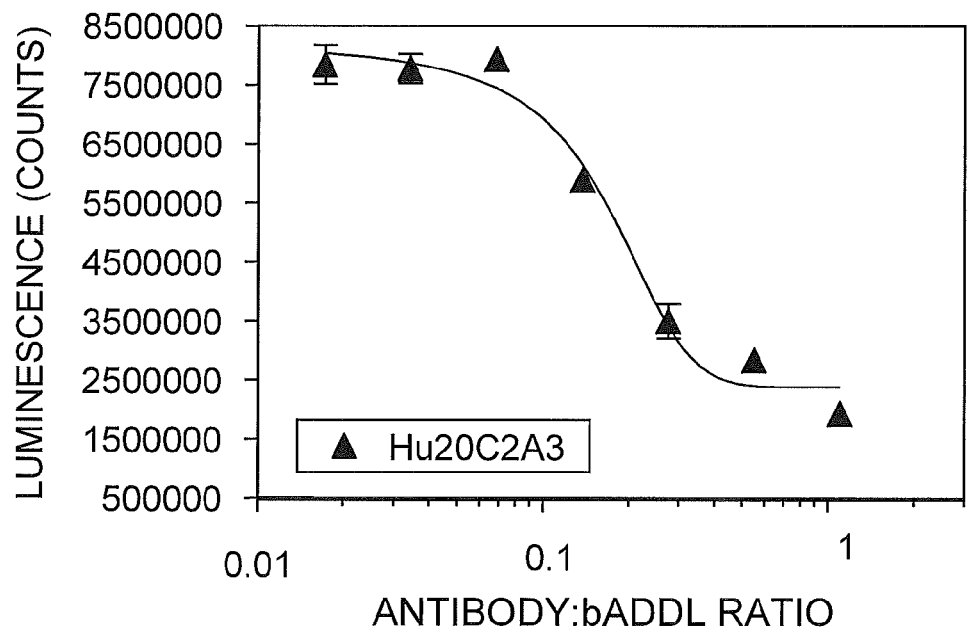
FIG. 9 shows Hu20C2A3 inhibition of bADDL binding to primary hippocampal neurons.

The humanized anti-ADDL antibodies were further evaluated for their ability to block ADDL binding to primary hippocampal neurons using the methods disclosed herein. Hu20C2A3 antibody, or PBS as a control, was mixed at various molar ratios with bADDLs and incubated for one hour at 37° C. on a slow rotator. After the preincubation, the antibody/bADDL preparations were added to primary neuron cultures and incubated for an additional hour at 37° C. At the end of the incubation period, the bADDLs/antibody mixture was removed and the plates washed six times with media. The cells were then fixed in 4% paraformaldehyde for ten minutes at room temperature, the solution removed, fresh fixative added, and the cells fixed for an additional ten minutes. The cells were permeabilized with 4% paraformaldehyde containing 0.1% TRITON™ X-100 (2 times, each for ten minutes at room temperature), washed six times in PBS and then treated with 10% BSA in PBS for one hour at 37° C. Alkaline phosphatase-conjugated streptavidin (1:1,500 in 1% BSA; Molecular Probes, Eugene, Oreg.) was then added to the cells for one hour at room temperature. The cells were rinsed six times with PBS, the alkaline phosphatase substrate (CDP-STAR® with SAPPHIRE-II™; Applied Biosystems, Foster City, Calif.) added to the cells and incubated for thirty minutes prior to determining the luminescence on a LJL Luminometer (Analyst AD; LJL Biosystems, Sunnyvale, Calif.). In this analysis, Hu20C2A3 was found to effectively inhibit bADDL binding to neurons at a sub-stoichiometric antibody to peptide ratio (EC$_{50}$=0.16; FIG. 9).

The inhibition of bADDL binding indicated that Hu20C2A3 interacts with ADDLs in a biologically relevant manner. To demonstrate that Hu20C2A3 interacts with ADDLs relevant to the human Alzheimer's Disease condition, the ability of biotinylated Hu20C2A3 to immuno-label Aβ containing plaques in human Alzheimer's Disease brain tissue was evaluated. Immunohistochemical localization showed avid labeling of Aβ in both dense core and diffuse plaques in human Alzheimer's Disease brain tissue. The specificity of this binding was demonstrated by a loss of immunoreactivity following pre-incubation with increasing ADDL:antibody amounts. Similar to Hu20C2, Hu20C2A3, efficiently labels both dense core and diffuse Aβ deposits.

EXAMPLE 8

Thermal Stability of Hu20C2A3

Figure 10:
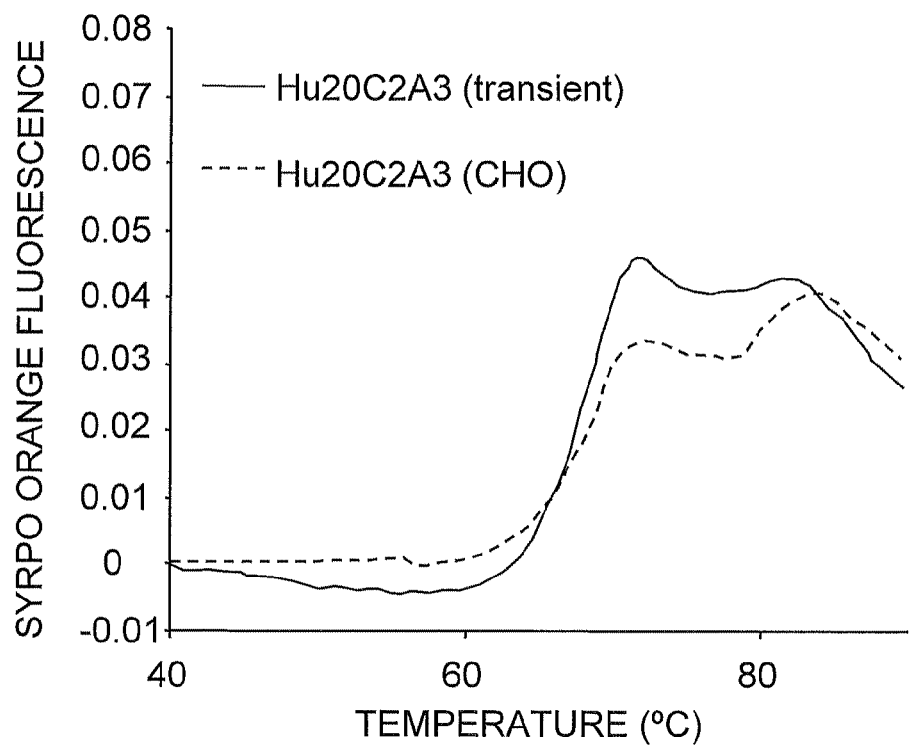
FIG. 10 shows fluorescent thermal melt analysis of Hu20C2A3.

An evaluation of the protein stability of Hu20C2A3 was assessed using SEC-HPLC, fluorescent thermal melt analysis, and particle size analysis. Fluorescent thermal melt analysis indicated that Fc and Fab unfolding transitions occurred at approximately 70° C. and 80° C., respectively, consistent with acceptable inherent protein stability (FIG. 10).

EXAMPLE 9

In Vivo Pharmacodynamic and Efficacy Analysis

Figure 11:
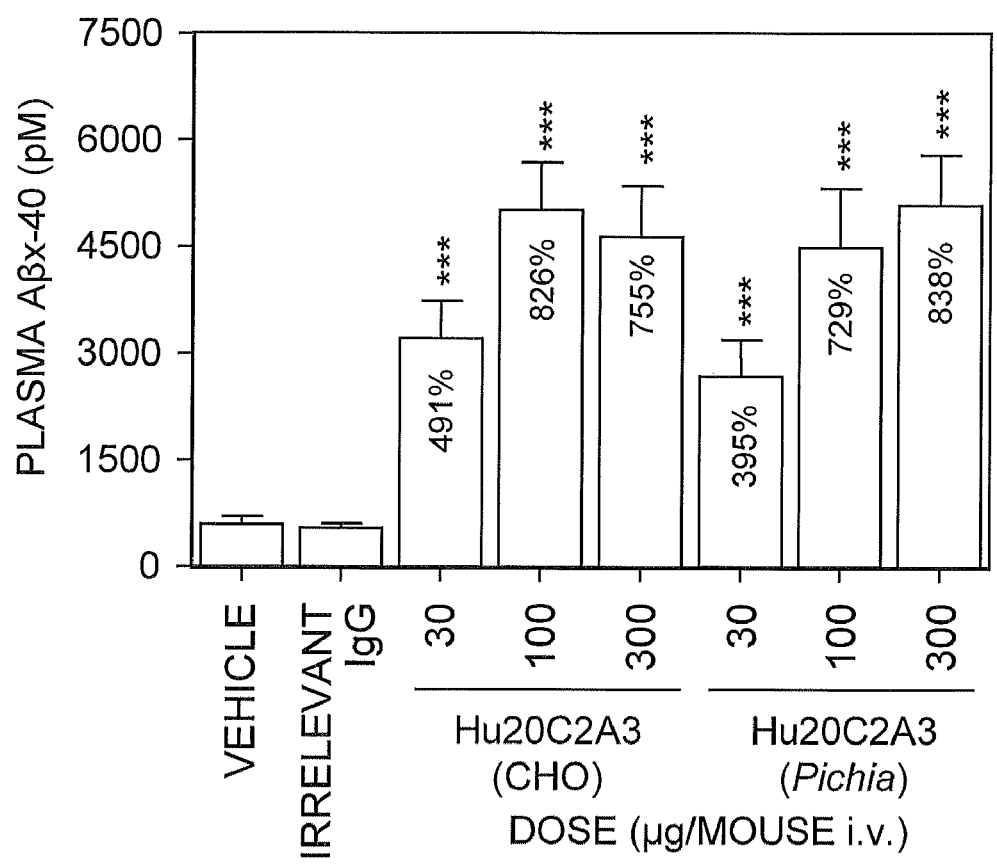
FIG. 11 shows plasma Aβx-40 levels (pM) of APP-YAC mice following intravenous injection of Hu20C2A3, irrelevant control or vehicle. Hu20C2A3 was prepared by stable transfection of CHO cells or *Pichia*. Aβx-40 was determined using a 4G8/G2-10 ELISA. ***, p<0.001 by Tukey-Kramer HSD post-hoc testing. Error bars=SEM; N=6/group.

The prior art indicates that systemic injection of monoclonal anti-Aβ antibodies can increase plasma levels of Aβ acutely, whereas measurable lowering of brain Aβ requires chronic administration. It has been suggested that passive immunization in species with measurable Aβ results in an elevation of plasma Aβ due to a change in the equilibrium of Aβ between brain and peripheral compartments. This "peripheral sink" ultimately leads to lowering of brain Aβ. However, cognitive improvement has been observed in animals following acute antibody administration prior to notable changes in brain Aβ, indicating that changes in brain Aβ may occur in some form prior to a time point where these changes can be measured using known techniques. Alternately, elevations of plasma Aβ could be explained by a stabilization of peripheral Aβ following administration of antibody. Regardless of the interpretation, it has been established that early plasma elevations are a prerequisite for subsequent lowering of brain Aβ in animal models. Thus, the effect of Hu20C2A3 antibodies on plasma Aβ elevations were utilized as an indicator of target engagement. Following infusion of Hu20C2A3 at doses of 30, 100 and 300 µg/mouse IV, significant and robust increases in plasma Aβx-40 were observed relative to the non-relevant antibody (8B4) control group 4 hours post-injection (FIG. 11). The observed increases in plasma Aβx-40 for CHO-derived material were 491% (30 µg, p>0.001), 826% (100 µg, p<0.001), and 755% (300 µg, p<0.001) of the 8B4 levels. Similarly, the increases in plasma Aβx-40 for *Pichia*-derived material were 395% (30 µg, p>0.001), 729% (100 µg, p<0.001), and 838% (300 µg, p<0.001) of the 8B4 levels.

What is claimed is:

1. An isolated antibody, or an antigen binding fragment of the antibody, that binds amyloid β-derived diffusible ligands comprising:
    (a) a light chain variable region comprising,
        (i) a CDR1 of SEQ ID NO:154,
        (ii) a CDR2 of SEQ ID NO:155, and
        (iii) a CDR3 of SEQ ID NO:80; and
    (b) a heavy chain variable region comprising,
        (i) a CDR1 of SEQ ID NO:156,
        (ii) a CDR2 of SEQ ID NO:157, and
        (iii) a CDR3 of SEQ ID NO:3.

2. The isolated antibody of claim 1, further comprising a heavy chain constant region of SEQ ID NO:137.

3. The isolated antibody of claim 1, wherein the antibody is a monoclonal antibody.

4. A pharmaceutical composition comprising the antibody or antigen binding fragment of claim 1 in admixture with a pharmaceutically acceptable carrier.

5. A kit for detecting Aβ-derived diffusible ligands comprising the antibody or antigen binding fragment of claim 1.

6. A method for attenuating binding of Aβ-derived diffusible ligands to a neuron comprising contacting the neuron with the antibody or antigen binding fragment of claim 1 so that binding of Aβ-derived diffusible ligands to the neuron is attenuated.

7. A method for inhibiting assembly of Aβ-derived diffusible ligands comprising contacting a sample containing amyloid β 1-42 peptides with the antibody or antigen binding fragment of claim 1 thereby inhibiting assembly of A β-derived diffusible ligands.

8. A method for inhibiting the phosphorylation of tau protein at Ser202/Thr205 comprising contacting a sample containing a tau protein with the antibody or antigen binding fragment of claim 1 thereby inhibiting the phosphorylation of tau protein at Ser202/Thr205.

9. A method for attenuating the symptoms of a disease associated with Aβ-derived diffusible ligands comprising administering an effective amount of the pharmaceutical composition of claim 4.

10. A method for identifying a putative therapeutic agent that attenuates the binding of Aβ-derived diffusible ligands to neurons comprising
    (a) contacting a composition comprising a neuron with Aβ-derived diffusible ligands in the presence of an agent;
    (b) contacting the composition with the antibody or antigen binding fragment of claim 1; and
    (c) detecting the amount of antibody or antigen binding fragment bound to the neuron in the presence of the agent, wherein a decrease in the amount of antibody or antigen binding fragment bound in the presence of the agent as compared to the amount of antibody bound in the absence of the agent indicates that the agent is a putative therapeutic agent for attenuating binding of Aβ-derived diffusible ligands to neurons.

11. A method for detecting Aβ-derived diffusible ligands in a sample comprising contacting the sample with the antibody or antigen binding fragment of claim 1 and determining the presence of a complex comprising the Aβ-derived diffusible ligands and antibody or antigen binding fragment.

12. A method for diagnosing a disease associated with Aβ-derived diffusible ligands comprising contacting a biological sample with the antibody or antigen binding fragment of claim 1 and determining the presence of a complex comprising the Aβ-derived diffusible ligands and the antibody or antigen binding fragment wherein the presence of the complex is diagnostic of a disease associated with Aβ-derived diffusible ligands.

* * * * *

SEQUENCE LISTING

```
<160> NUMBER OF SEQ ID NOS: 157

<210> SEQ ID NO 1
<211> LENGTH: 6
<212> TYPE: PRT
<213> ORGANISM: Homo sapiens

<400> SEQUENCE: 1

Glu Phe Arg His Asp Ser
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic CDR3 peptide
<220> FEATURE:
<221> NAME/KEY: MISC_FEATURE
<222> LOCATION: (1)..(1)
<223> OTHER INFORMATION: Xaa denotes Phe or Leu
<220> FEATURE:
<221> NAME/KEY: MISC_FEATURE
<222> LOCATION: (3)..(3)
<223> OTHER INFORMATION: Xaa denotes Ala or Thr

<400> SEQUENCE: 2

Xaa Gln Xaa Thr Arg Val Pro Leu Thr
1               5

<210> SEQ ID NO 3
<211> LENGTH: 13
<212> TYPE: PRT
<213> ORGANISM: Artificial Sequence
<220> FEATURE:
<223> OTHER INFORMATION: Synthetic CDR3 peptide

<400> SEQUENCE: 3

Arg Gln Leu Gly Thr Arg Gly Thr Asp Ala Met Asp Tyr
1               5                   10
```

```
<210> SEQ ID NO 4
<211> LENGTH: 13
<212> TYPE: PRT
<213> ORGANISM: Artificial Sequence
<220> FEATURE:
<223> OTHER INFORMATION: Synthetic CDR3 peptide

<400> SEQUENCE: 4

Arg Ala Leu Ser Pro Arg Ser Ile Asp Ala Met Asp Tyr
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic CDR3 peptide

<400> SEQUENCE: 5

Arg Gln Leu Gly Ala Arg Lys Thr Asp Ala Met Asp Tyr
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthetic CDR3 peptide

<400> SEQUENCE: 6

Arg Gln Leu Gly Pro Arg Lys Arg Asp Ala Met Asp Tyr
1               5                   10

<210> SEQ ID NO 7
<211> LENGTH: 13
<212> TYPE: PRT
<213> ORGANISM: Artificial Sequence
<220> FEATURE:
<223> OTHER INFORMATION: Synthetic CDR3 peptide

<400> SEQUENCE: 7

Arg Gln Leu Gly Lys Leu Lys Thr Asp Ala Met Asp Tyr
1               5                   10

<210> SEQ ID NO 8
<211> LENGTH: 13
<212> TYPE: PRT
<213> ORGANISM: Artificial Sequence
<220> FEATURE:
<223> OTHER INFORMATION: Synthetic CDR3 peptide

<400> SEQUENCE: 8

Arg Gln Leu Gly Arg Arg Ser Val Asp Ala Met Asp Tyr
1               5                   10

<210> SEQ ID NO 9
<211> LENGTH: 13
<212> TYPE: PRT
<213> ORGANISM: Artificial Sequence
<220> FEATURE:
<223> OTHER INFORMATION: Synthetic CDR3 peptide
<220> FEATURE:
<221> NAME/KEY: MISC_FEATURE
<222> LOCATION: (2)..(2)
<223> OTHER INFORMATION: Xaa denotes Gln or Ala
<220> FEATURE:
<221> NAME/KEY: MISC_FEATURE
<222> LOCATION: (4)..(4)
```

```
<223> OTHER INFORMATION: Xaa denotes Ser or Gly
<220> FEATURE:
<221> NAME/KEY: MISC_FEATURE
<222> LOCATION: (5)..(5)
<223> OTHER INFORMATION: Xaa denotes Pro, Ala, Lys, Arg, or Thr
<220> FEATURE:
<221> NAME/KEY: MISC_FEATURE
<222> LOCATION: (6)..(6)
<223> OTHER INFORMATION: Xaa denotes Lys or Arg
<220> FEATURE:
<221> NAME/KEY: MISC_FEATURE
<222> LOCATION: (7)..(7)
<223> OTHER INFORMATION: Xaa denotes Gly, Ser, or Lys
<220> FEATURE:
<221> NAME/KEY: MISC_FEATURE
<222> LOCATION: (8)..(8)
<223> OTHER INFORMATION: Xaa denotes Val, Thr, Ile or Arg

<400> SEQUENCE: 9

Arg Xaa Leu Xaa Xaa Xaa Xaa Xaa Asp Ala Met Asp Tyr
1               5                   10

<210> SEQ ID NO 10
<211> LENGTH: 10
<212> TYPE: PRT
<213> ORGANISM: Artificial Sequence
<220> FEATURE:
<223> OTHER INFORMATION: Synthetic peptide

<400> SEQUENCE: 10

Leu Pro Val Thr Pro Gly Glu Pro Ala Ser
1               5                   10

<210> SEQ ID NO 11
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 11
gatctctaga tgaagattgc ctgttaggct gttggtgctg                          40

<210> SEQ ID NO 12
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 12
gatctctaga tggagwcaga cacactcctg ytatgggtg                           39

<210> SEQ ID NO 13
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 13
gatctctaga tgagtgtgct cactcaggtc ctggsgttg                           39

<210> SEQ ID NO 14
<211> LENGTH: 42
<212> TYPE: DNA
<213> ORGANISM: Artificial Sequence
<220> FEATURE:
<223> OTHER INFORMATION: Synthetic oligonucleotide
```

-continued

<400> SEQUENCE: 14
gatctctaga tgaggrcccc tgctcagwtt yttggmwtct tg                42

<210> SEQ ID NO 15
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 15
gatctctaga tggatttwca ggtgcagatt wtcagcttc                    39

<210> SEQ ID NO 16
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 16
gatctctaga tgaggtkcyy tgytsaycty ctctgrgg                     38

<210> SEQ ID NO 17
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 17
gatctctaga tgggcwtcaa agatggagtc acakwyycwg g                 41

<210> SEQ ID NO 18
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 18
gatctctaga tgtggggayc tktttycmmt ttttcaatg                    39

<210> SEQ ID NO 19
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 19
gatctctaga tggtrtccwc asctcagttc cttg                         34

<210> SEQ ID NO 20
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 20
gatctctaga tgtatatatg tttgttgtct atttct                       36

<210> SEQ ID NO 21
<211> LENGTH: 37
<212> TYPE: DNA

```
<213> ORGANISM: Artificial Sequence
<220> FEATURE:
<223> OTHER INFORMATION: Synthetic oligonucleotide

<400> SEQUENCE: 21
gatctctaga tggaagcccc agctcagctt ctcttcc                              37

<210> SEQ ID NO 22
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 22
gatcgagctc actggatggt gggaagatgg                                      30

<210> SEQ ID NO 23
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 23
gatctctaga tgaaatgcag ctggggcats ttcttc                               36

<210> SEQ ID NO 24
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 24
gatctctaga tgggatggag ctrtatcats ytctt                                35

<210> SEQ ID NO 25
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 25
gatctctaga tgaagwtgtg gttaaactgg gttttt                               36

<210> SEQ ID NO 26
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 26
gatctctaga tgractttgg gytcagcttg rttt                                 34

<210> SEQ ID NO 27
<211> LENGTH: 41
<212> TYPE: DNA
<213> ORGANISM: Artificial Sequence
<220> FEATURE:
<223> OTHER INFORMATION: Synthetic oligonucleotide

<400> SEQUENCE: 27
gatctctaga tgggactcca ggcttcaatt tagttttcct t                         41
```

```
<210> SEQ ID NO 28
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 28
gatctctaga tggcttgtcy ttrgsgctrc tcttctgc                              38

<210> SEQ ID NO 29
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 29
gatctctaga tggratggag ckggrgtctt tmtctt                                36

<210> SEQ ID NO 30
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 30
gatctctaga tgagagtgct gattcttttg tg                                    32

<210> SEQ ID NO 31
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 31
gatctctaga tggmttgggt gtggamcttg cttattcctg                            40

<210> SEQ ID NO 32
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 32
gatctctaga tgggcagact taccattctc attcctg                               37

<210> SEQ ID NO 33
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 33
gatctctaga tggattttgg gctgattttt tttattg                               37

<210> SEQ ID NO 34
<211> LENGTH: 36
<212> TYPE: DNA
<213> ORGANISM: Artificial Sequence
<220> FEATURE:
<223> OTHER INFORMATION: Synthetic oligonucleotide
```

```
<400> SEQUENCE: 34
gatctctaga tgatggtgtt aagtcttctg tacctg                                36

<210> SEQ ID NO 35
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 35
gcatcgagct ccagtggata gacagatggg gg                                    32

<210> SEQ ID NO 36
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 36
gcatcgagct ccagtggata gaccgatggg gg                                    32

<210> SEQ ID NO 37
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 37
gcatcgagct ccagtggatg agctgatggg gg                                    32

<210> SEQ ID NO 38
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 38
gcatcgagct ccaagggata gacagatggg gc                                    32

<210> SEQ ID NO 39
<211> LENGTH: 9
<212> TYPE: PRT
<213> ORGANISM: Artificial Sequence
<220> FEATURE:
<223> OTHER INFORMATION: Synthetic peptide

<400> SEQUENCE: 39

Phe Gln Gly Ser Leu Val Pro Leu Thr
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: Xaa denotes any amino acid residue

<400> SEQUENCE: 40

Xaa Xaa Xaa Xaa Xaa Val Pro Leu Thr
```

<210> SEQ ID NO 41
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(9)
<223> OTHER INFORMATION: Xaa denotes any amino acid residue

<400> SEQUENCE: 41

Phe Gln Gly Ser Xaa Xaa Xaa Xaa Xaa
1               5

<210> SEQ ID NO 42
<211> LENGTH: 9
<212> TYPE: PRT
<213> ORGANISM: Artificial Sequence
<220> FEATURE:
<223> OTHER INFORMATION: Synthetic peptide

<400> SEQUENCE: 42

Ala Asp Thr Thr His Val Pro Leu Thr
1               5

<210> SEQ ID NO 43
<211> LENGTH: 9
<212> TYPE: PRT
<213> ORGANISM: Artificial Sequence
<220> FEATURE:
<223> OTHER INFORMATION: Synthetic peptide

<400> SEQUENCE: 43

Ala His Ser Thr Phe Val Pro Leu Thr
1               5

<210> SEQ ID NO 44
<211> LENGTH: 9
<212> TYPE: PRT
<213> ORGANISM: Artificial Sequence
<220> FEATURE:
<223> OTHER INFORMATION: Synthetic peptide

<400> SEQUENCE: 44

Ala Gln Ala Ser Phe Val Pro Leu Thr
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic peptide

<400> SEQUENCE: 45

Ala Gln Ala Thr Lys Val Pro Leu Thr
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic peptide

<400> SEQUENCE: 46

```
Ala Gln Ser Ser Lys Val Pro Leu Thr
1               5
```

<210> SEQ ID NO 47
<211> LENGTH: 9
<212> TYPE: PRT
<213> ORGANISM: Artificial Sequence
<220> FEATURE:
<223> OTHER INFORMATION: Synthetic peptide

<400> SEQUENCE: 47

```
Ala Gln Ser Thr Leu Val Pro Leu Thr
1               5
```

<210> SEQ ID NO 48
<211> LENGTH: 9
<212> TYPE: PRT
<213> ORGANISM: Artificial Sequence
<220> FEATURE:
<223> OTHER INFORMATION: Synthetic peptide

<400> SEQUENCE: 48

```
Phe Ala Ala Ser Ser Val Pro Leu Thr
1               5
```

<210> SEQ ID NO 49
<211> LENGTH: 9
<212> TYPE: PRT
<213> ORGANISM: Artificial Sequence
<220> FEATURE:
<223> OTHER INFORMATION: Synthetic peptide

<400> SEQUENCE: 49

```
Phe Glu Ser Thr Tyr Val Pro Leu Thr
1               5
```

<210> SEQ ID NO 50
<211> LENGTH: 9
<212> TYPE: PRT
<213> ORGANISM: Artificial Sequence
<220> FEATURE:
<223> OTHER INFORMATION: Synthetic peptide

<400> SEQUENCE: 50

```
Phe Glu Ser Ser Arg Val Pro Leu Thr
1               5
```

<210> SEQ ID NO 51
<211> LENGTH: 9
<212> TYPE: PRT
<213> ORGANISM: Artificial Sequence
<220> FEATURE:
<223> OTHER INFORMATION: Synthetic peptide

<400> SEQUENCE: 51

```
Phe Asn Ala Thr Trp Val Pro Leu Thr
1               5
```

<210> SEQ ID NO 52
<211> LENGTH: 9
<212> TYPE: PRT
<213> ORGANISM: Artificial Sequence
<220> FEATURE:
<223> OTHER INFORMATION: Synthetic peptide

<400> SEQUENCE: 52

```
Phe Gln Ala Ser Arg Val Pro Leu Thr
```

<210> SEQ ID NO 53
<211> LENGTH: 9
<212> TYPE: PRT
<213> ORGANISM: Artificial Sequence
<220> FEATURE:
<223> OTHER INFORMATION: Synthetic peptide

<400> SEQUENCE: 53

Phe Gln Ala Thr Arg Val Pro Leu Thr
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic peptide

<400> SEQUENCE: 54

Phe Gln Gly Ser Phe Ile Gly Leu Ser
1               5

<210> SEQ ID NO 55
<211> LENGTH: 9
<212> TYPE: PRT
<213> ORGANISM: Artificial Sequence
<220> FEATURE:
<223> OTHER INFORMATION: Synthetic peptide

<400> SEQUENCE: 55

Phe Gln Gly Ser Phe Ile Pro Gly Thr
1               5

<210> SEQ ID NO 56
<211> LENGTH: 9
<212> TYPE: PRT
<213> ORGANISM: Artificial Sequence
<220> FEATURE:
<223> OTHER INFORMATION: Synthetic peptide

<400> SEQUENCE: 56

Phe Gln Gly Ser Phe Leu Pro Pro Ser
1               5

<210> SEQ ID NO 57
<211> LENGTH: 9
<212> TYPE: PRT
<213> ORGANISM: Artificial Sequence
<220> FEATURE:
<223> OTHER INFORMATION: Synthetic peptide

<400> SEQUENCE: 57

Phe Gln Gly Ser Phe Leu Pro Gln Leu
1               5

<210> SEQ ID NO 58
<211> LENGTH: 9
<212> TYPE: PRT
<213> ORGANISM: Artificial Sequence
<220> FEATURE:
<223> OTHER INFORMATION: Synthetic peptide

<400> SEQUENCE: 58

Phe Gln Gly Ser Leu Phe Pro Pro Val
1               5

```
<210> SEQ ID NO 59
<211> LENGTH: 9
<212> TYPE: PRT
<213> ORGANISM: Artificial Sequence
<220> FEATURE:
<223> OTHER INFORMATION: Synthetic peptide

<400> SEQUENCE: 59

Phe Gln Gly Ser Leu Phe Ser Pro Ser
1               5

<210> SEQ ID NO 60
<211> LENGTH: 9
<212> TYPE: PRT
<213> ORGANISM: Artificial Sequence
<220> FEATURE:
<223> OTHER INFORMATION: Synthetic peptide

<400> SEQUENCE: 60

Phe Gln Gly Ser Arg Ile Pro Ile Ser
1               5

<210> SEQ ID NO 61
<211> LENGTH: 9
<212> TYPE: PRT
<213> ORGANISM: Artificial Sequence
<220> FEATURE:
<223> OTHER INFORMATION: Synthetic peptide

<400> SEQUENCE: 61

Phe Gln Gly Ser Arg Leu Pro Val Ser
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide

<400> SEQUENCE: 62

Phe Gln Gly Ser Arg Val Pro Leu Val
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide

<400> SEQUENCE: 63

Phe Gln Ser Ser Phe Val Pro Leu Thr
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide

<400> SEQUENCE: 64

Phe Gln Ser Ser Arg Val Pro Leu Thr
1               5

<210> SEQ ID NO 65
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 65

Gly Gln Thr Thr Leu Val Pro Leu Thr
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide

<400> SEQUENCE: 66

His Glu Ser Thr Leu Val Pro Leu Thr
1               5

<210> SEQ ID NO 67
<211> LENGTH: 9
<212> TYPE: PRT
<213> ORGANISM: Artificial Sequence
<220> FEATURE:
<223> OTHER INFORMATION: Synthetic peptide

<400> SEQUENCE: 67

His Gln Ser Ser Lys Val Pro Leu Thr
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide

<400> SEQUENCE: 68

Ile Gln Thr Ser Leu Val Pro Leu Thr
1               5

<210> SEQ ID NO 69
<211> LENGTH: 9
<212> TYPE: PRT
<213> ORGANISM: Artificial Sequence
<220> FEATURE:
<223> OTHER INFORMATION: Synthetic peptide

<400> SEQUENCE: 69

Ile Gln Ala Ala Leu Val Pro Leu Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic peptide

<400> SEQUENCE: 70

Leu Gln Ser Ser Phe Val Pro Leu Thr
1               5

<210> SEQ ID NO 71
<211> LENGTH: 9
<212> TYPE: PRT
```

<213> ORGANISM: Artificial Sequence
<220> FEATURE:
<223> OTHER INFORMATION: Synthetic peptide

<400> SEQUENCE: 71

Leu Glu Thr Ser Arg Val Pro Leu Thr
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic peptide

<400> SEQUENCE: 72

Leu Ala Ser Ser His Val Pro Leu Thr
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic peptide

<400> SEQUENCE: 73

Leu Asn Ser Thr Thr Val Pro Leu Thr
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic peptide

<400> SEQUENCE: 74

Leu Gln Ser Lys Ser Val Pro Leu Thr
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic peptide

<400> SEQUENCE: 75

Leu Gln Ser Val Arg Val Pro Leu Thr
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic peptide

<400> SEQUENCE: 76

Leu Gln Ser Ser Leu Val Pro Leu Thr
1               5

<210> SEQ ID NO 77
<211> LENGTH: 9
<212> TYPE: PRT
<213> ORGANISM: Artificial Sequence
<220> FEATURE:

<223> OTHER INFORMATION: Synthetic peptide

<400> SEQUENCE: 77

Leu Gln Thr Gly Arg Val Pro Leu Thr
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic peptide

<400> SEQUENCE: 78

Leu Gln Thr Ser Phe Val Pro Leu Thr
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic peptide

<400> SEQUENCE: 79

Leu Gln Thr Ser Asn Val Pro Leu Thr
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic peptide

<400> SEQUENCE: 80

Leu Gln Thr Thr Arg Val Pro Leu Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic peptide

<400> SEQUENCE: 81

Leu Ser Ser Thr Phe Val Pro Leu Thr
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic peptide

<400> SEQUENCE: 82

Leu Ser Ser Thr His Val Pro Leu Thr
1               5

<210> SEQ ID NO 83
<211> LENGTH: 9
<212> TYPE: PRT
<213> ORGANISM: Artificial Sequence
<220> FEATURE:
<223> OTHER INFORMATION: Synthetic peptide

```
<400> SEQUENCE: 83

Leu Thr Ser Ser Ala Val Pro Leu Thr
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic peptide

<400> SEQUENCE: 84

Leu Val Ser Ser Leu Val Pro Leu Thr
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic peptide

<400> SEQUENCE: 85

Met Glu Thr Ala Asn Val Pro Leu Thr
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic peptide

<400> SEQUENCE: 86

Met Gln Ser Ser Phe Val Pro Leu Thr
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic peptide

<400> SEQUENCE: 87

Met Gln Ser Ser Leu Val Pro Leu Thr
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic peptide

<400> SEQUENCE: 88

Met Gln Thr Ser Lys Val Pro Leu Thr
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic peptide

<400> SEQUENCE: 89
```

```
Ser Gln Ala Arg Met Val Pro Leu Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic peptide

<400> SEQUENCE: 90

Ser Gln Ala Ser Arg Val Pro Leu Thr
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic peptide

<400> SEQUENCE: 91

Thr Gln Ser Thr Gln Val Pro Leu Thr
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic peptide

<400> SEQUENCE: 92

Val Cys Ala Thr Phe Val Pro Leu Thr
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic peptide

<400> SEQUENCE: 93

Val Gln Ser Ser Ala Val Pro Leu Thr
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic peptide

<400> SEQUENCE: 94

Val Gln Thr Ser Leu Val Pro Leu Thr
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic peptide

<400> SEQUENCE: 95

Val Gln Thr Ser Val Val Pro Leu Thr
1               5
```

-continued

<210> SEQ ID NO 96
<211> LENGTH: 9
<212> TYPE: PRT
<213> ORGANISM: Artificial Sequence
<220> FEATURE:
<223> OTHER INFORMATION: Synthetic peptide

<400> SEQUENCE: 96

Val Gln Thr Thr Ala Val Pro Leu Thr
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic peptide

<400> SEQUENCE: 97

Leu Gln Thr Ala Arg Val Pro Leu Thr
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic peptide

<400> SEQUENCE: 98

Phe Gln Gly Ser Leu Leu Pro Leu Ser
1               5

<210> SEQ ID NO 99
<211> LENGTH: 13
<212> TYPE: PRT
<213> ORGANISM: Artificial Sequence
<220> FEATURE:
<223> OTHER INFORMATION: Synthetic peptide

<400> SEQUENCE: 99

Arg Gln Leu Gly Leu Arg Ser Ile Asp Ala Met Asp Tyr
1               5                   10

<210> SEQ ID NO 100
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(5)
<223> OTHER INFORMATION: Xaa denotes any amino acid residue

<400> SEQUENCE: 100

Xaa Xaa Xaa Xaa Xaa Arg Ser Ile Asp Ala Met Asp Tyr
1               5                   10

<210> SEQ ID NO 101
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (9)..(13)

<223> OTHER INFORMATION: Xaa denotes any amino acid residue

<400> SEQUENCE: 101

Arg Gln Leu Gly Leu Arg Ser Ile Xaa Xaa Xaa Xaa Xaa
1               5                   10

<210> SEQ ID NO 102
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (5)..(9)
<223> OTHER INFORMATION: Xaa denotes any amino acid residue

<400> SEQUENCE: 102

Arg Gln Leu Gly Xaa Xaa Xaa Xaa Xaa Ala Met Asp Tyr
1               5                   10

<210> SEQ ID NO 103
<211> LENGTH: 459
<212> TYPE: DNA
<213> ORGANISM: Mus musculus

<400> SEQUENCE: 103
tgggcagact taccattctc attcctgctg ctgattgtcc ctgcatatgt cttgtcccaa      60
gttactctaa aagagtctgg ccctgggata ttgaagccct cacagaccct cagtctgact    120
tgttctctct ctgggttttc actgagcact tctggtatgg gtgtaggctg gtttcgtcag    180
ccttcaggga agggtctgga gtggctggca cacatttggt gggatgatga aagtccctat    240
aatccatccc tgaagagccg gctcacaatc tccaagtata cctctagaaa ccaggttttc    300
ctcacgatca ccagtgtgga cactgcagat actgccactt actattgtgc tcgaagacaa    360
ctcggactaa gatcaattga tgctatggac tactggggtc aaggaacctc agtcaccgtc    420
tcctcagcca aaacgacacc cccatctgtc tatccactg                           459

<210> SEQ ID NO 104
<211> LENGTH: 435
<212> TYPE: DNA
<213> ORGANISM: Mus musculus

<400> SEQUENCE: 104
agattgcctg ttaggctgtt ggtgctgatg ttctggattc ctgcttccac cagtgatgtt      60
ttgatgaccc aaactcctct ctccctgcct gtcagtcttg agatcaagc ctccatctct     120 tgcagatcta gtcagagcat tctacatagt aatggaaaca cctatttaga gtggtacctg    180
cagaaaccag gccagtctcc aaagctcctg atctacaaag tttccaaccg attttctggg    240
gtcccagaca ggttcagtgg cagtggatca gggacagatt cacactcaa gatcagcaga    300 gtggaggctg aggatctggg agtttattac tgttttcaag gttcacttgt tccgctcacg    360
ttcggtgctg ggaccaagct ggagctgaaa cgggctgatg ctgcaccaac tgtatccatc    420
ttcccaccat ccagt                                                    435

<210> SEQ ID NO 105
<211> LENGTH: 123
<212> TYPE: PRT
<213> ORGANISM: Mus musculus

<400> SEQUENCE: 105

Gln Val Thr Leu Lys Glu Ser Gly Pro Gly Ile Leu Lys Pro Ser Gln
1               5                   10                  15

Thr Leu Ser Leu Thr Cys Ser Leu Ser Gly Phe Ser Leu Ser Thr Ser
            20                  25                  30

Gly Met Gly Val Gly Trp Phe Arg Gln Pro Ser Gly Lys Gly Leu Glu
        35                  40                  45

Trp Leu Ala His Ile Trp Trp Asp Asp Lys Ser Tyr Asn Pro Ser
    50                  55                  60

Leu Lys Ser Arg Leu Thr Ile Ser Lys Tyr Thr Ser Arg Asn Gln Val
65                  70                  75                  80

Phe Leu Thr Ile Thr Ser Val Asp Thr Ala Asp Thr Ala Thr Tyr Tyr
                85                  90                  95

Cys Ala Arg Arg Gln Leu Gly Leu Arg Ser Ile Asp Ala Met Asp Tyr
            100                 105                 110

Trp Gly Gln Gly Thr Ser Val Thr Val Ser Ser
            115                 120

<210> SEQ ID NO 106
<211> LENGTH: 120
<212> TYPE: PRT
<213> ORGANISM: Homo sapiens

<400> SEQUENCE: 106

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Ile Tyr Tyr Tyr Tyr Gly Met Asp Val Trp Gly Gln
            100                 105                 110

Gly Thr Thr Val Thr Val Ser Ser
            115                 120

<210> SEQ ID NO 107
<211> LENGTH: 123
<212> TYPE: PRT
<213> ORGANISM: Artificial Sequence
<220> FEATURE:
<223> OTHER INFORMATION: Synthetic antibody

<400> SEQUENCE: 107

Gln Val Thr Leu Lys Glu Ser Gly Pro Ala Leu Val Lys Pro Thr Gln
1               5                   10                  15

Thr Leu Thr Leu Thr Cys Thr Leu Ser Gly Phe Ser Leu Ser Thr Ser
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Lys Ser Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gln Leu Gly Leu Arg Ser Ile Asp Ala Met Asp Tyr
            100                 105                 110

Trp Gly Gln Gly Thr Thr Val Thr Val Ser Ser
        115                 120

<210> SEQ ID NO 108
<211> LENGTH: 123
<212> TYPE: PRT
<213> ORGANISM: Artificial Sequence
<220> FEATURE:
<223> OTHER INFORMATION: Synthetic antibody

<400> SEQUENCE: 108

Gln Val Thr Leu Lys Glu Ser Gly Pro Gly Leu Leu Lys Pro Thr Gln
1               5                   10                  15

Thr Leu Thr Leu Thr Cys Thr Leu Ser Gly Phe Ser Leu Ser Thr Ser
            20                  25                  30

Gly Met Gly Val Gly Trp Phe Arg Gln Pro Pro Gly Lys Gly Leu Glu
        35                  40                  45

Trp Leu Ala His Ile Trp Trp Asp Asp Lys Ser Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Ala Arg Arg Gln Leu Gly Thr Arg Gly Thr Asp Ala Met Asp Tyr
            100                 105                 110

Trp Gly Gln Gly Thr Thr Val Thr Val Ser Ser
        115                 120

<210> SEQ ID NO 109
<211> LENGTH: 112
<212> TYPE: PRT
<213> ORGANISM: Mus musculus

<400> SEQUENCE: 109

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser Leu Val Pro Leu Thr Phe Gly Ala Gly Thr Lys Leu Glu Leu Lys
            100                 105                 110

<210> SEQ ID NO 110
<211> LENGTH: 112
<212> TYPE: PRT
<213> ORGANISM: Homo sapiens

<400> SEQUENCE: 110

```
Asp Ile Val Met Thr Gln Thr Pro Leu Ser Leu Ser Val Thr Pro Gly
1               5                   10                  15

Gln Pro Ala Ser Ile Ser Cys Lys Ser Ser Gln Ser Leu Leu His Ser
            20                  25                  30

Asp Gly Lys Thr Tyr Leu Tyr Trp Tyr Leu Gln Lys Pro Gly Gln Ser
        35                  40                  45

Pro Gln Leu Leu Ile Tyr Glu Val Ser Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Gly
                85                  90                  95

Ile His Leu Pro Tyr Thr Phe Gly Gln Gly Thr Lys Leu Glu Ile Lys
                100                 105                 110
```

<210> SEQ ID NO 111
<211> LENGTH: 112
<212> TYPE: PRT
<213> ORGANISM: Artificial Sequence
<220> FEATURE:
<223> OTHER INFORMATION: Synthetic antibody

<400> SEQUENCE: 111

```
Asp Val Val Met Thr Gln Ser Pro Leu Ser Leu Pro Val Thr Pro Gly
1               5                   10                  15

Glu Pro Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Thr
                85                  90                  95

Thr Arg Val Pro Leu Thr Phe Gly Gln Gly Thr Lys Leu Glu Ile Lys
                100                 105                 110
```

<210> SEQ ID NO 112
<211> LENGTH: 112
<212> TYPE: PRT
<213> ORGANISM: Artificial Sequence
<220> FEATURE:
<223> OTHER INFORMATION: Synthetic antibody

<400> SEQUENCE: 112

```
Asp Val Val Met Thr Gln Thr Pro Leu Ser Leu Pro Val Thr Pro Gly
1               5                   10                  15

Gln Pro Ala Ser Ile Ser Cys Arg Ser Ser Gln Ser Ile Leu His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Leu Gln Thr
                85                  90                  95
```

Thr Arg Val Pro Leu Thr Phe Gly Gln Gly Thr Lys Leu Glu Ile Lys
                100                 105                 110

<210> SEQ ID NO 113
<211> LENGTH: 369
<212> TYPE: DNA
<213> ORGANISM: Artificial Sequence
<220> FEATURE:
<223> OTHER INFORMATION: Synthetic nucleic acid molecule

<400> SEQUENCE: 113
caggtgaccc tgaaggagtc tggccctgcc ctggtgaagc ccacccagac cctgaccctg      60
acctgcacct tctctggctt cagcctgagc acctctggca tgggcgtggg ctggatccgg     120
cagcccctg gcaaggccct ggagtggctg gcccacatct ggtgggacga cgacaagtcc      180
tacaacccca gcctgaagag ccggctgacc atcagcaagg acaccagcaa gaaccaggtg     240
gtgctgacca tgaccaacat ggaccctgtg gacacagcca cctactactg tgcccggcgg     300
cagctgggcc tgcggagcat tgatgccatg gactactggg gccagggcac cacagtgaca     360
gtgtccagc                                                              369

<210> SEQ ID NO 114
<211> LENGTH: 369
<212> TYPE: DNA
<213> ORGANISM: Artificial Sequence
<220> FEATURE:
<223> OTHER INFORMATION: Synthetic nucleic acid molecule

<400> SEQUENCE: 114
caggtgaccc tgaaggagtc tggccctgcc ctggtgaagc ccacccagac cctgaccctg      60
acctgcaccc tgtctggctt cagcctgagc acctctggca tgggcgtggg ctggatccgg     120
cagcccctg gcaaggccct ggagtggctg gcccacatct ggtgggacga cgacaagtcc      180
tacaacccca gcctgaagag ccggctgacc atcagcaagg acaccagcaa gaaccaggtg     240
gtgctgacca tgaccaacat ggaccctgtg gacacagcca cctactactg tgcccggcgg     300
cagctgggcc tgcggagcat tgatgccatg gactactggg gccagggcac cacagtgaca     360
gtgtccagc                                                              369

<210> SEQ ID NO 115
<211> LENGTH: 336
<212> TYPE: DNA
<213> ORGANISM: Artificial Sequence
<220> FEATURE:
<223> OTHER INFORMATION: Synthetic nucleic acid molecule

<400> SEQUENCE: 115
gatgtggtga tgacccagag ccccctgtcc ctgcctgtga cccctggcga gcctgccagc      60
atctcctgcc ggagctccca gagcatcctg cactccaatg caacaccta cctggagtgg     120
tacctgcaga gcctggccca gagccccag ctgctgatct acaaggtgtc caaccggttc      180
tccggcgtgc ctgaccggtt cagcggctcc ggcagcggca cagacttcac cctgaagatc     240
agccgggtgg aggctgagga tgtgggcgtc tactactgct ccagggcag cctggtgccc     300
ctgacctttg gccagggcac caagctggag atcaag                                336

<210> SEQ ID NO 116
<211> LENGTH: 482
<212> TYPE: PRT
<213> ORGANISM: Artificial Sequence
<220> FEATURE:

<223> OTHER INFORMATION: Synthetic polypeptide

<400> SEQUENCE: 116

```
Met Lys Lys Thr Ala Ile Ala Ile Ala Val Ala Leu Ala Gly Phe Ala
1               5                   10                  15

Thr Val Ala Gln Ala Ala Leu Glu Gln Val Thr Leu Lys Glu Ser Gly
            20                  25                  30

Pro Ala Leu Val Lys Pro Thr Gln Thr Leu Thr Leu Thr Cys Thr Phe
        35                  40                  45

Ser Gly Phe Ser Leu Ser Thr Ser Gly Met Gly Val Gly Trp Ile Arg
50                  55                  60

Gln Pro Pro Gly Lys Ala Leu Glu Trp Leu Ala His Ile Trp Trp Asp
65                  70                  75                  80

Asp Asp Lys Ser Tyr Asn Pro Ser Leu Lys Ser Arg Leu Thr Ile Ser
                85                  90                  95

Lys Asp Thr Ser Lys Asn Gln Val Val Leu Thr Met Thr Asn Met Asp
            100                 105                 110

Pro Val Asp Thr Ala Thr Tyr Tyr Cys Ala Arg Arg Gln Leu Gly Leu
        115                 120                 125

Arg Ser Ile Asp Ala Met Asp Tyr Trp Gly Gln Gly Thr Thr Val Thr
130                 135                 140

Val Ser Ser Ala Ser Thr Lys Gly Pro Ser Val Phe Pro Leu Ala Pro
145                 150                 155                 160

Ser Ser Lys Ser Thr Ser Gly Gly Thr Ala Ala Leu Gly Cys Leu Val
                165                 170                 175

Lys Asp Tyr Phe Pro Glu Pro Val Thr Val Ser Trp Asn Ser Gly Ala
            180                 185                 190

Leu Thr Ser Gly Val His Thr Phe Pro Ala Val Leu Gln Ser Ser Gly
        195                 200                 205

Leu Tyr Ser Leu Ser Ser Val Val Thr Val Pro Ser Ser Ser Leu Gly
210                 215                 220

Thr Gln Thr Tyr Ile Cys Asn Val Asn His Lys Pro Ser Asn Thr Lys
225                 230                 235                 240

Val Asp Lys Arg Val Glu Pro Lys Ser Cys Thr Ser Gly His His His
                245                 250                 255

His His His Gly Gly Glu Gln Lys Leu Ile Ser Glu Glu Asp Leu Gly
            260                 265                 270

Gly Pro Phe Val Cys Glu Tyr Gln Gly Gln Ser Ser Asp Leu Pro Gln
        275                 280                 285

Pro Pro Val Asn Ala Gly Gly Gly Ser Gly Gly Gly Ser Gly Gly Gly
290                 295                 300

Ser Glu Gly Gly Gly Ser Glu Gly Gly Gly Ser Glu Gly Gly Gly Ser
305                 310                 315                 320

Glu Gly Gly Gly Ser Gly Gly Gly Ser Gly Gly Asp Phe Asp Tyr
            325                 330                 335

Glu Lys Met Ala Asn Ala Asn Lys Gly Ala Met Thr Glu Asn Ala Asp
        340                 345                 350

Glu Asn Ala Leu Gln Ser Asp Ala Lys Gly Lys Leu Asp Ser Val Ala
        355                 360                 365

Thr Asp Tyr Gly Ala Ala Ile Asp Gly Phe Ile Gly Asp Val Ser Gly
        370                 375                 380

Leu Ala Asn Gly Asn Gly Ala Thr Gly Asp Phe Ala Gly Ser Asn Ser
385                 390                 395                 400

Gln Met Ala Gln Val Gly Asp Gly Asp Asn Ser Pro Leu Met Asn Asn
```

```
                      405                 410                 415
Phe Arg Gln Tyr Leu Pro Ser Leu Pro Gln Ser Val Glu Cys Arg Pro
            420                 425                 430

Tyr Val Phe Gly Ala Gly Lys Pro Tyr Glu Phe Ser Ile Asp Cys Asp
            435                 440                 445

Lys Ile Asn Leu Phe Arg Gly Val Phe Ala Phe Leu Leu Tyr Val Ala
            450                 455                 460

Thr Phe Met Tyr Val Phe Ser Thr Phe Ala Asn Ile Leu Arg Asn Lys
465                 470                 475                 480

Glu Ser

<210> SEQ ID NO 117
<211> LENGTH: 481
<212> TYPE: PRT
<213> ORGANISM: Artificial Sequence
<220> FEATURE:
<223> OTHER INFORMATION: Synthetic polypeptide

<400> SEQUENCE: 117

Met Lys Lys Thr Ala Ile Ala Ile Ala Val Ala Leu Ala Gly Phe Ala
1               5                   10                  15

Thr Val Ala Gln Ala Ala Leu Glu Gln Val Thr Leu Lys Glu Ser Gly
            20                  25                  30

Pro Ala Leu Val Lys Pro Thr Gln Thr Leu Thr Leu Thr Cys Thr Leu
            35                  40                  45

Ser Gly Phe Ser Leu Ser Thr Ser Gly Met Gly Val Gly Trp Ile Arg
        50                  55                  60

Gln Pro Pro Gly Lys Ala Leu Glu Trp Leu Ala His Ile Trp Trp Asp
65                  70                  75                  80

Asp Asp Lys Ser Tyr Asn Pro Ser Leu Lys Ser Arg Leu Thr Ile Ser
                85                  90                  95

Lys Asp Thr Ser Lys Asn Gln Val Val Leu Thr Met Thr Asn Met Asp
            100                 105                 110

Pro Val Asp Thr Ala Thr Tyr Tyr Cys Ala Arg Arg Gln Leu Gly Leu
            115                 120                 125

Arg Ser Ile Asp Ala Met Asp Tyr Trp Gly Gln Gly Thr Thr Val Thr
        130                 135                 140

Val Ser Ala Ser Thr Lys Gly Pro Ser Val Phe Pro Leu Ala Pro Ser
145                 150                 155                 160

Ser Lys Ser Thr Ser Gly Gly Thr Ala Ala Leu Gly Cys Leu Val Lys
                165                 170                 175

Asp Tyr Phe Pro Glu Pro Val Thr Val Ser Trp Asn Ser Gly Ala Leu
            180                 185                 190

Thr Ser Gly Val His Thr Phe Pro Ala Val Leu Gln Ser Ser Gly Leu
        195                 200                 205

Tyr Ser Leu Ser Ser Val Val Thr Val Pro Ser Ser Leu Gly Thr
        210                 215                 220

Gln Thr Tyr Ile Cys Asn Val Asn His Lys Pro Ser Asn Thr Lys Val
225                 230                 235                 240

Asp Lys Arg Val Glu Pro Lys Ser Cys Thr Ser Gly His His His His
                245                 250                 255

His His Gly Gly Glu Gln Lys Leu Ile Ser Glu Glu Asp Leu Gly Gly
            260                 265                 270

Pro Phe Val Cys Glu Tyr Gln Gly Gln Ser Ser Asp Leu Pro Gln Pro
        275                 280                 285
```

```
Pro Val Asn Ala Gly Gly Ser Gly Gly Ser Gly Gly Gly Ser
    290                 295                 300

Glu Gly Gly Ser Glu Gly Gly Ser Glu Gly Gly Ser Glu
305                 310                 315                 320

Gly Gly Gly Ser Gly Gly Ser Gly Ser Asp Phe Asp Tyr Glu
                325                 330                 335

Lys Met Ala Asn Ala Asn Lys Gly Ala Met Thr Glu Asn Ala Asp Glu
                340                 345                 350

Asn Ala Leu Gln Ser Asp Ala Lys Gly Lys Leu Asp Ser Val Ala Thr
            355                 360                 365

Asp Tyr Gly Ala Ala Ile Asp Gly Phe Ile Gly Asp Val Ser Gly Leu
    370                 375                 380

Ala Asn Gly Asn Gly Ala Thr Gly Asp Phe Ala Gly Ser Asn Ser Gln
385                 390                 395                 400

Met Ala Gln Val Gly Asp Gly Asp Asn Ser Pro Leu Met Asn Asn Phe
                405                 410                 415

Arg Gln Tyr Leu Pro Ser Leu Pro Gln Ser Val Glu Cys Arg Pro Tyr
            420                 425                 430

Val Phe Gly Ala Gly Lys Pro Tyr Glu Phe Ser Ile Asp Cys Asp Lys
    435                 440                 445

Ile Asn Leu Phe Arg Gly Val Phe Ala Phe Leu Leu Tyr Val Ala Thr
450                 455                 460

Phe Met Tyr Val Phe Ser Thr Phe Ala Asn Ile Leu Arg Asn Lys Glu
465                 470                 475                 480

Ser

<210> SEQ ID NO 118
<211> LENGTH: 243
<212> TYPE: PRT
<213> ORGANISM: Artificial Sequence
<220> FEATURE:
<223> OTHER INFORMATION: Synthetic polypeptide

<400> SEQUENCE: 118

Met Lys Tyr Leu Leu Pro Thr Ala Ala Ala Gly Leu Leu Leu Leu Ala
1               5                   10                  15

Ala Gln Pro Ala Met Ala Ser Arg Asp Val Val Met Thr Gln Ser Pro
                20                  25                  30

Leu Ser Leu Pro Val Thr Pro Gly Glu Pro Ala Ser Ile Ser Cys Arg
            35                  40                  45

Ser Ser Gln Ser Ile Leu His Ser Asn Gly Asn Thr Tyr Leu Glu Trp
        50                  55                  60

Tyr Leu Gln Lys Pro Gly Gln Ser Pro Gln Leu Leu Ile Tyr Lys Val
65                  70                  75                  80

Ser Asn Arg Phe Ser Gly Val Pro Asp Arg Phe Ser Gly Ser Gly Ser
                85                  90                  95

Gly Thr Asp Phe Thr Leu Lys Ile Ser Arg Val Glu Ala Glu Asp Val
            100                 105                 110

Gly Val Tyr Tyr Cys Phe Gln Gly Ser Leu Val Pro Leu Thr Phe Gly
        115                 120                 125

Gln Gly Thr Lys Leu Glu Ile Lys Arg Thr Val Ala Ala Pro Ser Val
    130                 135                 140

Phe Ile Phe Pro Pro Ser Asp Glu Gln Leu Lys Ser Gly Thr Ala Ser
145                 150                 155                 160

Val Val Cys Leu Leu Asn Asn Phe Tyr Pro Arg Glu Ala Lys Val Gln
                165                 170                 175
```

```
Trp Lys Val Asp Asn Ala Leu Gln Ser Gly Asn Ser Gln Glu Ser Val
            180                 185                 190

Thr Glu Gln Asp Ser Lys Asp Ser Thr Tyr Ser Leu Ser Ser Thr Leu
        195                 200                 205

Thr Leu Ser Lys Ala Asp Tyr Glu Lys His Lys Val Tyr Ala Cys Glu
    210                 215                 220

Val Thr His Gln Gly Leu Ser Ser Pro Val Thr Lys Ser Phe Asn Arg
225                 230                 235                 240

Gly Glu Cys

<210> SEQ ID NO 119
<211> LENGTH: 5458
<212> TYPE: DNA
<213> ORGANISM: Artificial Sequence
<220> FEATURE:
<223> OTHER INFORMATION: Synthetic nucleic acid molecule

<400> SEQUENCE: 119
gcccaatacg caaaccgcct ctccccgcgc gttggccgat tcattaatgc agctggcacg     60
acaggtttcc cgactggaaa gcgggcagtg agcgcaacgc aattaatgtg agttagctca    120
ctcattaggc accccaggct ttacacttta tgcttccggc tcgtatgttg tgtggaattg    180
tgagcggata caatttcac acaagatcta gctattccag agattacgca aattctattt     240
caaggagaca gtcataatga atacctgct gccgactgca gctgctggtc tgctgctgct     300
ggcggcccag ccggctatgg cttctagaga tgtggtgatg acccagagcc cctgtccct     360 gcctgtgacc cctggcgagc tgccagcat ctcctgccgg agctcccaga gcatcctgca    420
ctccaatggc aacacctacc tggagtggta cctgcagaag cctggccaga gcccccagct    480
gctgatctac aaggtgtcca accggttctc cggcgtgcct gaccggttca gcggctccgg    540
cagcggcaca gacttcaccc tgaagatcag ccgggtggag gctgaggatg tgggcgtcta    600
ctactgcttc cagggcagcc tggtgcccct gaccttttggc cagggcacca agctggagat    660
caagcgtacg gtggctgcac catctgtctt catcttcccg ccatctgatg agcagttgaa    720
atctggaact gcctctgttg tgtgcctgct gaataacttc tatcccagag aggccaaagt    780
acagtggaag gtggataacg ccctccaatc gggtaactcc caggagagtg tcacagagca    840
ggacagcaag gacagcacct acagcctcag cagcaccctg acgctgagca agcagacta    900 cgagaaacac aaagtctacg cctgcgaagt cacccatcag ggcctgagct cgcccgtcac    960
aaagagcttc aacaggggag agtgttaaca attgctagaa ttgtgagcgg ataacaattt   1020
cagcaggtcg agttcttgat aacgaggcgt aaaaaatgaa aaagacagct atcgcgattg   1080
cagtggcact ggctggtttc gctaccgtgg cccaggcggc cctcgagcag gtgaccctga   1140
aggagtctgg ccctgccctg gtgaagccca cccagaccct gaccctgacc tgcaccttct   1200
ctggcttcag cctgagcacc tctggcatgg gcgtgggctg gatccggcag ccccctggca   1260
aggccctgga gtggctggcc cacatctggt gggacgacga caagtcctac aaccccagcc   1320
tgaagagccg gctgaccatc agcaaggaca ccagcaagaa ccaggtggtg ctgaccatga   1380
ccaacatgga ccctgtggac acagccacct actactgtgc ccggcggcag ctgggcctgc   1440
ggagcattga tgccatggac tactgggcc agggcaccac agtgacagtg tccagcgcct   1500
ccaccaaggg cccatcggtc ttccccctgg caccctcctc caagagcacc tctggggca   1560 cagcggccct gggctgcctg gtcaaggact acttccccga accggtgacg gtgtcgtgga   1620
actcaggcgc cctgaccagc ggcgtgcaca ccttcccggc tgtcctacag tcctcaggac   1680
```

```
tctactccct cagcagcgtg gtgaccgtgc cctccagcag cttgggcacc cagacctaca    1740
tctgcaacgt gaatcacaag cccagcaaca ccaaggtgga caagagagtt gagcccaaat    1800
cttgtactag tggccaccac caccatcacc atggcggtga acaaaaactc atctcagaag    1860
aggatctggg tggttagcca ttcgtttgtg aatatcaagg ccaatcgtct gacctgcctc    1920
aacctcctgt caatgctggc ggcggctctg gtggtggttc tggtggcggc tctgagggtg    1980
gcggctctga gggtggcggt tctgagggtg gcggctctga gggtggcggt tccggtggcg    2040
gctccggttc cggtgatttt gattatgaaa aaatggcaaa cgctaataag ggggctatga    2100
ccgaaaatgc cgatgaaaac gcgctacagt ctgacgctaa aggcaaactt gattctgtcg    2160
ctactgatta cggtgctgct atcgatggtt tcattggtga cgtttccggc cttgctaatg    2220
gtaatggtgc tactggtgat tttgctggct ctaattccca aatggctcaa gtcggtgacg    2280
gtgataattc acctttaatg aataatttcc gtcaatattt accttctttg cctcagtcgg    2340
ttgaatgtcg cccttatgtc tttggcgctg gtaaaccata tgaattttct attgattgtg    2400
acaaaataaa cttattccgt ggtgtctttg cgtttctttt atatgttgcc acctttatgt    2460
atgtattttc gacgtttgct aacatactgc gtaataagga gtcttaagct agctggccgt    2520
cgttttacaa cgtcgtgact gggaaaaccc tggcgttacc caacttaatc gccttgcagc    2580
acatccccct ttcgccagct ggcgtaatag cgaagaggcc cgcaccgatc gcccttccca    2640
acagttgcgc agcctgaatg gcgaatggcg attccgttgc aatggctggc ggtaatattg    2700
ttctggatat accagcaag gccgatagtt tgagttcttc tactcaggca agtgatgtta    2760
ttactaatca agaagtatt gcgacaacgg ttaatttgcg tgatggacag actcttttac    2820
tcggtggcct cactgattat aaaaacactt ctcaggattc tggcgtaccg ttcctgtcta    2880 aaatccettt aatcggcctc ctgtttagct cccgctctga ttctaacgag gaaagcacgt    2940
tatacgtgct cgtcaaagca accatagtac gcgccctgta gcggcgcatt aagcgcggcg    3000
ggtgtggtgg ttacgcgcag cgtgaccgct acacttgcca gcgccctagc gcccgctcct    3060
ttcgctttct tcccttcctt tctcgccacg ttcgccggct ttccccgtca gctctaaat    3120 cgggggctcc ctttagggtt ccgatttagt gctttacggc acctcgaccc caaaaaactt    3180
gattagggtg atggttcacg tagtgggcca tcgccctgat agacggtttt tcgccctttg    3240
acgttggagt ccacgttctt taatagtgga ctcttgttcc aaactggaac aacactcaac    3300
cctatctcgg tctattcttt tgatttataa gggattttgc cgatttcggc ctattggtta    3360
aaaaatgagc tgatttaaca aaaatttaac gcgaatttta acaaaatatt aacgtttaca    3420
atttaaatat ttgcttatac aatcttcctg ttttggggc ttttctgatt atcaaccggg    3480
gtacatatga ttgacatgct agttttacga ttaccgttca tcgcaggtgg cacttttcgg    3540
ggaaatgtgc gcggaacccc tatttgttta ttttctaaa tacattcaaa tatgtatccg    3600
ctcatgagac aataaccctg ataaatgctt caataatatt gaaaaggaa gagtatgagt    3660 attcaacatt tccgtgtcgc ccttattccc ttttttgcgg cattttgcct tcctgttttt    3720
gctcacccag aaacgctggt gaaagtaaaa gatgctgaag atcagttggg tgcacgagtg    3780
ggttacatcg aactggatct caacagcggt aagatccttg agtttttcg ccccgaagaa    3840 cgttttccaa tgatgagcac ttttaaagtt ctgctatgtg gcgcggtatt atcccgtatt    3900
gacgccgggc aagagcaact cggtcgccgc atacactatt ctcagaatga cttggttgag    3960
tactcaccag tcacagaaaa gcatcttacg gatggcatga cagtaagaga attatgcagt    4020
gctgccataa ccatgagtga taacactgcg gccaacttac ttctgacaac gatcggagga    4080
```

```
ccgaaggagc taaccgcttt tttgcacaac atgggggatc atgtaactcg ccttgatcgt     4140
tgggaaccgg agctgaatga agccatacca aacgacgagc gtgacaccac gatgcctgta     4200
gcaatggcaa caacgttgcg caaactatta actggcgaac tacttactct agcttcccgg     4260
caacaattaa tagactggat ggaggcggat aaagttgcag gaccacttct gcgctcggcc     4320
cttccggctg gctggtttat tgctgataaa tctggagccg gtgagcgtgg gtctcgcggt     4380
atcattgcag cactggggcc agatggtaag ccctcccgta tcgtagttat ctacacgacg     4440
gggagtcagg caactatgga tgaacgaaat agacagatcg ctgagatagg tgcctcactg     4500
attaagcatt ggtaactgtc agaccaagtt tactcatata ctttagat tgatttaaaa       4560 cttcattttt aatttaaaag gatctaggtg aagatccttt ttgataatct catgaccaaa     4620
atcccttaac gtgagttttc gttccactga gcgtcagacc ccgtagaaaa gatcaaagga     4680
tcttcttgag atccttttttt ctgcgcgta atctgctgct tgcaaacaaa aaaaccaccg     4740
ctaccagcgg tggtttgttt gccggatcaa gagctaccaa ctcttttccc gaaggtaact     4800
ggcttcagca gagcgcagat accaaatact gtccttctag tgtagccgta gttaggccac     4860
cacttcaaga actctgtagc accgcctaca tacctcgctc tgctaatcct gttaccagtg     4920
gctgctgcca gtggcgataa gtcgtgtctt accgggttgg actcaagacg atagttaccg     4980
gataaggcgc agcggtcggg ctgaacgggg gttcgtgca cacagcccag cttggagcga     5040
acgacctaca ccgaactgag atacctacag cgtgagctat gagaaagcgc cacgcttccc     5100
gaagggagaa aggcggacag gtatccggta agcggcaggg tcggaacagg agagcgcacg     5160
agggagcttc caggggaaa cgcctggtat ctttatagtc ctgtcgggtt tcgccacctc     5220
tgacttgagc gtcgattttt gtgatgctcg tcaggggggc ggagcctatg gaaaaacgcc     5280
agcaacgcgg cctttttacg gttcctggcc ttttgctggc cttttgctca catgttcttt     5340
cctgcgttat cccctgattc tgtggataac cgtattaccg cctttgagtg agctgatacc     5400
gctcgccgca gccgaacgac cgagcgcagc gagtcagtga gcgaggaagc ggaagagc      5458
```

<210> SEQ ID NO 120
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 120

```
ctatggcttc tagagatgtg gtgatg                                             26
```

<210> SEQ ID NO 121
<211> LENGTH: 398
<212> TYPE: DNA
<213> ORGANISM: Artificial Sequence
<220> FEATURE:
<223> OTHER INFORMATION: Synthetic nucleic acid molecule

<400> SEQUENCE: 121

```
agctgctggt ctgctgctgc tggcggccca gccggctatg gcttctagag atgtggtgat       60
gacccagagc cccctgtccc tgcctgtgac ccctggcgag cctgccagca tctcctgccg      120
gagctcccag agcatcctgc actccaatgg caacacctac ctggagtggt acctgcagaa      180
gcctggccag agcccccagc tgctgatcta caaggtgtcc aaccggttct ccggcgtgcc      240
tgaccggttc agcggctccg gcagcggcac agacttcacc ctgaagatca gccgggtgga      300
ggctgaggat gtgggcgtct actactgctt ccagggcagc ctggtgcccc tgacctttgg      360
```

```
ccagggcacc aagctggaga tcaagcgtac ggtggctg                              398
```

<210> SEQ ID NO 122
<211> LENGTH: 398
<212> TYPE: DNA
<213> ORGANISM: Artificial Sequence
<220> FEATURE:
<223> OTHER INFORMATION: Synthetic nucleic acid molecule
<220> FEATURE:
<221> NAME/KEY: misc_feature
<222> LOCATION: (329)..(330)
<223> OTHER INFORMATION: n is a, c, g, or t
<220> FEATURE:
<221> NAME/KEY: misc_feature
<222> LOCATION: (332)..(333)
<223> OTHER INFORMATION: n is a, c, g, or t
<220> FEATURE:
<221> NAME/KEY: misc_feature
<222> LOCATION: (335)..(336)
<223> OTHER INFORMATION: n is a, c, g, or t
<220> FEATURE:
<221> NAME/KEY: misc_feature
<222> LOCATION: (338)..(339)
<223> OTHER INFORMATION: n is a, c, g, or t
<220> FEATURE:
<221> NAME/KEY: misc_feature
<222> LOCATION: (341)..(342)
<223> OTHER INFORMATION: n is a, c, g, or t

<400> SEQUENCE: 122

```
agctgctggt ctgctgctgc tggcggccca gccggctatg gcttctagag atgtggtgat    60
gacccagagc ccctgtccc tgcctgtgac cctggcgag cctgccagca tctcctgccg     120
gagctcccag agcatcctgc actccaatgg caacacctac ctggagtggt acctgcagaa   180
gcctggccag agccccagc tgctgatcta caaggtgtcc aaccggttct ccggcgtgcc    240
tgaccggttc agcggctccg gcagcggcac agacttcacc ctgaagatca gccgggtgga   300
ggctgaggat gtgggcgtct actactgcnn knnknnknnk nnkgtgcccc tgacctttgg   360
ccagggcacc aagctggaga tcaagcgtac ggtggctg                            398
```

<210> SEQ ID NO 123
<211> LENGTH: 82
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t

<400> SEQUENCE: 123

```
cagccaccgt acgcttgatc tccagcttgg tgccctggcc aaaggtcagg ggcacmnnmn    60
nmnnmnnmnn gcagtagtag ac                                              82
```

```
<210> SEQ ID NO 124
<211> LENGTH: 398
<212> TYPE: DNA
<213> ORGANISM: Artificial Sequence
<220> FEATURE:
<223> OTHER INFORMATION: Synthetic nucleic acid molecule
<220> FEATURE:
<221> NAME/KEY: misc_feature
<222> LOCATION: (341)..(342)
<223> OTHER INFORMATION: n is a, c, g, or t
<220> FEATURE:
<221> NAME/KEY: misc_feature
<222> LOCATION: (344)..(345)
<223> OTHER INFORMATION: n is a, c, g, or t
<220> FEATURE:
<221> NAME/KEY: misc_feature
<222> LOCATION: (347)..(348)
<223> OTHER INFORMATION: n is a, c, g, or t
<220> FEATURE:
<221> NAME/KEY: misc_feature
<222> LOCATION: (350)..(351)
<223> OTHER INFORMATION: n is a, c, g, or t
<220> FEATURE:
<221> NAME/KEY: misc_feature
<222> LOCATION: (353)..(354)
<223> OTHER INFORMATION: n is a, c, g, or t

<400> SEQUENCE: 124
agctgctggt ctgctgctgc tggcggccca gccggctatg gcttctagag atgtggtgat      60
gacccagagc ccctgtccc tgcctgtgac ccctggcgag cctgccagca tctcctgccg     120
gagctcccag agcatcctgc actccaatgg caacacctac ctggagtggt acctgcagaa     180
gcctggccag agcccccagc tgctgatcta caaggtgtcc aaccggttct ccggcgtgcc     240
tgaccggttc agcggctccg gcagcggcac agacttcacc ctgaagatca gccgggtgga     300
ggctgaggat gtgggcgtct actactgctt ccagggcagc nnknnknnkn nknnktttgg     360
ccagggcacc aagctggaga tcaagcgtac ggtggctg                             398

<210> SEQ ID NO 125
<211> LENGTH: 82
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (45)..(46)
<223> OTHER INFORMATION: n is a, c, g, or t
<220> FEATURE:
<221> NAME/KEY: misc_feature
<222> LOCATION: (48)..(49)
<223> OTHER INFORMATION: n is a, c, g, or t
<220> FEATURE:
<221> NAME/KEY: misc_feature
<222> LOCATION: (51)..(52)
<223> OTHER INFORMATION: n is a, c, g, or t
<220> FEATURE:
<221> NAME/KEY: misc_feature
<222> LOCATION: (54)..(55)
<223> OTHER INFORMATION: n is a, c, g, or t
<220> FEATURE:
<221> NAME/KEY: misc_feature
<222> LOCATION: (57)..(58)
<223> OTHER INFORMATION: n is a, c, g, or t

<400> SEQUENCE: 125
cagccaccgt acgcttgatc tccagcttgg tgccctggcc aaamnmnmnm nnmnnmnngc      60
tgccctggaa gcagtagtag ac                                              82
```

```
<210> SEQ ID NO 126
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 126
gtttatctcg agcaggtgac cctgaag                                         27

<210> SEQ ID NO 127
<211> LENGTH: 399
<212> TYPE: DNA
<213> ORGANISM: Artificial Sequence
<220> FEATURE:
<223> OTHER INFORMATION: Synthetic nucleic acid molecule

<400> SEQUENCE: 127
ccgtggccca ggcggccctc gagcaggtga ccctgaagga gtctggccct gccctggtga     60
agcccaccca gaccctgacc ctgacctgca ccttctctgg cttcagcctg agcacctctg    120
gcatgggcgt gggctggatc cggcagcccc ctggcaaggc cctggagtgg ctggcccaca    180
tctggtggga cgacgacaag tcctacaacc ccagcctgaa gagccggctg accatcagca    240
aggacaccag caagaaccag gtggtgctga ccatgaccaa catggaccct gtggacagtg    300
cccggcggca gctgggcctg cggagcattg atgccatgga ctactggggc cagggcacca    360
cagtgacagt gtccagcgcc tccaccaagg gcccatcgg                           399

<210> SEQ ID NO 128
<211> LENGTH: 399
<212> TYPE: DNA
<213> ORGANISM: Artificial Sequence
<220> FEATURE:
<223> OTHER INFORMATION: Synthetic nucleic acid molecule
<220> FEATURE:
<221> NAME/KEY: misc_feature
<222> LOCATION: (306)..(307)
<223> OTHER INFORMATION: n is a, c, g, or t
<220> FEATURE:
<221> NAME/KEY: misc_feature
<222> LOCATION: (309)..(310)
<223> OTHER INFORMATION: n is a, c, g, or t
<220> FEATURE:
<221> NAME/KEY: misc_feature
<222> LOCATION: (312)..(313)
<223> OTHER INFORMATION: n is a, c, g, or t
<220> FEATURE:
<221> NAME/KEY: misc_feature
<222> LOCATION: (315)..(316)
<223> OTHER INFORMATION: n is a, c, g, or t
<220> FEATURE:
<221> NAME/KEY: misc_feature
<222> LOCATION: (318)..(319)
<223> OTHER INFORMATION: n is a, c, g, or t

<400> SEQUENCE: 128
ccgtggccca ggcggccctc gagcaggtga ccctgaagga gtctggccct gccctggtga     60
agcccaccca gaccctgacc ctgacctgca ccttctctgg cttcagcctg agcacctctg    120
gcatgggcgt gggctggatc cggcagcccc ctggcaaggc cctggagtgg ctggcccaca    180
tctggtggga cgacgacaag tcctacaacc ccagcctgaa gagccggctg accatcagca    240
aggacaccag caagaaccag gtggtgctga ccatgaccaa catggaccct gtggacagtg    300
cccggnnknn knnknnknnk cggagcattg atgccatgga ctactggggc cagggcacca    360
cagtgacagt gtccagcgcc tccaccaagg gcccatcgg                           399
```

```
<210> SEQ ID NO 129
<211> LENGTH: 102
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (81)..(82)
<223> OTHER INFORMATION: n is a, c, g, or t
<220> FEATURE:
<221> NAME/KEY: misc_feature
<222> LOCATION: (84)..(85)
<223> OTHER INFORMATION: n is a, c, g, or t
<220> FEATURE:
<221> NAME/KEY: misc_feature
<222> LOCATION: (87)..(88)
<223> OTHER INFORMATION: n is a, c, g, or t
<220> FEATURE:
<221> NAME/KEY: misc_feature
<222> LOCATION: (90)..(91)
<223> OTHER INFORMATION: n is a, c, g, or t
<220> FEATURE:
<221> NAME/KEY: misc_feature
<222> LOCATION: (93)..(94)
<223> OTHER INFORMATION: n is a, c, g, or t

<400> SEQUENCE: 129
ccgatgggcc cttggtggag gcgctggaca ctgtcactgt ggtgccctgg ccccagtagt      60
ccatggcatc aatgctccgm nnmnnmnnmn nmnnccgggc ac                        102

<210> SEQ ID NO 130
<211> LENGTH: 399
<212> TYPE: DNA
<213> ORGANISM: Artificial Sequence
<220> FEATURE:
<223> OTHER INFORMATION: Synthetic nucleic acid molecule
<220> FEATURE:
<221> NAME/KEY: misc_feature
<222> LOCATION: (330)..(331)
<223> OTHER INFORMATION: n is a, c, g, or t
<220> FEATURE:
<221> NAME/KEY: misc_feature
<222> LOCATION: (333)..(334)
<223> OTHER INFORMATION: n is a, c, g, or t
<220> FEATURE:
<221> NAME/KEY: misc_feature
<222> LOCATION: (336)..(337)
<223> OTHER INFORMATION: n is a, c, g, or t
<220> FEATURE:
<221> NAME/KEY: misc_feature
<222> LOCATION: (339)..(340)
<223> OTHER INFORMATION: n is a, c, g, or t
<220> FEATURE:
<221> NAME/KEY: misc_feature
<222> LOCATION: (342)..(343)
<223> OTHER INFORMATION: n is a, c, g, or t

<400> SEQUENCE: 130
ccgtggccca ggcggccctc gagcaggtga ccctgaagga gtctggccct gccctggtga      60
agcccaccca gaccctgacc ctgacctgca ccttctctgg cttcagcctg agcacctctg     120
gcatgggcgt gggctggatc cggcagcccc ctggcaaggc cctggagtgg ctggcccaca     180
tctggtggga cgacgacaag tcctacaacc ccagcctgaa gagccggctg accatcagca     240
aggacaccag caagaaccag gtggtgctga ccatgaccaa catggaccct gtggacagtg     300
cccggcggca gctgggcctg cggagcattn nknnknnkn knnktggggc cagggcacca     360
cagtgacagt gtccagcgcc tccaccaagg gcccatcgg                            399

<210> SEQ ID NO 131
<211> LENGTH: 91
```

<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (57)..(58)
<223> OTHER INFORMATION: n is a, c, g, or t
<220> FEATURE:
<221> NAME/KEY: misc_feature
<222> LOCATION: (60)..(61)
<223> OTHER INFORMATION: n is a, c, g, or t
<220> FEATURE:
<221> NAME/KEY: misc_feature
<222> LOCATION: (63)..(64)
<223> OTHER INFORMATION: n is a, c, g, or t
<220> FEATURE:
<221> NAME/KEY: misc_feature
<222> LOCATION: (66)..(67)
<223> OTHER INFORMATION: n is a, c, g, or t
<220> FEATURE:
<221> NAME/KEY: misc_feature
<222> LOCATION: (69)..(70)
<223> OTHER INFORMATION: n is a, c, g, or t

<400> SEQUENCE: 131
ccgatgggcc cttggtggag gcgctggaca ctgtcactgt ggtgccctgg ccccamnnmn    60
nmnnmnnmnn aatgctccgc aggcccagct g                                  91

<210> SEQ ID NO 132
<211> LENGTH: 399
<212> TYPE: DNA
<213> ORGANISM: Artificial Sequence
<220> FEATURE:
<223> OTHER INFORMATION: Synthetic nucleic acid molecule
<220> FEATURE:
<221> NAME/KEY: misc_feature
<222> LOCATION: (318)..(319)
<223> OTHER INFORMATION: n is a, c, g, or t
<220> FEATURE:
<221> NAME/KEY: misc_feature
<222> LOCATION: (321)..(322)
<223> OTHER INFORMATION: n is a, c, g, or t
<220> FEATURE:
<221> NAME/KEY: misc_feature
<222> LOCATION: (324)..(325)
<223> OTHER INFORMATION: n is a, c, g, or t
<220> FEATURE:
<221> NAME/KEY: misc_feature
<222> LOCATION: (327)..(328)
<223> OTHER INFORMATION: n is a, c, g, or t
<220> FEATURE:
<221> NAME/KEY: misc_feature
<222> LOCATION: (330)..(331)
<223> OTHER INFORMATION: n is a, c, g, or t

<400> SEQUENCE: 132
ccgtggccca ggcggccctc gagcaggtga ccctgaagga gtctggccct gccctggtga    60
agcccaccca gaccctgacc ctgacctgca ccttctctgg cttcagcctg agcacctctg   120
gcatgggcgt gggctggatc cggcagcccc ctggcaaggc cctggagtgg ctggcccaca   180
tctggtggga cgacgacaag tcctacaacc ccagcctgaa gagccggctg accatcagca   240
aggacaccag caagaaccag gtggtgctga ccatgaccaa catggaccct gtggacagtg   300
cccggcggca gctgggcnnk nnknnknnkn nkgccatgga ctactggggc cagggcacca   360
cagtgacagt gtccagcgcc tccaccaagg gcccatcgg                          399

<210> SEQ ID NO 133
<211> LENGTH: 91
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (69)..(70)
<223> OTHER INFORMATION: n is a, c, g, or t
<220> FEATURE:
<221> NAME/KEY: misc_feature
<222> LOCATION: (72)..(73)
<223> OTHER INFORMATION: n is a, c, g, or t
<220> FEATURE:
<221> NAME/KEY: misc_feature
<222> LOCATION: (75)..(76)
<223> OTHER INFORMATION: n is a, c, g, or t
<220> FEATURE:
<221> NAME/KEY: misc_feature
<222> LOCATION: (78)..(79)
<223> OTHER INFORMATION: n is a, c, g, or t
<220> FEATURE:
<221> NAME/KEY: misc_feature
<222> LOCATION: (81)..(82)
<223> OTHER INFORMATION: n is a, c, g, or t

<400> SEQUENCE: 133
ccgatgggcc cttggtggag gcgctggaca ctgtcactgt ggtgccctgg ccccagtagt    60
ccatggcmnn mnnmnnmnnm nngcccagct g                                   91

<210> SEQ ID NO 134
<211> LENGTH: 330
<212> TYPE: PRT
<213> ORGANISM: Homo sapiens

<400> SEQUENCE: 134
```

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu

```
              225                 230                 235                 240
Leu Thr Lys Asn Gln Val Ser Leu Thr Cys Leu Val Lys Gly Phe Tyr
                    245                 250                 255

Pro Ser Asp Ile Ala Val Glu Trp Glu Ser Asn Gly Gln Pro Glu Asn
                260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 135
<211> LENGTH: 326
<212> TYPE: PRT
<213> ORGANISM: Homo sapiens

<400> SEQUENCE: 135

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Thr Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
```

```
                275                 280                 285
Leu Thr Val Asp Lys Ser Arg Trp Gln Gln Gly Asn Val Phe Ser Cys
290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 136
<211> LENGTH: 327
<212> TYPE: PRT
<213> ORGANISM: Homo sapiens

<400> SEQUENCE: 136

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
```

<210> SEQ ID NO 137
<211> LENGTH: 326
<212> TYPE: PRT
<213> ORGANISM: Artificial Sequence
<220> FEATURE:
<223> OTHER INFORMATION: Synthetic polypeptide

<400> SEQUENCE: 137

```
Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser Gln Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Leu His Gln Asp Trp
            180                 185                 190

Leu Asn Gly Lys Glu Tyr Lys Cys Lys Val Ser Asn Lys Gly Leu Pro
        195                 200                 205

Ser Ser Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ala Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325
```

<210> SEQ ID NO 138
<211> LENGTH: 449
<212> TYPE: PRT
<213> ORGANISM: Artificial Sequence

```
<220> FEATURE:
<223> OTHER INFORMATION: Synthetic polypeptide

<400> SEQUENCE: 138

Gln Val Thr Leu Lys Glu Ser Gly Pro Gly Leu Leu Lys Pro Thr Gln
1               5                   10                  15

Thr Leu Thr Leu Thr Cys Thr Leu Ser Gly Phe Ser Leu Ser Thr Ser
            20                  25                  30

Gly Met Gly Val Gly Trp Phe Arg Gln Pro Pro Gly Lys Gly Leu Glu
        35                  40                  45

Trp Leu Ala His Ile Trp Trp Asp Asp Asp Lys Ser Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Ile Thr Asn Val Asp Pro Val Asp Thr Ala Thr Tyr Tyr
                85                  90                  95

Cys Ala Arg Arg Gln Leu Gly Thr Arg Gly Thr Asp Ala Met Asp Tyr
            100                 105                 110

Trp Gly Gln Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Thr Ser Ser Asn Phe Gly Thr Gln Thr Tyr Thr Cys Asn Val
        195                 200                 205

Asp His Lys Pro Ser Asn Thr Lys Val Asp Lys Thr Val Glu Arg Lys
    210                 215                 220

Cys Cys Val Glu Cys Pro Pro Cys Pro Ala Pro Pro Val Ala Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Phe Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Thr Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Met Leu
385                 390                 395                 400
```

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 139
<211> LENGTH: 1407
<212> TYPE: DNA
<213> ORGANISM: Artificial Sequence
<220> FEATURE:
<223> OTHER INFORMATION: Synthetic nucleic acid molecule

<400> SEQUENCE: 139
atggaatgga gctgggtctt tctcttcttc ctgtcagtaa ctacaggtgt ccactcgcag     60
gtgaccctga aggagtctgg ccctggcctg ctgaagccca cccagaccct gaccctgacc    120
tgcaccctgt ctggcttcag cctgagcacc tctggcatgg gcgtgggctg gttccggcag    180
cccccctggc agggcctgga gtggctggcc cacatctggt gggacgacga caagtcctac    240
aaccccagcc tgaagagccg gctgaccatc agcaaggaca ccagcaagaa ccaggtggtg    300
ctgaccatca ccaacgtgga ccctgtggac acagccacct actactgtgc ccggcggcag    360
ctgggcacta gggggacgga tgccatggac tactggggcc agggcaccac agtgacagtg    420
tccagcgcat ccaccaaggg cccatccgtc ttccccctgg cgccctgctc caggagcacc    480
tccgagagca cagccgccct gggctgcctg gtcaaggact acttccccga accggtgacg    540
gtgtcgtgga actcaggcgc cctgaccagc ggcgtgcaca ccttcccggc tgtcctacag    600
tcctcaggac tctactccct cagcagcgtg gtgaccgtga cctccagcaa ctttggcacg    660
cagacctaca cctgcaacgt agatcacaag cccagcaaca ccaaggtgga caagacagtt    720
gagcggaaat gctgcgtgga gtgcccacca tgcccagcac ctccagtggc cggaccatca    780
gtcttcctgt tccccccaaa acccaaggac actctcatga tctcccggac ccctgaggtc    840
acgtgcgtgg tggtggacgt gagccaggaa gaccccgagg tccagttcaa ctggtacgtg    900
gatggcgtgg aggtgcataa tgccaagaca aagccgcggg aggagcagtt caacagcacg    960
ttccgtgtgg tcagcgtcct caccgtcctg caccaggact ggctgaacgg caaggagtac   1020
aagtgcaagg tctccaacaa aggcctcccg tcctccatcg agaaaaccat ctccaaaacc   1080
aaagggcagc cccgagagcc acaggtgtac accctgcccc catcccggga ggagatgacc   1140
aagaaccagg tcagcctgac ctgcctggtc aaaggcttct accccagcga catcgccgtg   1200
gagtgggaga gcaatgggca gccggagaac aactacaaga ccacgcctcc catgctggac   1260
tccgacggct ccttcttcct ctacagcaag ctaaccgtgg acaagagcag gtggcagcag   1320
gggaatgtct tctcatgctc cgtgatgcat gaggctctgc acaaccacta cacacagaag   1380
agcctctccc tgtctcctgg taaatga                                       1407

<210> SEQ ID NO 140
<211> LENGTH: 219
<212> TYPE: PRT
<213> ORGANISM: Artificial Sequence
<220> FEATURE:
<223> OTHER INFORMATION: Synthetic polypeptide

<400> SEQUENCE: 140

Asp Val Val Met Thr Gln Thr Pro Leu Ser Leu Pro Val Thr Pro Gly

```
             1               5                  10                 15
Gln Pro Ala Ser Ile Ser Cys Arg Ser Ser Gln Ser Ile Leu His Ser
            20                  25                 30

Asn Gly Asn Thr Tyr Leu Glu Trp Tyr Leu Gln Lys Pro Gly Gln Ser
            35                  40                 45

Pro Gln Leu Leu Ile Tyr Lys Val Ser Asn Arg Phe Ser Gly Val Pro
    50                  55                 60

Asp Arg Phe Ser Gly Ser Gly Ser Gly Thr Asp Phe Thr Leu Lys Ile
65                  70                  75                 80

Ser Arg Val Glu Ala Glu Asp Val Gly Val Tyr Tyr Cys Leu Gln Thr
                85                  90                 95

Thr Arg Val Pro Leu Thr Phe Gly Gln Gly Thr Lys Leu Glu Ile Lys
                100                 105                110

Arg Thr Val Ala Ala Pro Ser Val Phe Ile Phe Pro Pro Ser Asp Glu
            115                 120                125

Gln Leu Lys Ser Gly Thr Ala Ser Val Val Cys Leu Leu Asn Asn Phe
    130                 135                140

Tyr Pro Arg Glu Ala Lys Val Gln Trp Lys Val Asp Asn Ala Leu Gln
145                 150                 155                160

Ser Gly Asn Ser Gln Glu Ser Val Thr Glu Gln Asp Ser Lys Asp Ser
                165                 170                175

Thr Tyr Ser Leu Ser Ser Thr Leu Thr Leu Ser Lys Ala Asp Tyr Glu
                180                 185                190

Lys His Lys Val Tyr Ala Cys Glu Val Thr His Gln Gly Leu Ser Ser
                195                 200                205

Pro Val Thr Lys Ser Phe Asn Arg Gly Glu Cys
    210                 215
```

<210> SEQ ID NO 141
<211> LENGTH: 720
<212> TYPE: DNA
<213> ORGANISM: Artificial Sequence
<220> FEATURE:
<223> OTHER INFORMATION: Synthetic oligonucleotide

<400> SEQUENCE: 141

```
atgagtgtgc ccactcaggt cctggggttg ctgctgctgt ggcttacaga tgccagatgc     60
gatgtggtga tgacccagac cccctgtcc ctgcctgtga cccctggcca gcctgccagc    120
atctcctgcc ggagctccca gagcatcctg cactccaatg caacacctta cctggagtgg    180
tacctgcaga gcctggcca gagccccag ctgctgatct acaaggtgtc caaccggttc     240
tccggcgtgc ctgaccggtt cagcggctcc ggcagcggca cagacttcac cctgaagatc    300
agccgggtgg aggctgagga tgtgggcgtc tactactgcc ttcagactac tcgtgtgccc    360
ctgacctttg gccagggcac caagctggag atcaagcgta cggtggctgc accatctgtc    420
ttcatcttcc cgccatctga tgagcagttg aaatctggaa ctgcctctgt tgtgtgcctg    480
ctgaataact tctatcccag agaggccaaa gtacagtgga aggtggataa cgccctccaa    540
tcgggtaact cccaggagag tgtcacagag caggacagca aggacagcac ctacagcctc    600
agcagcaccc tgacgctgag caaagcagac tacgagaaac acaaagtcta cgcctgcgaa    660
gtcacccatc agggcctgag ctcgcccgtc acaaagagct tcaacagggg agagtgttag    720
```

<210> SEQ ID NO 142
<211> LENGTH: 13
<212> TYPE: PRT
<213> ORGANISM: Artificial Sequence

```
<220> FEATURE:
<223> OTHER INFORMATION: Synthetic peptide

<400> SEQUENCE: 142

Arg Gln Leu Gly Lys Leu Ala Leu Asp Ala Met Asp Tyr
1               5                   10

<210> SEQ ID NO 143
<211> LENGTH: 13
<212> TYPE: PRT
<213> ORGANISM: Artificial Sequence
<220> FEATURE:
<223> OTHER INFORMATION: Synthetic peptide

<400> SEQUENCE: 143

Arg Gln Leu Gly Leu Arg Ser Ile Asp Ala Met Asp Tyr
1               5                   10

<210> SEQ ID NO 144
<211> LENGTH: 13
<212> TYPE: PRT
<213> ORGANISM: Artificial Sequence
<220> FEATURE:
<223> OTHER INFORMATION: Synthetic peptide

<400> SEQUENCE: 144

Arg Gln Leu Gly Gln Arg Gln Thr Asp Ala Met Asp Tyr
1               5                   10

<210> SEQ ID NO 145
<211> LENGTH: 13
<212> TYPE: PRT
<213> ORGANISM: Artificial Sequence
<220> FEATURE:
<223> OTHER INFORMATION: Synthetic peptide

<400> SEQUENCE: 145

Arg Ala Ile Gln Pro Arg Ser Ile Asp Ala Met Asp Tyr
1               5                   10

<210> SEQ ID NO 146
<211> LENGTH: 13
<212> TYPE: PRT
<213> ORGANISM: Artificial Sequence
<220> FEATURE:
<223> OTHER INFORMATION: Synthetic peptide

<400> SEQUENCE: 146

Arg Gln Leu Gly Leu Arg Ser Ile Asp Ala His Thr Arg
1               5                   10

<210> SEQ ID NO 147
<211> LENGTH: 13
<212> TYPE: PRT
<213> ORGANISM: Artificial Sequence
<220> FEATURE:
<223> OTHER INFORMATION: Synthetic peptide

<400> SEQUENCE: 147

Arg Gln Leu Gly Gln Pro Ser Val Asp Ala Met Asp Tyr
1               5                   10

<210> SEQ ID NO 148
<211> LENGTH: 13
<212> TYPE: PRT
<213> ORGANISM: Artificial Sequence
<220> FEATURE:
<223> OTHER INFORMATION: Synthetic peptide
```

<400> SEQUENCE: 148

Arg Gln Leu Gly Phe Gln Ser Thr Asp Ala Met Asp Tyr
1               5                   10

<210> SEQ ID NO 149
<211> LENGTH: 13
<212> TYPE: PRT
<213> ORGANISM: Artificial Sequence
<220> FEATURE:
<223> OTHER INFORMATION: Synthetic peptide

<400> SEQUENCE: 149

Arg Gln Leu Gly Gln Ala Gly His Asp Ala Met Asp Tyr
1               5                   10

<210> SEQ ID NO 150
<211> LENGTH: 13
<212> TYPE: PRT
<213> ORGANISM: Artificial Sequence
<220> FEATURE:
<223> OTHER INFORMATION: Synthetic peptide

<400> SEQUENCE: 150

Arg Gln Leu Gly Asp Asn Val Ala Asp Ala Met Asp Tyr
1               5                   10

<210> SEQ ID NO 151
<211> LENGTH: 13
<212> TYPE: PRT
<213> ORGANISM: Artificial Sequence
<220> FEATURE:
<223> OTHER INFORMATION: Synthetic peptide

<400> SEQUENCE: 151

Arg Gln Leu Gly Met Ala Thr Pro Asp Ala Met Asp Tyr
1               5                   10

<210> SEQ ID NO 152
<211> LENGTH: 13
<212> TYPE: PRT
<213> ORGANISM: Artificial Sequence
<220> FEATURE:
<223> OTHER INFORMATION: Synthetic peptide

<400> SEQUENCE: 152

Arg Gln Leu Gly Ala His Trp Leu Asp Ala Met Asp Tyr
1               5                   10

<210> SEQ ID NO 153
<211> LENGTH: 13
<212> TYPE: PRT
<213> ORGANISM: Artificial Sequence
<220> FEATURE:
<223> OTHER INFORMATION: Synthetic peptide

<400> SEQUENCE: 153

Arg Gln Leu Gly Pro Glu Pro Gln Asp Ala Met Asp Tyr
1               5                   10

<210> SEQ ID NO 154
<211> LENGTH: 16
<212> TYPE: PRT
<213> ORGANISM: Artificial sequence
<220> FEATURE:
<223> OTHER INFORMATION: Synthetic peptide

<400> SEQUENCE: 154

```
Arg Ser Ser Gln Ser Ile Leu His Ser Asn Gly Asn Thr Tyr Leu Glu
1               5                   10                  15

<210> SEQ ID NO 155
<211> LENGTH: 7
<212> TYPE: PRT
<213> ORGANISM: Artificial sequence
<220> FEATURE:
<223> OTHER INFORMATION: Synthetic peptide

<400> SEQUENCE: 155

Lys Val Ser Asn Arg Phe Ser
1               5

<210> SEQ ID NO 156
<211> LENGTH: 7
<212> TYPE: PRT
<213> ORGANISM: Artificial sequence
<220> FEATURE:
<223> OTHER INFORMATION: Synthetic peptide

<400> SEQUENCE: 156

Thr Ser Gly Met Gly Val Gly
1               5

<210> SEQ ID NO 157
<211> LENGTH: 16
<212> TYPE: PRT
<213> ORGANISM: Artificial sequence
<220> FEATURE:
<223> OTHER INFORMATION: Synthetic peptide

<400> SEQUENCE: 157

His Ile Trp Trp Asp Asp Asp Lys Ser Tyr Asn Pro Ser Leu Lys Ser
1               5                   10                  15
```